(12) United States Patent
Kim et al.

(10) Patent No.: US 11,021,455 B2
(45) Date of Patent: Jun. 1, 2021

(54) BROMINATED FURANONE DERIVATIVE, METHOD FOR PREPARING SAME, AND PHARMACEUTICAL COMPOSITION CONTAINING SAME AS ACTIVE INGREDIENT

(71) Applicant: SEOUL NATIONAL UNIVERSITY R&DB FOUNDATION, Seoul (KR)

(72) Inventors: Byeong Moon Kim, Seoul (KR); Bong Kyu Choi, Seoul (KR); Jae Hyun Sim, Paju-si (KR); Eun Ju Ryu, Incheon (KR); Ji Su Park, Gimhae-si (KR); Il Hak Bae, Daegu (KR)

(73) Assignee: Seoul National University R&DB Foundation, Seoul (KR)

( * ) Notice: Subject to any disclaimer, the term of this patent is extended or adjusted under 35 U.S.C. 154(b) by 286 days.

(21) Appl. No.: 16/309,710

(22) PCT Filed: Jun. 13, 2017

(86) PCT No.: PCT/KR2017/006151
§ 371 (c)(1),
(2) Date: Mar. 21, 2019

(87) PCT Pub. No.: WO2017/217741
PCT Pub. Date: Dec. 21, 2017

(65) Prior Publication Data
US 2019/0345126 A1    Nov. 14, 2019

(30) Foreign Application Priority Data
Jun. 13, 2016 (KR) .................. 10-2016-0073078

(51) Int. Cl.
| | |
|---|---|
| *C07D 307/88* | (2006.01) |
| *A61P 31/04* | (2006.01) |
| *C07D 209/46* | (2006.01) |
| *C07D 307/93* | (2006.01) |

(52) U.S. Cl.
CPC ............ *C07D 307/88* (2013.01); *A61P 31/04* (2018.01); *C07D 209/46* (2013.01); *C07D 307/93* (2013.01)

(58) Field of Classification Search
CPC .. C07D 307/88; C07D 307/93; A61K 31/345; A61P 31/04; A61Q 11/00
See application file for complete search history.

(56) References Cited

FOREIGN PATENT DOCUMENTS

| | | |
|---|---|---|
| EP | 0 041 283 | 12/1981 |
| JP | 2001-335571 | 12/2001 |
| WO | WO 02/00639 A1 | 1/2002 |

OTHER PUBLICATIONS

Gabriel, Berichte der Deutschen Chemischen Gosellschaft/Ber. Dtsch. Chem. Ges., vol. 40, pp. 71-83, 1907. (Year: 1907).*
Chemical Abstract Compound, STN express. RN 93089-82-8 (1984).
Chemical Abstract Compound, STN express. RN 873395-18-7 (2006).
STN Database Registry (online), CAS Registry No. 873395-18-7 (2006).
Benneche et al. "Synthesis of 5-(bromomethylene)furan-2(5H)-ones and 3-(bromomethylene)isobenzofuran-1(3H)-ones as inhibitors of microbial quorum sensing," *New Journal of Chemistry* 32:1567-1535 (2008).
Lönn-Stensrud et al. "Furanones, potential agents for preventing *Staphylococcus epidermidis* biofilm infections?" *Journal of Antimicrobial Chemotherapy* 63:309-316 (2009).
Park et al. "New bicyclic brominated furanones as potent autoinducer-2 quorum-sensing inhibitors against bacterial biofilm formation," *European Journal of Medicinal Chemistry* 137:76-87 (2017).

* cited by examiner

*Primary Examiner* — D Margaret M Seaman
(74) *Attorney, Agent, or Firm* — Klarquist Sparkman, LLP

(57) ABSTRACT

The present invention relates to a novel brominated furanone derivative, a method for preparing the same, and a pharmaceutical composition containing the same as an active ingredient, wherein the novel brominated furanone derivative or a pharmaceutically acceptable 5 salt thereof according to the present invention exhibits a quorum sensing inhibitory activity of bacteria and also can effectively inhibit the formation of biofilm of bacteria, and thus can be used as a pharmaceutical composition containing the same as an active ingredient, thereby having an effect of being useful, 10 for example, for periodontal diseases such as gingivitis and periodontitis, oral diseases, and the like.

10 Claims, 25 Drawing Sheets
Specification includes a Sequence Listing.

```
                           SEQUENCE LISTING

<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
gtggccagcc gagcc                                                        15

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
tgaaggggtt gatggca                                                      17

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
gattcaatga ggagacttgc ctgg                                              24

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
gcagaactgg atcaggactt t                                                 21

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
ctgtgtgaag gtgcagtttt gc                                                22

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
aacttctcca caccctctg c                                                  21
```

BROMINATED FURANONE DERIVATIVE, METHOD FOR PREPARING SAME, AND PHARMACEUTICAL COMPOSITION CONTAINING SAME AS ACTIVE INGREDIENT

CROSS REFERENCE TO RELATED APPLICATIONS

This is the U.S. National Stage of International Application No. PCT/KR2017/006151, filed Jun. 13, 2017, which in turn claims the benefit of Korean Patent Application No. 10-2016-0073078, filed Jun. 13, 2016, both of which applications are herein incorporated in their entirety.

BACKGROUND OF THE INVENTION

1. Field of the Invention

The present invention relates to a novel brominated furanone derivative, a method for preparing the same, and a pharmaceutical composition containing the same as an active ingredient.

2. Description of the Related Art

When bacteria reach a certain level of cell density, the bacteria cells transmit signals between the cells by using a chemical language, by which they regulate a certain gene expression. Gram negative bacteria and Gram positive bacteria have a quorum sensing (QS) mechanism, wherein gene expression depends on cell density. Quorum sensing can be expressed by the recognition of proper density, and refers to a series of biological phenomena in which each bacterium induces active proliferation to fill up quorum by accumulating low molecular signaling molecules such as autoinducer or pheromone extracellularly.

Particularly, among the proteins that make up bacteria, N-acyl homoserine lactone synthase protein synthesizes a signaling molecule called N-acyl Homoserine lactone (AHL). The synthesized normal acyl homoserine lactone diffuses freely through cell membrane during the growth of bacteria and accumulates in the extracellular environment. When the concentration of the signaling molecule accumulated in the extracellular environment reaches a certain level as the density of bacteria increases, the signaling molecule enters in the cell again and binds to the transcriptional regulator to promote the expression of a specific gene.

Bacteria can regulate various physiological phenomena such as biofilm formation, virulence, bioluminescence, generation of antibiotics and delivery of a tumor inducing (Ti) plasmid by conjugation through the quorum sensing mechanism mentioned above. For example, in the course of a series of bacterial infections, bacteria first find their way into the host and settle on the appropriate habitat for survival. Then, bacteria neutralize the primary defense system of the host to survive. Finally, bacteria multiply in large quantities and spread their offspring to other hosts. In the process above, bacteria can express various virulence factors by the quorum sensing mechanism.

Most of the conventional antimicrobial agents developed so far have shown their antimicrobial activity by killing bacteria. However, not only killing bacteria, but also preventing the proliferation of bacteria in advance by interfering with the communication of bacteria is equally important to control the bacteria, a cause of disease.

The formation of biofilm is a representative function achieved by the communication among bacteria. The said biofilm stays in human organs and causes causing many disease symptoms.

The disease symptom or the lesion can be exemplified by dental caries, gingivitis, periodontitis, otitis media, voice prostheses, hydrocephalus hunts, cystic fibrosis, valvular endocarditis, prosthetic heart valves, central venous catheter, prosthetic hip joint, prosthetic knee joint, chronic bacterial prostatitis, intrauterine devices, and urinary catheter, etc. Therefore, it is required to develop a novel multifunctional antimicrobial agent not only to kill bacteria but also to inhibit the function of biofilm formation of bacteria in advance by interrupting the communication among the bacteria.

In particular, it is known that gram negative bacteria communicate each other by using a chemical called N-acylhomoserine lactone (AHL). So, if an antagonist having a structure similar to N-acylhomoserine lactone (AHL) is synthesized and applied to the habitat of bacteria, the proliferation of bacteria might be prevented by interrupting the gene expression in the bacteria. Therefore, it is requested to develop an antimicrobial agent with multiple mechanisms for antimicrobial activity using a molecular structure that is useful for killing bacteria and at the same time for interrupting the communication among microorganisms so as not to proliferate further.

Korean Patent Publication No. 10-2008-0046434 describes a method of removing bacteria using a compound that shows an antimicrobial activity and is at the same time functioning as a quorum sensing antagonist. However, the quorum sensing inhibitory effect and antimicrobial activity of the compound according to the patent document above are still unsatisfactory, and no commercial products using the said compound are on the market yet.

The present inventors have studied to search a quorum sensing inhibitor. As a result, the present inventors confirmed that a novel brominated furanone derivative or a pharmaceutically acceptable salt thereof was able to inhibit quorum sensing function of bacteria and thus inhibit the formation of biofilm, and thereby exhibited antibacterial effect, leading to the completion of the present invention.

SUMMARY OF THE INVENTION

It is an object of the present invention to provide a novel brominated furanone derivative, an optical isomer thereof or a pharmaceutically acceptable salt thereof.

It is another object of the present invention to provide a method for preparing the brominated furanone derivative above.

It is also an object of the present invention to provide a pharmaceutical composition comprising the brominated furanone derivative, the optical isomer thereof or the pharmaceutically acceptable salt thereof as an active ingredient for the prevention or treatment of periodontal diseases.

It is further an object of the present invention to provide a dentifrice composition comprising the brominated furanone derivative, the optical isomer thereof or the pharmaceutically acceptable salt thereof as an active ingredient for the prevention or improvement of periodontal diseases.

It is also an object of the present invention to provide a gargle composition comprising the brominated furanone derivative, the optical isomer thereof or the pharmaceutically acceptable salt thereof as an active ingredient for the prevention or improvement of periodontal diseases.

To achieve the above objects, the present invention provides a compound represented by formula 1 below or a pharmaceutically acceptable salt thereof.

[Formula 1]

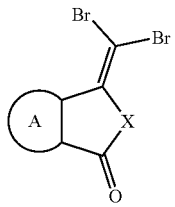

In formula 1,

X is O, S or NR$^1$,

Wherein R$^1$ is nonsubstituted or substituted C$_{1-10}$ straight or branched alkyl, nonsubstituted or substituted C$_{1-10}$ straight or branched alkoxy, nonsubstituted or substituted C$_{3-7}$ cycloalkyl, nonsubstituted or substituted 3~7 membered heterocycloalkyl containing one or more heteroatoms selected from the group consisting of N, O and S, nonsubstituted or substituted C$_{6-10}$ aryl, or nonsubstituted or substituted 5~10 membered heteroaryl containing one or more heteroatoms selected from the group consisting of N, O and S.

Wherein, the substituted alkyl, alkoxy, cycloalkyl, heterocycloalkyl, aryl, or heteroaryl is independently substituted with one or more substituents selected from the group consisting of hydroxyl, halogen, —CN, —NO$_2$, C$_{1-5}$ straight or branched alkyl, and C$_{1-5}$ straight or branched alkoxy; and (A) is nonsubstituted or substituted C$_{3-7}$ cycloalkyl, nonsubstituted or substituted C$_{3-7}$ cycloalkenyl containing one or more double bonds, nonsubstituted or substituted 3~7 membered heterocycloalkyl containing one or more heteroatoms selected from the group consisting of N, O and S, nonsubstituted or substituted C$_{6-10}$ aryl, or nonsubstituted or substituted 5~10 membered heteroaryl containing one or more heteroatoms selected from the group consisting of N, O and S.

Wherein, the substituted cycloalkyl, cycloalkenyl heterocycloalkyl, aryl, or heteroaryl is independently substituted with one or more substituents selected from the group consisting of hydroxyl, halogen, —CN, —NO$_2$, C$_{1-10}$ straight or branched alkyl, and C$_{1-10}$ straight or branched alkoxy.

The present invention also provides a preparation method of the compound represented by formula 1 comprising the following steps, as shown in reaction formula 1 below:

preparing the compound represented by formula 3 from the compound represented by formula 2 (step 1); and preparing the compound represented by formula 1 from the compound represented by formula 3 prepared in step 1 (step 2).

[Reaction Formula 1]

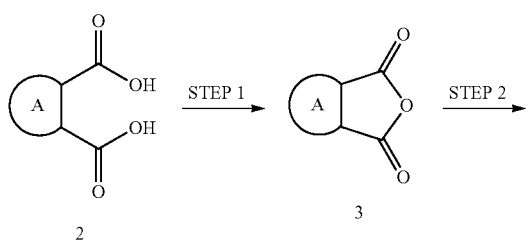

In reaction formula 1, (A) is as defined in formula 1; and
X is O.

In addition, the present invention provides a preparation method of the compound represented by formula 1 comprising the following steps, as shown in reaction formula 2 below:

preparing the compound represented by formula 3 from the compound represented by formula 2 (step 1);

preparing the compound represented by formula 4 from the compound represented by formula 3 prepared in step 1 (step 2);

preparing the compound represented by formula 6 by reacting the compound represented by formula 5 with the compound represented by formula 4 prepared in step 2 (step 3); and preparing the compound represented by formula 1 from the compound represented by formula 6 prepared in step 3 (step 4).

[Reaction Formula 2]

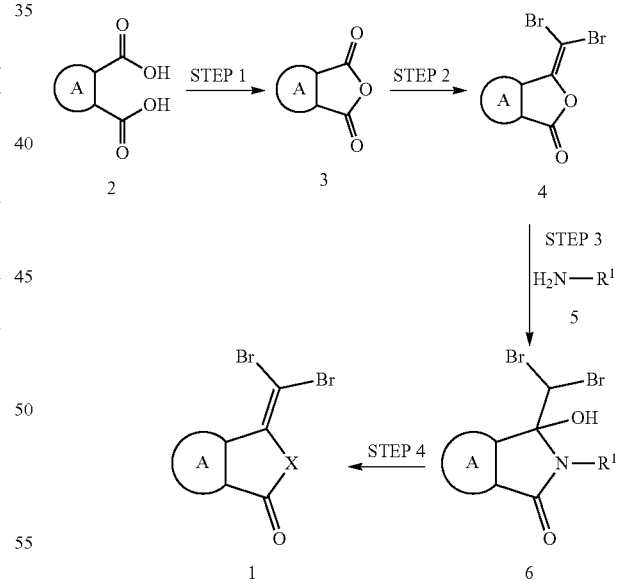

In reaction formula 2, (A) is as defined in formula 1; and
X is NR$^1$.

The present invention also provides a pharmaceutical composition comprising the compound represented by formula 1 or the pharmaceutically acceptable salt thereof as an active ingredient for the prevention or treatment of periodontal diseases.

The present invention also provides a dentifrice composition comprising the compound represented by formula 1 or the pharmaceutically acceptable salt thereof as an active ingredient for the prevention or improvement of periodontal diseases.

In addition, the present invention provide a gargle composition comprising the compound represented by formula 1 or the pharmaceutically acceptable salt thereof as an active ingredient for the prevention or improvement of periodontal diseases.

Advantageous Effect

The novel brominated furanone derivative or a pharmaceutically acceptable salt thereof according to the present invention exhibits a quorum sensing inhibitory activity of bacteria and also can effectively inhibit the formation of biofilm of bacteria, and thus can be used as a pharmaceutical composition containing the same as an active ingredient, thereby having an effect of being useful, for example, for periodontal diseases such as gingivitis and periodontitis, and oral diseases, etc.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
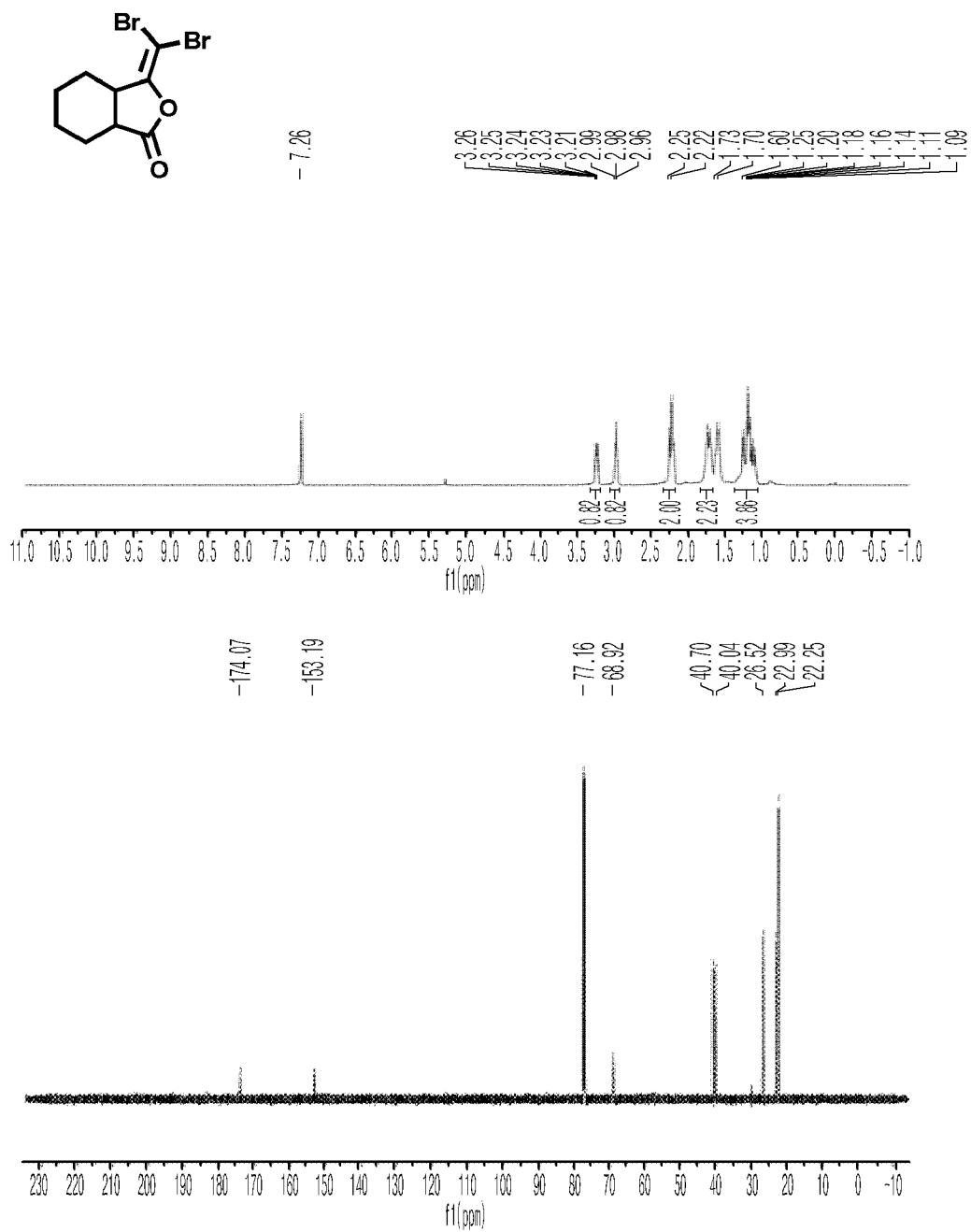
FIG. 1 is a set of graphs illustrating the results of NMR in which the upper graph is a graph showing the results of $^1$H NMR of Example 1, and the lower graph is a graph showing the results of $^{13}$C NMR of Example 1.

Hereinafter, the present invention is described in detail.

The following description is provided in order to help the understanding of the invention, and the present invention is not limited thereto.

The present invention provides a compound represented by formula 1 below or a pharmaceutically acceptable salt thereof.

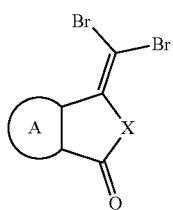

[Formula 1]

In formula 1,

X is O, S or $NR^1$,

Wherein $R^1$ is nonsubstituted or substituted $C_{1-10}$ straight or branched alkyl, nonsubstituted or substituted $C_{1-10}$ straight or branched alkoxy, nonsubstituted or substituted $C_{3-7}$ cycloalkyl, nonsubstituted or substituted 3~7 membered heterocycloalkyl containing one or more heteroatoms selected from the group consisting of N, O and S, nonsubstituted or substituted $C_{6-10}$ aryl, or nonsubstituted or substituted 5~10 membered heteroaryl containing one or more heteroatoms selected from the group consisting of N, O and S, Wherein, the substituted alkyl, alkoxy, cycloalkyl, heterocycloalkyl, aryl, or heteroaryl is independently substituted with one or more substituents selected from the group consisting of hydroxyl, halogen, —CN, —NO$_2$, $C_{1-5}$ straight or branched alkyl, and $C_{1-5}$ straight or branched alkoxy; and Ⓐ is nonsubstituted or substituted $C_{3-7}$ cycloalkyl, nonsubstituted or substituted $C_{3-7}$ cycloalkenyl containing one or more double bonds, nonsubstituted or substituted 3~7 membered heterocycloalkyl containing one or more heteroatoms selected from the group consisting of N, O and S, nonsubstituted or substituted $C_{6-10}$ aryl, or nonsubstituted or substituted 5~10 membered heteroaryl containing one or more heteroatoms selected from the group consisting of N, O and S, Wherein, the substituted cycloalkyl, cycloalkenyl, heterocycloalkyl, aryl, or heteroaryl is independently substituted with one or more substituents selected from the group consisting of hydroxyl, halogen, —CN, —NO$_2$, $C_{1-10}$ straight or branched alkyl, and $C_{1-10}$ straight or branched alkoxy.

Preferably,

Ⓐ is nonsubstituted or substituted $C_{5-6}$ cycloalkyl, nonsubstituted or substituted $C_{5-6}$ cycloalkenyl containing one or more double bonds, or nonsubstituted or substituted $C_{5-6}$ phenyl, Wherein, the substituted cycloalkyl, cycloalkenyl, or phenyl is independently substituted with one or more substituents selected from the group consisting of $C_{1-5}$ straight or branched alkyl and $C_{1-5}$ straight or branched alkoxy.

More preferably, $R^1$ is phenyl or n-butyl; and

Ⓐ is

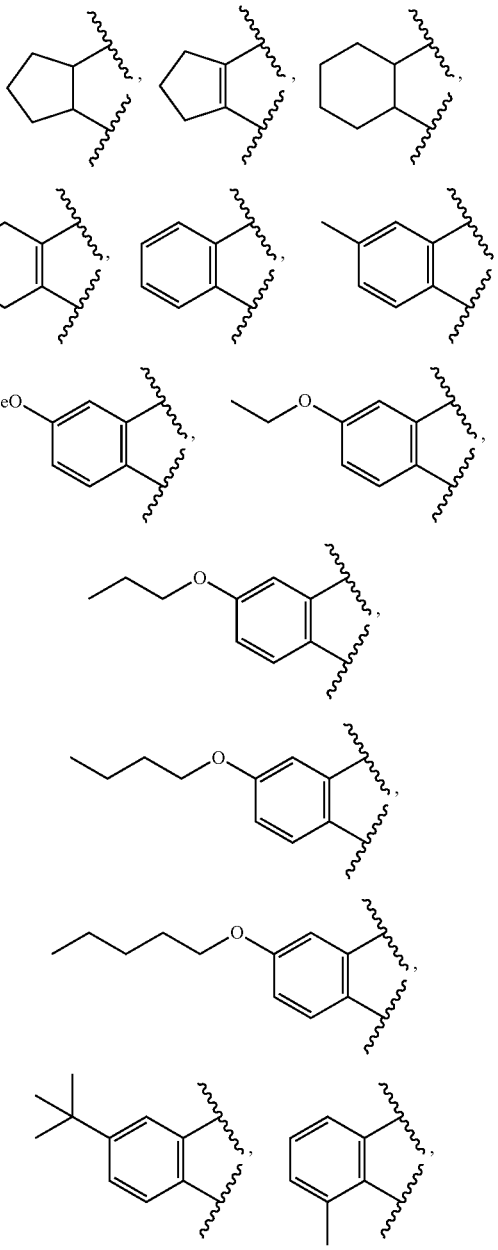

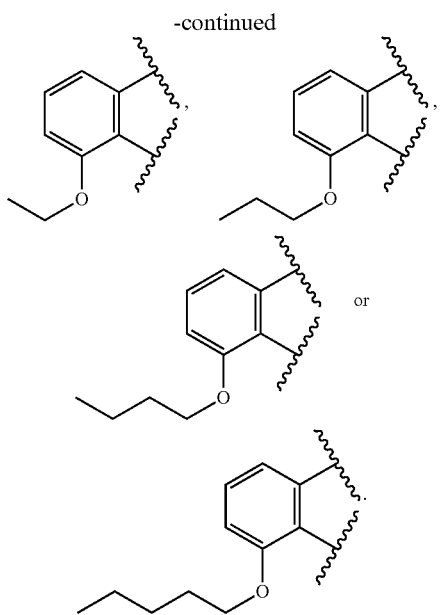

The following compounds are preferred examples of the compound represented by formula 1 according to the present invention.

(1) 3-(dibromomethylene)-hexahydroisobenzofuran-1(3H)-one;
(2) 3-(dibromomethylene)isobenzofuran-1(3H)-one;
(3) 3-(dibromomethylene)-4,5,6,7-tetrahydroisobenzofuran-1(3H)-one;
(4) 3-(dibromomethylene)-5,6-dihydro-3H-cyclopenta[c]furan-1(4H)-one;
(5) 3-(dibromomethylene)-hexahydrocyclopenta[c]furan-1(3H)-one;
(6) 3-(dibromomethylene)-5-methylisobenzofuran-1(3H)-one;
(7) 3-(dibromomethylene)-5-methoxyisobenzofuran-1(3H)-one;
(8) 3-(dibromomethylene)-5-ethoxyisobenzofuran-1(3H)-one;
(9) 3-(dibromomethylene)-5-propoxyisobenzofuran-1(3H)-one;
(10) 5-butoxy-3-(dibromomethylene)isobenzofuran-1(3H)-one;
(11) 3-(dibromomethylene)-5-(pentyloxy)isobenzofuran-1(3H)-one;
(12) 5-tert-butyl-3-(dibromomethylene)-5-methylisobenzofuran-1(3H)-one;
(13) 3-(dibromomethylene)-7-methylisobenzofuran-1(3H)-one;
(14) 3-(dibromomethylene)-7-ethoxyisobenzofuran-1(3H)-one;
(15) 3-(dibromomethylene)-7-propoxyisobenzofuran-1(3H)-one;
(16) 7-butoxy-3-(dibromomethylene)isobenzofuran-1(3H)-one;
(17) 3-(dibromomethylene)-7-(pentyloxy)isobenzofuran-1(3H)-one; and
(18) 2-butyl-3-(dibromomethylene)isoindolin-1-one.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, an optical isomer, or a hydrate possibly produced from the same.

The present invention also provides a preparation method of the compound represented by formula 1 comprising the following steps, as shown in reaction formula 1 below:
preparing the compound represented by formula 3 from the compound represented by formula 2 (step 1); and
preparing the compound represented by formula 1 from the compound represented by formula 3 prepared in step 1 (step 2).

[Reaction Formula 1]

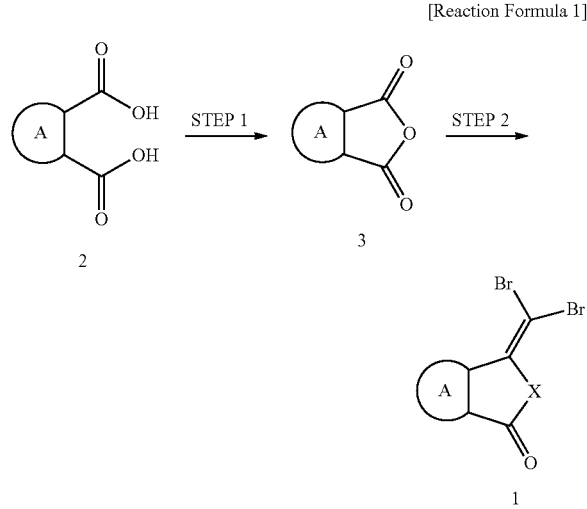

In reaction formula 1, (A) is as defined in formula 1; and

X is O.

Hereinafter, the preparation method of the compound represented by formula 1 of the present invention is described in more detail, step by step.

In the preparation method of the compound represented by formula 1 of the present invention, step 1 of reaction formula 1 is to prepare the compound represented by formula 3 from the compound represented by formula 2.

At this time, the step above is a cyclization reaction, but not always limited thereto, and can be accomplished by using acetic anhydride. In the step above, the reaction time is not particularly limited but it is preferable that the reaction is carried out for 5~35 hours.

In a most preferred embodiment, the method of the present invention can be achieved in accordance with the following examples, and any modifications of the embodiments of the experiment, conditions and the like, and any methods by which the compound represented by formula 3 can be prepared from the compound represented by formula 2 are included in the scope of the present invention.

In the preparation method of the compound represented by formula 1 above, step 2 of reaction formula 1 is to prepare the compound represented by formula 1 from the compound represented by formula 3 prepared in step 1 above.

At this time, the step above is a bromination reaction, but not always limited thereto, and can be accomplished by using $CBr_4$. The usable solvent in this step is exemplified by $H_2O$, ethanol, tetrahydrofuran (THF), dichloromethane, toluene, acetonitrile, and dimethylformamide, among which tetrahydrofuran (THF) is more preferred. In the step above, the reaction time is not particularly limited but it is preferable that the reaction is carried out for 3~30 hours. The reaction temperature is preferably at room temperature or 20~30° C.

In a most preferred embodiment, the method of the present invention can be achieved in accordance with the following examples, and any modifications of the embodiments of the experiment, conditions and the like, and any methods by which the compound represented by formula 1 can be prepared from the compound represented by formula 3 are included in the scope of the present invention.

In addition, the present invention provides a preparation method of the compound represented by formula 1 comprising the following steps, as shown in reaction formula 2 below:

preparing the compound represented by formula 3 from the compound represented by formula 2 (step 1);

preparing the compound represented by formula 4 from the compound represented by formula 3 prepared in step 1 (step 2);

preparing the compound represented by formula 6 by reacting the compound represented by formula 5 with the compound represented by formula 4 prepared in step 2 (step 3); and preparing the compound represented by formula 1 from the compound represented by formula 6 prepared in step 3 (step 4).

[Reaction Formula 2]

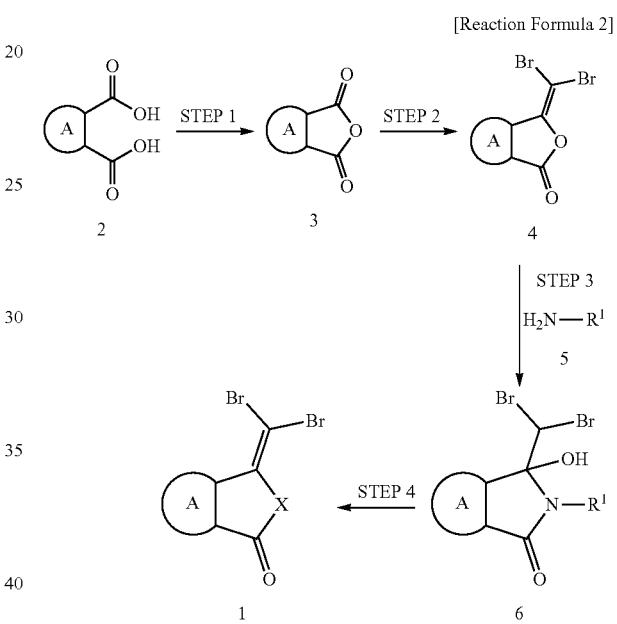

In reaction formula 2, (A) and $R^1$ are as defined in formula 1; and

X is $NR^1$.

Hereinafter, the preparation method of the compound represented by formula 1 of the present invention as shown in reaction formula 2 is described in more detail, step by step.

In the preparation method of the compound represented by formula 1 of the present invention, step 1 of reaction formula 2 is to prepare the compound represented by formula 3 from the compound represented by formula 2.

At this time, the step above is a cyclization reaction, but not always limited thereto, and can be accomplished by using acetic anhydride. In the step above, the reaction time is not particularly limited but it is preferable that the reaction is carried out for 5~35 hours.

In a most preferred embodiment, the method of the present invention can be achieved in accordance with the following examples, and any modifications of the embodiments of the experiment, conditions and the like, and any methods by which the compound represented by formula 3 can be prepared from the compound represented by formula 2 are included in the scope of the present invention.

In the preparation method of the compound represented by formula 1 above, step 2 of reaction formula 2 is to prepare the compound represented by formula 4 from the compound represented by formula 3 prepared in step 1 above.

At this time, the step above is a bromination reaction, but not always limited thereto, and can be accomplished by using $CBr_4$. The usable solvent in this step is exemplified by $H_2O$, ethanol, tetrahydrofuran (THF), dichloromethane, toluene, acetonitrile, and dimethylformamide, among which tetrahydrofuran (THF) is more preferred. In the step above, the reaction time is not particularly limited but it is preferable that the reaction is carried out for 3~30 hours. The reaction temperature is preferably at room temperature or 20~30° C.

In a most preferred embodiment, the method of the present invention can be achieved in accordance with the following examples, and any modifications of the embodiments of the experiment, conditions and the like, and any methods by which the compound represented by formula 4 can be prepared from the compound represented by formula 3 are included in the scope of the present invention.

In the preparation method of the compound represented by formula 1 above, step 3 of reaction formula 2 is to prepare the compound represented by formula 6 by reacting the compound represented by formula 5 with the compound represented by formula 4 prepared in step 2.

At this time, the step above is to introduce $N-R^1$ into the X position of formula 1, but not always limited thereto. The usable solvent in this step is exemplified by $H_2O$, ethanol, tetrahydrofuran (THF), dichloromethane, toluene, acetonitrile, and dimethylformamide, among which tetrahydrofuran (THF) is more preferred. In the step above, the reaction time is not particularly limited but it is preferable that the reaction is carried out for 0.5~20 hours. The reaction temperature is preferably at room temperature or 0~30° C.

In a most preferred embodiment, the method of the present invention can be achieved in accordance with the following examples, and any modifications of the embodiments of the experiment, conditions and the like, and any methods by which the compound represented by formula 6 can be prepared by reacting the compound represented by formula 5 with the compound represented by formula 4 are included in the scope of the present invention.

In the preparation method of the compound represented by formula 1 above, step 4 of reaction formula 2 is to prepare the compound represented by formula 1 from the compound represented by formula 6 prepared in step 3 above.

At this time, the step can be accomplished by using p-toluene sulfonic acid. The usable solvent in this step is exemplified by $H_2O$, ethanol, tetrahydrofuran (THF), dichloromethane, toluene, acetonitrile, and dimethylformamide, among which tetrahydrofuran (THF) is more preferred. In the step above, the reaction time is not particularly limited but it is preferable that the reaction is carried out for 0.5~20 hours. The reaction temperature is preferably at room temperature or 20~30° C.

In a most preferred embodiment, the method of the present invention can be achieved in accordance with the following examples, and any modifications of the embodiments of the experiment, conditions and the like, and any methods by which the compound represented by formula 1 can be prepared from the compound represented by formula 6 are included in the scope of the present invention.

The present invention also provides a pharmaceutical composition comprising the compound represented by formula 1 or the pharmaceutically acceptable salt thereof as an active ingredient for the prevention or treatment of periodontal diseases.

Herein, the compound represented by formula 1 above or the pharmaceutically acceptable salt thereof has a mechanism of inhibiting the quorum sensing of bacteria and has a mechanism of inhibiting the biofilm formation of bacteria. Thereby, the compound represented by formula 1 or the pharmaceutically acceptable salt thereof can inhibit the pathological activity of bacteria exposed on the site treated with the compound or the pharmaceutically acceptable salt thereof. Preferably, the compound represented by formula 1 or the pharmaceutically acceptable salt thereof can be used as an active ingredient of a pharmaceutical composition for the prevention or treatment of oral diseases and periodontal disease, precisely periodontitis, gingivitis and the like. The compound represented by formula 1 or the pharmaceutically acceptable salt thereof can be applied to diseases such as inflammation caused by bacteria in the body of a human or mammal to which the above-mentioned effects can be applied and can show useful effects, and this is included in the scope of the present invention.

More specifically, quorum sensing can be expressed by the recognition of proper density, and refers to a series of biological phenomena in which each bacterium induces active proliferation to fill up quorum by accumulating low molecular signaling molecules such as autoinducer or pheromone extracellularly.

Particularly, among the proteins that make up bacteria, N-acyl homoserine lactone synthase protein synthesizes a signaling molecule called N-acyl Homoserine lactone (AHL). The synthesized normal acyl homoserine lactone diffuses freely through cell membrane during the growth of bacteria and accumulates in the extracellular environment. When the concentration of the signaling molecule accumulated in the extracellular environment reaches a certain level as the density of bacteria increases, the signaling molecule enters in the cell again and binds to the transcriptional regulator to promote the expression of a specific gene. Bacteria can regulate various physiological phenomena such as biofilm formation, virulence, bioluminescence, generation of antibiotics and delivery of a tumor inducing (Ti) plasmid by conjugation through the quorum sensing mechanism mentioned above.

The compound represented by formula 1 above has a similar structure to N-acyl homoserine lactone (AHL), a signaling molecule synthesized by bacteria. Therefore, if this compound is applied, the communication among bacteria where the compound is applied can be interrupted, leading to the inhibition of gene expression. Accordingly, not only the formation of biofilm which is known to increase resistance against antibiotics but also bacteria proliferation can be prevented.

In relation to the above, an experiment was performed to evaluate the inhibitory activity of the compound represented by formula 1, the optical isomer thereof or the pharmaceutically acceptable salt thereof against AI-2 (autoinducer-2) which is a quorum sensing signaling molecule. As a result, it was confirmed that the compounds of examples of the present invention were able to inhibit the quorum sensing signaling molecule A1-2 (autoinducer-2), which was presented as a low bioluminescence value (see Experimental Example 1).

Another experiment was also performed to evaluate the ability of the compound represented by formula 1 or the pharmaceutically acceptable salt thereof of the present invention to inhibit the formation of biofilm of bacteria. As a result, the compounds of examples of the present invention were able to reduce the formation of biofilm, when bacteria were cultured with the compound (see Experimental Example 2).

In addition, an experiment was performed to evaluate the cytotoxicity of the compound represented by formula 1 or the pharmaceutically acceptable salt thereof of the present invention in host cells (normal cells). As a result, it was confirmed that the compound of the present invention did not display cytotoxicity in the host cells, indicating that the compound is appropriate to be used as a drug (see Experimental Example 3).

The present inventors also performed an experiment to evaluate whether the compound represented by formula 1 or the pharmaceutically acceptable salt thereof of the present invention was suitable as a drug for treating periodontal disease such as gingivitis and periodontitis. As a result, furanone used as a control induced inflammatory responses in host cells (normal cells), whereas the compound of the present invention did not induce inflammatory responses in normal cells. Therefore, it was confirmed that the compound of the present invention had a significant superiority as a therapeutic agent (see Experimental Example 4).

The novel furanone derivative or the pharmaceutically acceptable salt thereof according to the present invention demonstrated excellence as a quorum sensing antagonist to interrupt the communication among bacteria, so that it can efficiently inhibit the formation of biofilm known to increase resistance against antibiotics and bacteria proliferation as well, suggesting that the compound of the present invention can be effectively used as a pharmaceutical composition for the prevention or treatment of periodontal disease.

The compound represented by formula 1 according to the present invention can be prepared for oral or parenteral administration by mixing with generally used diluents or excipients such as fillers, extenders, binders, wetting agents, disintegrating agents and surfactants.

Solid formulations for oral administration are tablets, pills, powders, granules, capsules and troches. These solid formulations are prepared by mixing one or more the compounds of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the compound of the present invention can vary depending on the patient's age, weight, gender, administration form, health condition and disease severity, which is generally about 0.001-100 mg/kg/day, and preferably 0.01-35 mg/kg/day. Based on an adult patient weighing 70 kg, the dosage is generally 0.07-7000 mg/day, and preferably 0.7-2500 mg/day. The compound of the present invention can be administered once or several times a day at a predetermined time interval according to the judgment of a doctor or a pharmacist.

The present invention also provides a dentifrice composition comprising the compound represented by formula 1 or the pharmaceutically acceptable salt thereof as an active ingredient for the prevention or improvement of periodontal diseases.

In addition, the present invention provide a gargle composition comprising the compound represented by formula 1 or the pharmaceutically acceptable salt thereof as an active ingredient for the prevention or improvement of periodontal diseases.

At this time, the dentifrice or the gargle composition may include the compound represented by formula 1 or the pharmaceutically acceptable salt thereof of the present invention as an active ingredient, a main ingredient or an auxiliary ingredient and thereby displays the activity of inhibiting the quorum sensing of bacteria and the formation of biofilm as well as the antimicrobial activity.

Therefore, in addition to the dentifrice composition or the gargle composition, any quasi-drug that contains the compound represented by formula 1 or the pharmaceutically acceptable salt thereof of the present invention can be included in the scope of the present invention.

Practical and presently preferred embodiments of the present invention are illustrative as shown in the following examples.

However, it will be appreciated that those skilled in the art, on consideration of this disclosure, may make modifications and improvements within the spirit and scope of the present invention.

EXAMPLE 1

Preparation of 3-(dibromomethylene)-hexahydroisobenzofuran-1(3H)-one

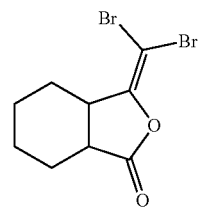 [SMILES: O=C1OC(=C(Br)Br)C2CCCCC12]

Triphenylphosphine (0.79 g, 3.0 mmol) was dissolved in 3 ml of THF, which was cooled down to 0° C. under nitrogen gas. THF (3.0 ml) solution containing $CBr_4$ (0.50 g, 1.5 mmol) dissolved therein was added thereto, followed by stirring until the color of the solution turned yellow. After the color change, TEA (0.27 ml, 1.5 mmol) was added drop by drop for 5 minutes, to which THF (1 ml) solution containing cyclohexanedicarboxylic acid anhydride (0.15 g, 1.0 mmol) dissolved therein was added gradually. The reaction solution was stirred at 0° C. for 30 minutes. Then, the temperature of the reaction solution was adjusted to room temperature, followed by stirring for 3 hours. The reaction was quenched with a saturated $NH_4Cl$ aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.12 g, 40%).

NMR graphs of the obtained target compound are shown in FIG. 1.

The upper graph of FIG. 1 is a graph showing the results of $^1$H NMR of Example 1, and the lower graph of FIG. 1 is a graph showing the results of $^{13}$C NMR of Example 1.

$^1$H NMR (CDCl$_3$, 500 MHz) δ 3.31-3.19 (m, 1H), 2.98 (t, J=6.8 Hz, 1H), 2.22 (t, J=14.3 Hz, 2H), 1.72 (d, J=15.0 Hz, 2H), 1.35-1.05 (m, 4H). $^{13}$C NMR (CDCl$_3$, 125 MHz) δ 174.1, 158.2, 68.9, 40.7, 40.0, 26.5, 23.0, 22.3.

EXAMPLE 2

Preparation of 3-(dibromomethylene)isobenzofuran-1(3H)-one

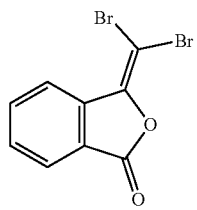 [SMILES: O=C1OC(=C(Br)Br)c2ccccc21]

Triphenylphosphine (1.6 g, 6.0 mmol) was dissolved in 6 ml of THF, which was cooled down to 0° C. under nitrogen gas. THF (6.0 ml) solution containing CBr$_4$ (1.0 g, 3.0 mmol) dissolved therein was added thereto, followed by stirring until the color of the solution turned yellow. After the color change, TEA (1.1 ml, 6.0 mmol) was added drop by drop for 5 minutes, to which THF (1 ml) solution containing phthalic acid anhydride (0.15 g, 1.0 mmol) dissolved therein was added gradually. The reaction solution was stirred at 0° C. for 1 hour. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.091 g, 30%).

Figure 2:
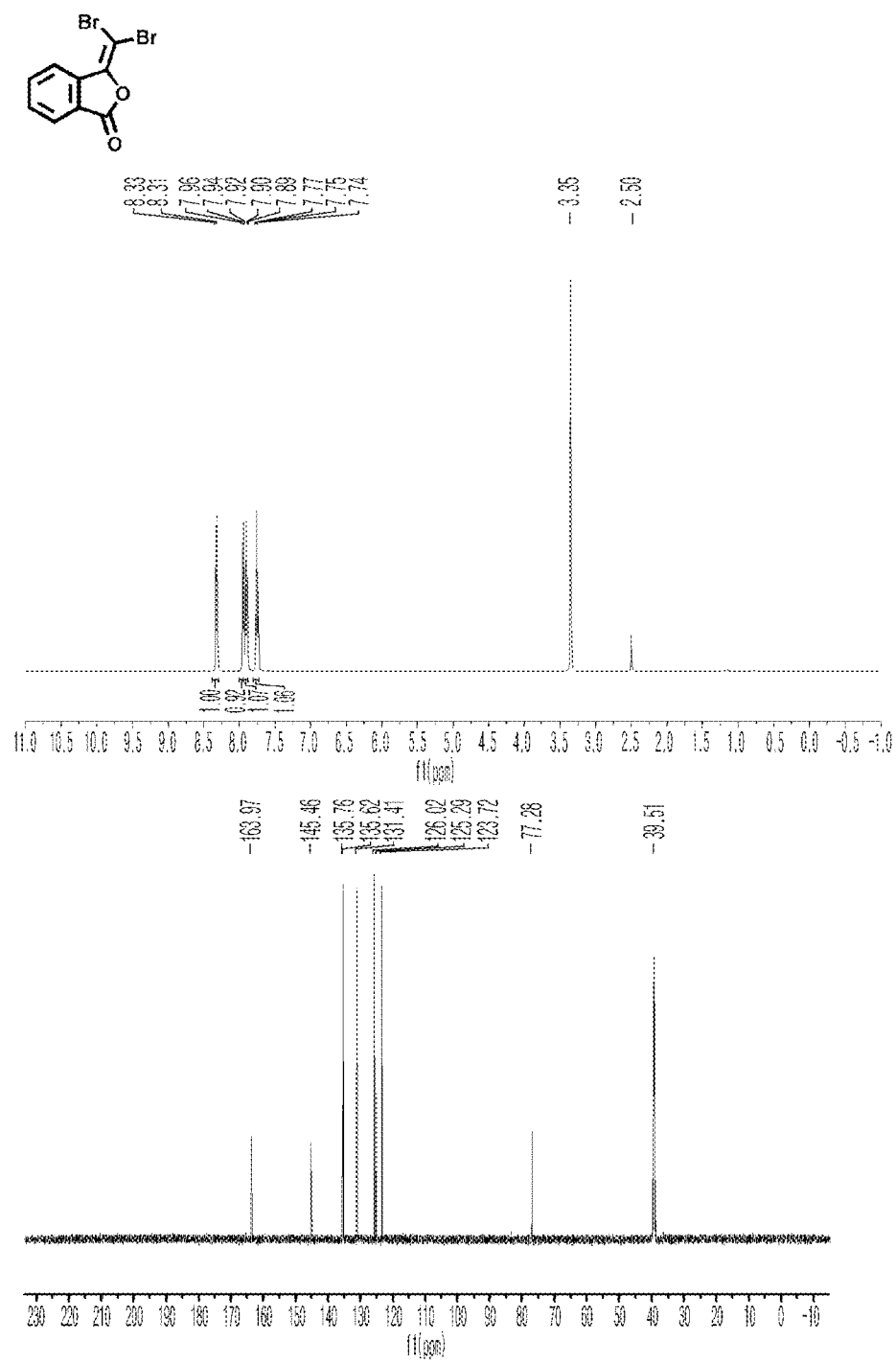
FIG. 2 is a set of graphs illustrating the results of NMR in which the upper graph is a graph showing the results of $^1$H NMR of Example 2, and the lower graph is a graph showing the results of $^{13}$C NMR of Example 2.

NMR graphs of the obtained target compound are shown in FIG. 2.

The upper graph of FIG. 2 is a graph showing the results of $^1$H NMR of Example 2, and the lower graph of FIG. 2 is a graph showing the results of $^{13}$C NMR of Example 2.

$^1$H NMR (DMSO-d$_6$, 500 MHz) δ 8.32 (d, J=8.0 Hz, 1H), 7.95 (d, J=7.6 Hz, 1H), 7.90 (t, J=7.7 Hz, 1H), 7.75 (t, J=7.5 Hz, 1H). $^{13}$C NMR (DMSO-d$_6$, 125 MHz) δ 164.0, 145.5, 135.8, 135.6, 131.4, 126.0, 125.3, 123.7, 77.3.

EXAMPLE 3

Preparation of 3-(dibromomethylene)-4,5,6,7-tetrahydroisobenzofuran-1(3H)-one

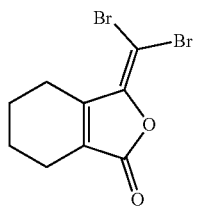 [SMILES: O=C1OC(=C(Br)Br)C2=C1CCCC2]

Triphenylphosphine (1.6 g, 6.0 mmol) was dissolved in 6 ml of THF, which was cooled down to 0° C. under nitrogen gas. THF (6.0 ml) solution containing CBr$_4$ (1.0 g, 3.0 mmol) dissolved therein was added thereto, followed by stirring until the color of the solution turned yellow. After the color change, TEA (1.08 ml, 6.0 mmol) was added drop by drop for 5 minutes, to which THF (1 ml) solution containing 1-cyclohexene dicarboxylic acid anhydride (0.15 g, 1.0 mmol) dissolved therein was added gradually. The reaction solution was stirred at 0° C. for 30 minutes. Then, the temperature of the reaction solution was adjusted to room temperature, followed by stirring for 6 hours. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.20 g, 65%).

Figure 3:
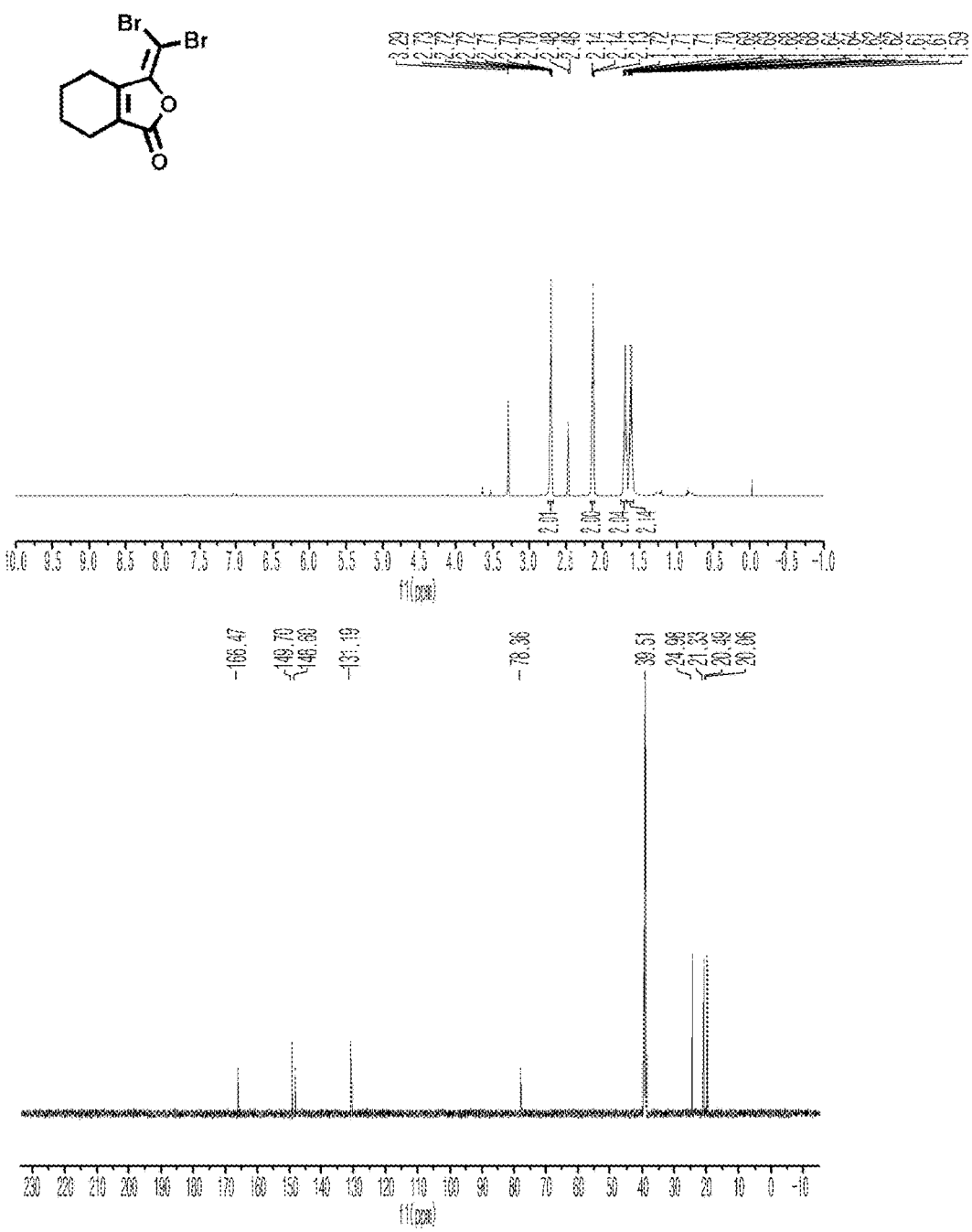
FIG. 3 is a set of graphs illustrating the results of NMR in which the upper graph is a graph showing the results of $^1$H NMR of Example 3, and the lower graph is a graph showing the results of $^{13}$C NMR of Example 3.

NMR graphs of the obtained target compound are shown in FIG. 3.

The upper graph of FIG. 3 is a graph showing the results of $^1$H NMR of Example 3, and the lower graph of FIG. 3 is a graph showing the results of $^{13}$C NMR of Example 3.

$^1$H NMR (DMSO-d$_6$, 500 MHz) δ 2.74-2.69 (m, 2H), 2.16-2.11 (m, 2H), 1.72-1.68 (m, 2H), 1.63-1.59 (m, 2H). $^{13}$C NMR (DMSO-d$_6$, 125 MHz) δ 166.5, 149.7, 148.6, 131.2, 78.4, 25.0, 21.3, 20.5, 20.1.

EXAMPLE 4

3-(dibromomethylene)-5,6-dihydro-3H-cyclopenta[c]furan-1(4H)-one

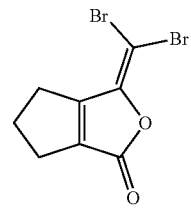 [SMILES: O=C1OC(=C(Br)Br)C2=C1CCC2]

Triphenylphosphine (1.6 g, 6.0 mmol) was dissolved in 6 ml of THF, which was cooled down to 0° C. under nitrogen gas. THF (6.0 ml) solution containing $CBr_4$ (1.0 g, 3.0 mmol) dissolved therein was added thereto, followed by stirring until the color of the solution turned yellow. After the color change, TEA (1.08 ml, 6.0 mmol) was added drop by drop for 5 minutes, to which THF (1 ml) solution containing 1-cyclopentene-1,2-dicarboxylic acid anhydride (0.14 g, 1.0 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated $NH_4Cl$ aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.080 g, 27%).

Figure 4:
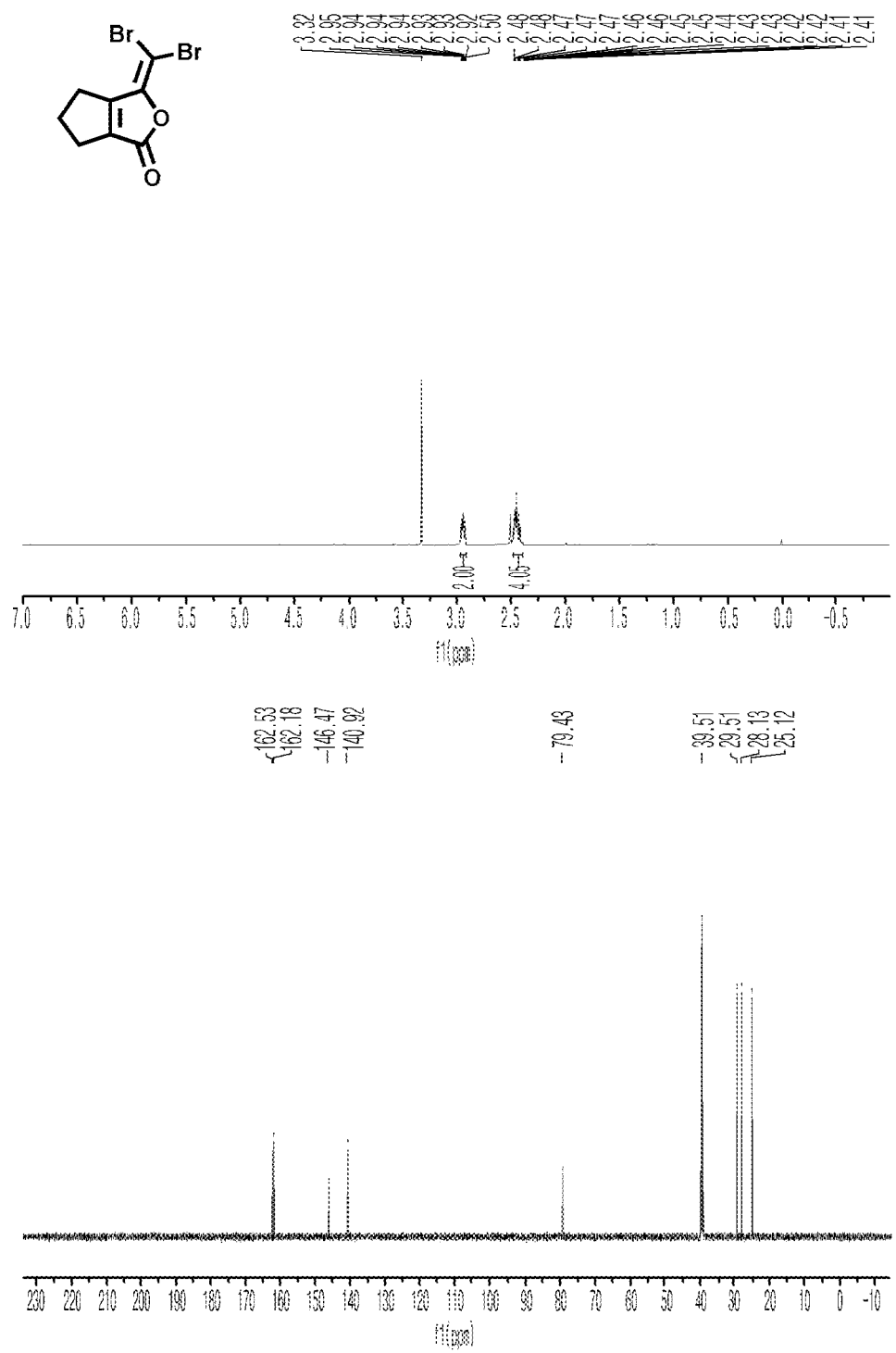
FIG. 4 is a set of graphs illustrating the results of NMR in which the upper graph is a graph showing the results of $^1$H NMR of Example 4, and the lower graph is a graph showing the results of $^{13}$C NMR of Example 4.

NMR graphs of the obtained target compound are shown in FIG. 4.

The upper graph of FIG. 4 is a graph showing the results of $^1$H NMR of Example 4, and the lower graph of FIG. 4 is a graph showing the results of $^{13}$C NMR of Example 4.

$^1$H NMR (DMSO-$d_6$, 500 MHz) δ 2.96-2.91 (m, 2H), 2.48-2.39 (m, 4H). $^{13}$C NMR (DMSO-$d_6$, 125 MHz) δ 162.5, 162.2, 146.5, 140.9, 79.4, 29.5, 28.1, 25.1.

EXAMPLE 5

Preparation of 3-(dibromomethylene)-hexahydrocyclopenta[c]furan-1(3H)-one

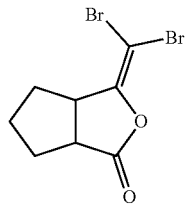 [SMILES: O=C1OC(=C(Br)Br)C2CCCC12]

Triphenylphosphine (1.6 g, 6.0 mmol) was dissolved in 6 ml of THF, which was cooled down to 0° C. under nitrogen gas. THF (6.0 ml) solution containing $CBr_4$ (1.0 g, 3.0 mmol) dissolved therein was added thereto, followed by stirring until the color of the solution turned yellow. After the color change, TEA (1.08 ml, 6.0 mmol) was added drop by drop for 5 minutes, to which THF (1 ml) solution containing cis-1,2-cyclopentane dicarboxylic acid anhydride (0.14 g, 1.0 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated $NH_4Cl$ aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.071 g, 24%).

Figure 5:
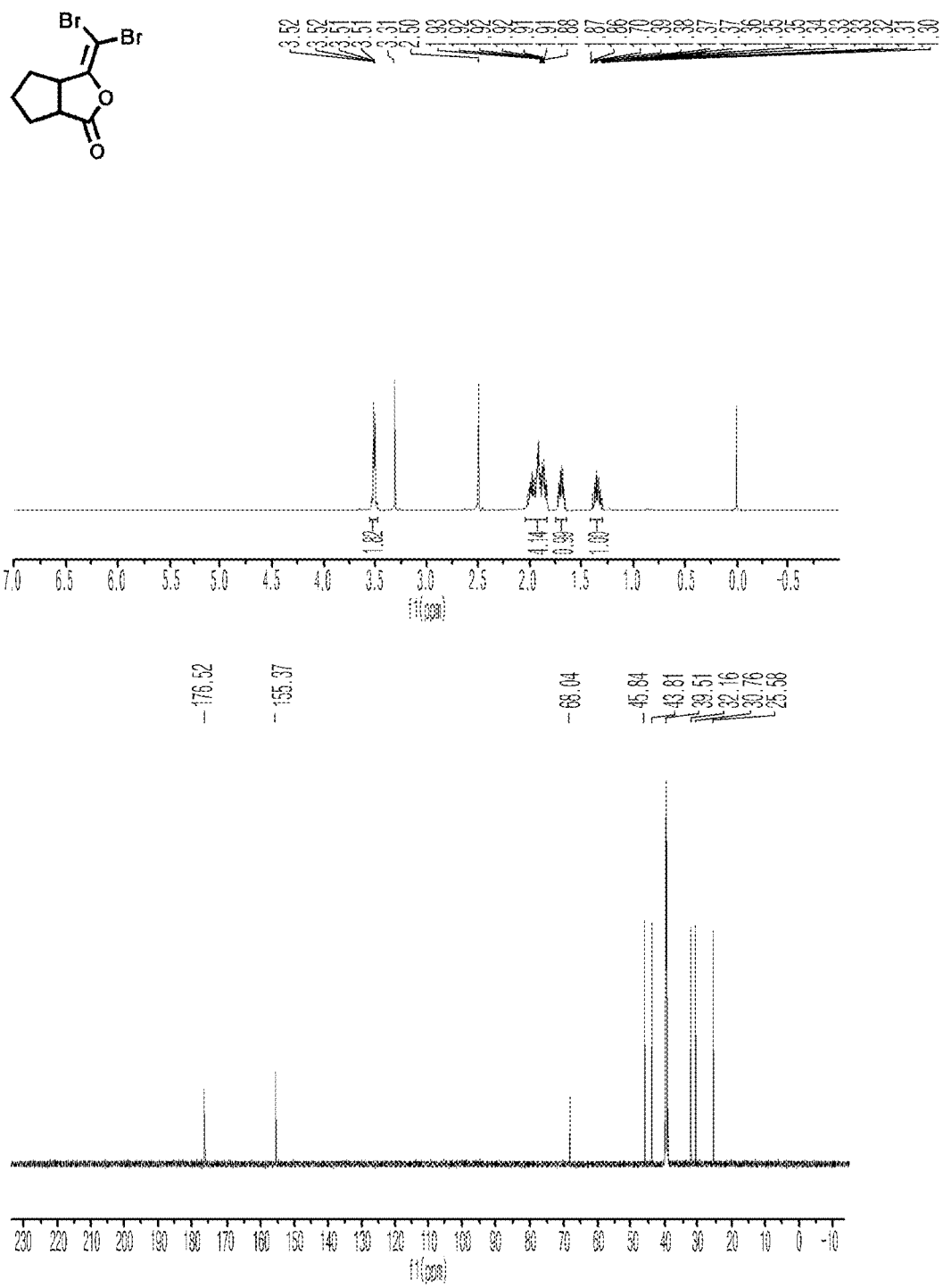
FIG. 5 is a set of graphs illustrating the results of NMR in which the upper graph is a graph showing the results of $^1$H NMR of Example 5, and the lower graph is a graph showing the results of $^{13}$C NMR of Example 5.

NMR graphs of the obtained target compound are shown in FIG. 5.

The upper graph of FIG. 5 is a graph showing the results of $^1$H NMR of Example 5, and the lower graph of FIG. 5 is a graph showing the results of $^{13}$C NMR of Example 5.

$^1$H NMR (DMSO-$d_6$, 500 MHz) δ 3.50-3.48 (m, 2H), 2.04-1.82 (m, 4H), 1.73-1.66 (m, 1H), 1.39-1.30 (m, 1H). $^{13}$C NMR (DMSO-$d_6$, 125 MHz) δ 176.5, 155.4, 68.0, 45.8, 43.8, 32.2, 30.8, 25.6.

EXAMPLE 6

Preparation of 3-(dibromomethylene)-5-methyl-isobenzofuran-1(3H)-one

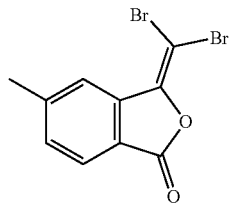

Triphenylphosphine (1.6 g, 6.0 mmol) was dissolved in 6 ml of THF, which was cooled down to 0° C. under nitrogen gas. THF (6.0 ml) solution containing $CBr_4$ (1.0 g, 3.0 mmol) dissolved therein was added thereto, followed by stirring until the color of the solution turned yellow. After the color change, TEA (1.08 ml, 6.0 mmol) was added drop by drop for 5 minutes, to which THF (1 ml) solution containing 4-methylphthalic acid anhydride (0.16 g, 1.0 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated $NH_4Cl$ aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.086 g, 27%).

Figure 6:
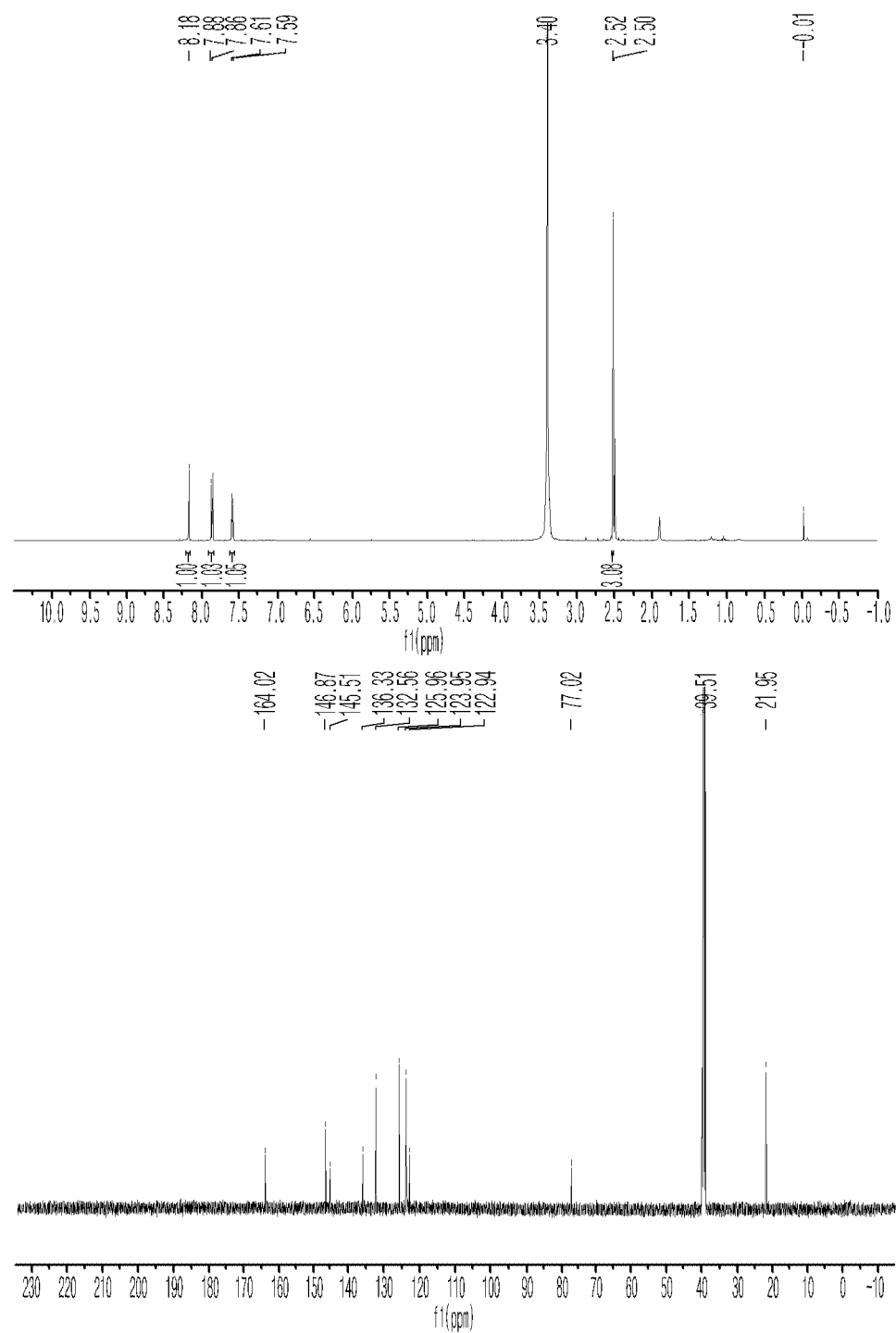
FIG. 6 is a set of graphs illustrating the results of NMR in which the upper graph is a graph showing the results of $^1$H NMR of Example 6, and the lower graph is a graph showing the results of $^{13}$C NMR of Example 6.

NMR graphs of the obtained target compound are shown in FIG. 6.

The upper graph of FIG. 6 is a graph showing the results of $^1$H NMR of Example 6, and the lower graph of FIG. 6 is a graph showing the results of $^{13}$C NMR of Example 6.

$^1$H NMR (DMSO-$d_6$, 500 MHz) δ 8.18 (s, 1H), 7.87 (d, J=7.9 Hz, 1H), 7.60 (d, J=7.8 Hz, 1H), 2.52 (s, 3H). $^{13}$C NMR (DMSO-$d_6$, 125 MHz) δ 164.0, 146.9, 136.3, 132.6, 126.0, 124.0, 122.9, 22.0.

EXAMPLE 7

Preparation of 3-(dibromomethylene)-5-methoxy-isobenzofuran-1(3H)-one

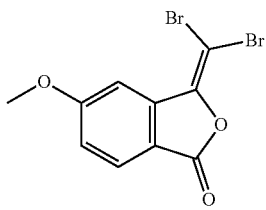

Step 1: Preparation of dimethyl 4-hydroxyphthalate

4-Hydroxyphthalic acid (1.09 g, 6.0 mmol) was dissolved in 12 ml of methanol. $H_2SO_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over $MgSO_4$, and the solvent was eliminated under reduced pressure. As a result, a crude target compound was obtained (1.20 g, 95%).

$^1$H NMR (DMSO-$d_6$, 500 MHz) δ 10.61 (s, 1H), 7.70 (d, J=8.4 Hz, 1H), 6.97 (dd, J=8.4, 2.5 Hz, 1H), 6.95 (d, J=2.3 Hz, 1H), 3.79 (s, 3H), 3.76 (s, 3H). $^{13}$C NMR (DMSO-$d_6$, 125 MHz) δ 168.3, 166.2, 160.8, 135.8, 131.7, 119.8, 117.1, 114.8, 52.5, 52.1.

Step 2: Preparation of dimethyl 4-methoxyphthalate

The compound prepared in step 1 above (0.4 g, 1.9 mmol) was dissolved in 3 ml of acetone, followed by stirring in the presence of $K_2CO_3$ (1.3 g, 9.5 mmol) at room temperature for 1 hour. Iodomethane (0.35 ml, 5.7 mmol) was added thereto, followed by stirring under reflux for overnight. The reaction mixture was filtered to remove $K_2CO_3$ and the solvent was eliminated under reduced pressure. After evaporating the solvent, the obtained product was purified by flash column chromatography. As a result, a target compound was obtained (0.35 g, 83%).

$^1$H NMR (DMSO-$d_6$, 500 MHz) δ 7.79 (d, J=9.1 Hz, 1H), 7.15 (dd, J=7.4, 2.4 Hz, 2H), 3.85 (s, 3H), 3.81 (s, 3H), 3.79 (s, 3H). $^{13}$C NMR (DMSO-$d_6$, 125 MHz) δ 167.9, 166.0, 161.8, 135.5, 131.4, 121.4, 115.9, 113.4, 55.8, 52.5, 52.3.

Step 3: Preparation of 4-methoxyphthalic acid

The 3 ml of acetone containing the compound prepared in step 2 (0.31 g, 1.4 mmol) dissolved therein was treated with 2 ml of water containing NaOH (0.34 g, 8.4 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over $MgSO_4$, and the solvent was eliminated under reduced pressure. As a result, a crude target compound was obtained (0.27 g, 97%).

$^1$H NMR (DMSO-$d_6$, 500 MHz) δ 12.94 (s, 2H), 7.74 (d, J=8.5 Hz, 1H), 7.07 (dd, J=8.5, 2.7 Hz, 1H), 7.05 (d, J=2.5 Hz, 1H), 3.83 (s, 3H). $^{13}$C NMR (DMSO-$d_6$, 125 MHz) δ 169.3, 167.4, 161.4, 137.1, 131.3, 122.7, 115.1, 113.0, 55.7.

Step 4: Preparation of 5-methoxyisobenzofuran-1,3-dione

The compound prepared in step 3 above (0.23 g, 1.2 mmol) was dissolved in 4 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.21 g, 98%).

$^1$H NMR (DMSO-$d_6$, 500 MHz) δ 7.99 (d, J=8.4 Hz, 1H), 7.58 (d, J=2.3 Hz, 1H), 7.48 (dd, J=8.5, 2.3 Hz, 1H), 3.97 (s, 3H). $^{13}$C NMR (DMSO-$d_6$, 125 MHz) δ 165.7, 163.1, 162.7, 134.0, 127.2, 122.9, 122.7, 109.3, 56.7.

Step 5: Preparation of 3-(dibromomethylene)-5-methoxyisobenzofuran-1(3H)-one Triphenylphosphine (1.3 g, 5.1 mmol) was dissolved in 6 ml of THF, which was cooled down to 0° C. under nitrogen gas. THF (5.0 ml) solution containing $CBr_4$ (0.84 g, 2.5 mmol) dissolved therein was added thereto, followed by stirring until the color of the solution turned yellow. After the color change, TEA (0.91 ml, 5.1 mmol) was added drop by drop for 5 minutes, to which THF (1 ml) solution containing the compound prepared in step 4 above (0.15 g, 0.85 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated $NH_4Cl$ aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.077 g, 27%).

Figure 7:
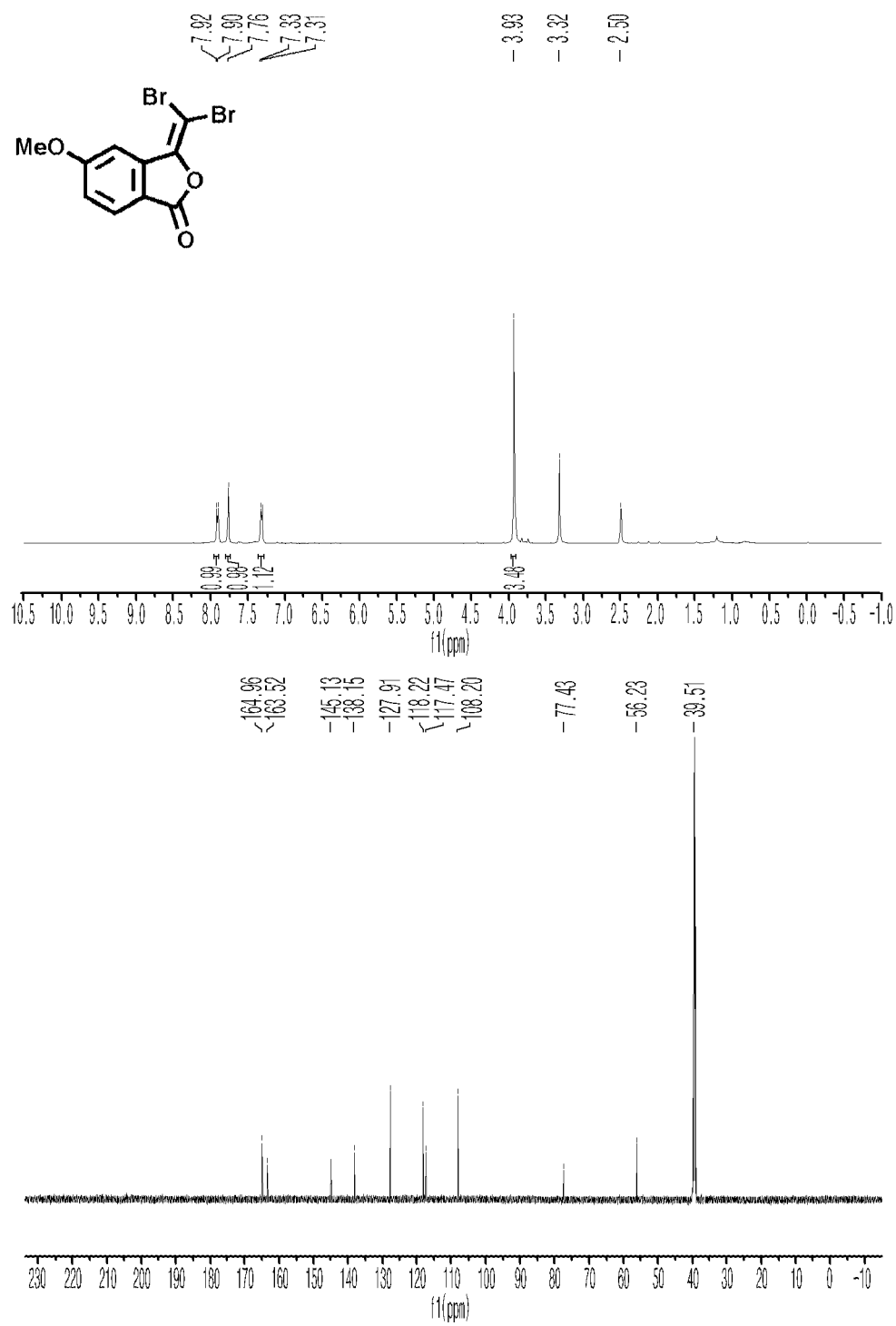
FIG. 7 is a set of graphs illustrating the results of NMR in which the upper graph is a graph showing the results of $^1$H NMR of Example 7, and the lower graph is a graph showing the results of $^{13}$C NMR of Example 7.

NMR graphs of the obtained target compound are shown in FIG. 7.

The upper graph of FIG. 7 is a graph showing the results of $^1$H NMR of Example 7, and the lower graph of FIG. 7 is a graph showing the results of $^{13}$C NMR of Example 7.

$^1$H NMR (DMSO-$d_6$, 500 MHz) δ 7.91 (d, J=8.5 Hz, 1H), 7.76 (s, 1H), 7.32 (d, J=7.0 Hz, 1H), 3.93 (s, 3H). $^{13}$C NMR (DMSO-$d_6$, 125 MHz) δ 165.0, 163.5, 145.1, 138.2, 127.9, 118.2, 117.5, 108.2, 77.4, 56.2.

EXAMPLE 8

Preparation of 3-(dibromomethylene)-5-ethoxy-isobenzofuran-1(3H)-one

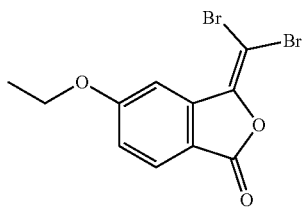 [SMILES: CCOc1ccc2c(c1)C(=C(Br)Br)OC2=O]

Step 1: Preparation of dimethyl 4-hydroxyphthalate

4-Hydroxyphthalic acid (1.09 g, 6.0 mmol) was dissolved in 12 ml of methanol. H$_2$SO$_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over MgSO$_4$, and the solvent was eliminated under reduced pressure. As a result, a crude target compound was obtained (1.20 g, 95%).

$^1$H NMR (DMSO-d$_6$, 500 MHz) δ 10.61 (s, 1H), 7.70 (d, J=8.4 Hz, 1H), 6.97 (dd, J=8.4, 2.5 Hz, 1H), 6.95 (d, J=2.3 Hz, 1H), 3.79 (s, 3H), 3.76 (s, 3H). $^{13}$C NMR (DMSO-d$_6$, 125 MHz) δ 168.3, 166.2, 160.8, 135.8, 131.7, 119.8, 117.1, 114.8, 52.5, 52.1.

Step 2: Preparation of dimethyl 4-ethoxyphthalate

The compound prepared in step 1 above (0.47 g, 2.3 mmol) was dissolved in 4 ml of acetone, followed by stirring in the presence of K$_2$CO$_3$ (1.6 g, 11.3 mmol) at room temperature for 1 hour. Iodoethane (0.54 ml, 6.8 mmol) was added thereto, followed by stirring under reflux for overnight.

The reaction mixture was filtered to remove K$_2$CO$_3$ and the solvent was eliminated under reduced pressure. After evaporating the solvent, the obtained product was purified by flash column chromatography. As a result, a target compound was obtained (0.44 g, 81%).

$^1$H NMR (DMSO-d$_6$, 500 MHz) δ 7.77 (d, J=8.3 Hz, 1H), 7.14-7.10 (m, 2H), 4.11 (q, J=6.9 Hz, 2H), 3.80 (s, 3H), 3.78 (s, 3H), 1.33 (t, J=7.0 Hz, 3H). $^{13}$C NMR (DMSO-d$_6$, 125 MHz) δ 167.9, 166.0, 161.1, 135.5, 131.4, 121.2, 116.2, 113.8, 63.9, 52.5, 52.2, 14.3.

Step 3: Preparation of 4-ethoxyphthalic acid

The 3 ml of acetone containing the compound prepared in step 2 (0.36 g, 1.5 mmol) dissolved therein was treated with 2 ml of water containing NaOH (0.36 g, 9.0 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over MgSO$_4$, and the solvent was eliminated under reduced pressure. As a result, a crude target compound was obtained (0.31 g, 97%).

$^1$H NMR (DMSO-d$_6$, 500 MHz) δ 12.92 (s, 2H), 7.72 (d, J=8.6 Hz, 1H), 7.05 (dd, J=8.6, 2.6 Hz, 1H), 7.02 (d, J=2.6 Hz, 1H), 4.11 (q, J=7.0 Hz, 2H), 1.33 (t, J=7.0 Hz, 3H). $^{13}$C NMR (DMSO-d$_6$, 125 MHz) δ 169.2, 167.3, 160.6, 137.1, 131.2, 122.5, 115.4, 113.4, 63.7, 14.4.

Step 4: Preparation of 5-ethoxyisobenzofuran-1,3-dione

The compound prepared in step 3 above (0.36 g, 1.7 mmol) was dissolved in 5 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.32 g, 97%).

$^1$H NMR (DMSO-d$_6$, 500 MHz) δ 7.96 (d, J=8.4 Hz, 1H), 7.53 (d, J=2.3 Hz, 1H), 7.45 (dd, J=8.4, 2.3 Hz, 1H), 4.25 (q, J=7.0 Hz, 2H), 1.37 (t, J=7.0 Hz, 3H). $^{13}$C NMR (DMSO-d$_6$, 125 MHz) δ 164.92, 163.1, 162.6, 134.0, 127.2, 123.1, 122.5, 109.6, 64.9, 14.3.

Step 5: Preparation of 3-(dibromomethylene)-5-ethoxyisobenzofuran-1(3H)-one

Triphenylphosphine (1.4 g, 5.2 mmol) was dissolved in 4.5 ml of THF, which was cooled down to 0° C. under nitrogen gas. THF (5.0 ml) solution containing CBr$_4$ (0.87 g, 2.6 mmol) dissolved therein was added thereto, followed by stirring until the color of the solution turned yellow. After the color change, TEA (0.94 ml, 5.2 mmol) was added drop by drop for 5 minutes, to which THF (1 ml) solution containing the compound prepared in step 4 above (0.17 g, 0.87 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.076 g, 25%).

Figure 8:
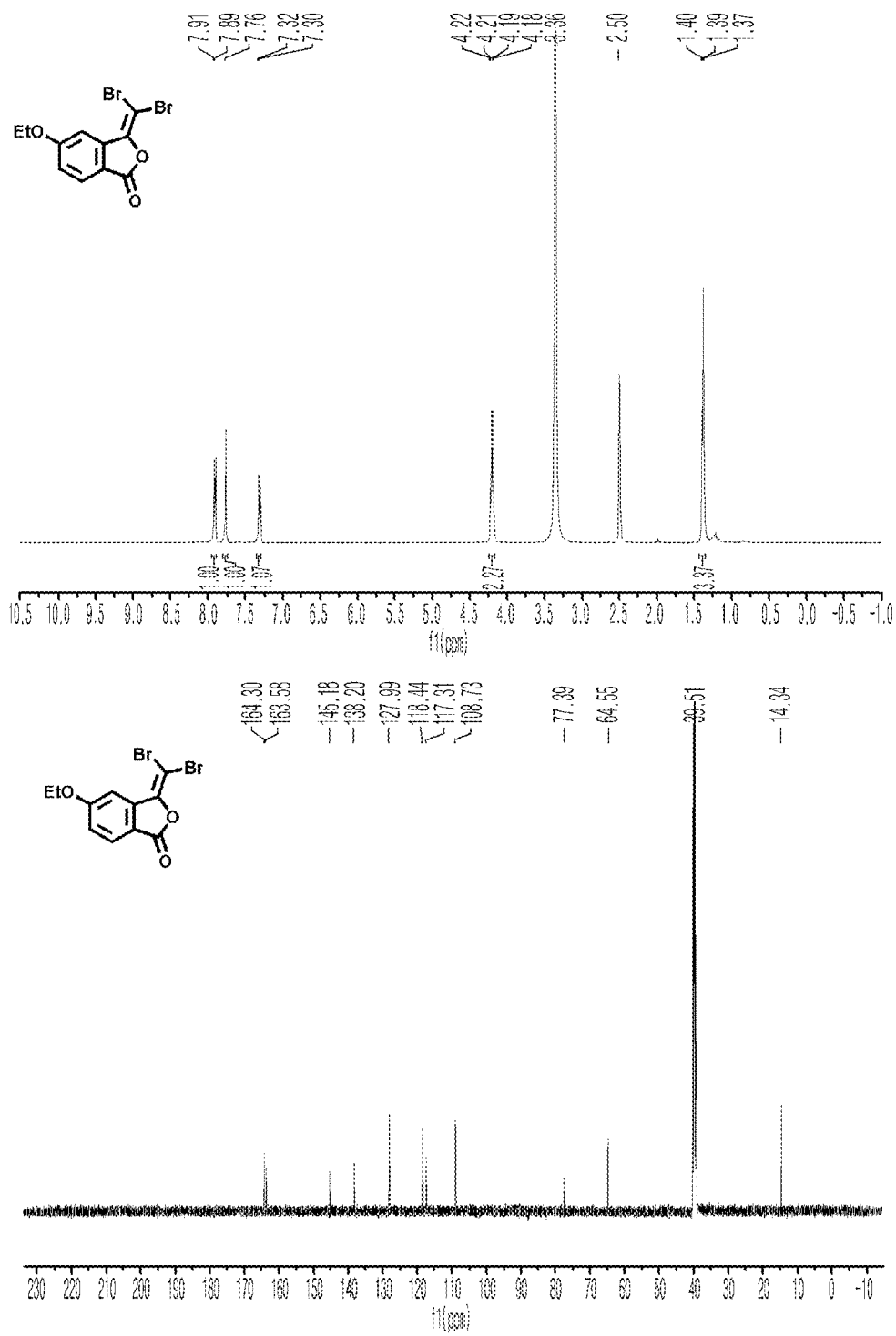
FIG. 8 is a set of graphs illustrating the results of NMR in which the upper graph is a graph showing the results of $^1$H NMR of Example 8, and the lower graph is a graph showing the results of $^{13}$C NMR of Example 8.

NMR graphs of the obtained target compound are shown in FIG. 8.

The upper graph of FIG. 8 is a graph showing the results of $^1$H NMR of Example 8, and the lower graph of FIG. 8 is a graph showing the results of $^{13}$C NMR of Example 8.

$^1$H NMR (DMSO-d$_6$, 500 MHz) δ 7.90 (d, J=8.5 Hz, 1H), 7.76 (s, 1H), 7.31 (d, J=7.0 Hz, 1H), 4.20 (q, J=6.8 Hz, 2H), 1.39 (t, J=6.9 Hz, 3H). $^{13}$C NMR (DMSO-d$_6$, 125 MHz) δ 164.3, 163.6, 145.2, 138.2, 128.0, 118.4, 117.3, 108.7, 77.4, 64.6, 14.3.

EXAMPLE 9

Preparation of 3-(dibromomethylene)-5-propoxy-isobenzofuran-1(3H)-one

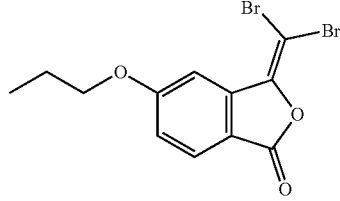 [SMILES: CCCOc1ccc2c(c1)C(=C(Br)Br)OC2=O]

Step 1: Preparation of dimethyl 4-hydroxyphthalate

4-Hydroxyphthalic acid (1.09 g, 6.0 mmol) was dissolved in 12 ml of methanol. H$_2$SO$_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over MgSO$_4$, and the solvent was eliminated under reduced pressure. As a result, a crude target compound was obtained (1.20 g, 95%).

$^1$H NMR (DMSO-$d_6$, 500 MHz) δ 10.61 (s, 1H), 7.70 (d, J=8.4 Hz, 1H), 6.97 (dd, J=8.4, 2.5 Hz, 1H), 6.95 (d, J=2.3 Hz, 1H), 3.79 (s, 3H), 3.76 (s, 3H). $^{13}$C NMR (DMSO-$d_6$, 125 MHz) δ 168.3, 166.2, 160.8, 135.8, 131.7, 119.8, 117.1, 114.8, 52.5, 52.1.

Step 2: Preparation of dimethyl 4-propoxyphthalate

The compound prepared in step 1 above (0.44 g, 2.1 mmol) was dissolved in 4 ml of acetone, followed by stirring in the presence of K$_2$CO$_3$ (1.5 g, 10.7 mmol) at room temperature for 1 hour. Iodopropane (0.62 ml, 6.4 mmol) was added thereto, followed by stirring under reflux for overnight. The reaction mixture was filtered to remove K$_2$CO$_3$ and the solvent was eliminated under reduced pressure. After evaporating the solvent, the obtained product was purified by flash column chromatography. As a result, a target compound was obtained (0.43 g, 81%).

$^1$H NMR (DMSO-$d_6$, 500 MHz) δ 7.77 (d, J=9.0 Hz, 1H), 7.15-7.11 (m, 2H), 4.01 (t, J=6.5 Hz, 2H), 3.81 (s, 3H), 3.78 (s, 3H), 1.79-1.66 (m, 2H), 0.96 (t, J=7.4 Hz, 3H). $^{13}$C NMR (DMSO-$d_6$, 125 MHz) δ 167.9, 166.0, 161.3, 135.5, 131.4, 121.2, 116.2, 113.8, 69.6, 52.5, 52.2, 21.8, 10.1.

Step 3: Preparation of 4-propoxyphthalic acid

The 3 ml of acetone containing the compound prepared in step 2 (0.42 g, 1.7 mmol) dissolved therein was treated with 2 ml of water containing NaOH (0.40 g, 10.0 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over MgSO$_4$, and concentrated under reduced pressure. As a result, a crude target compound was obtained (0.35 g, 96%).

$^1$H NMR (DMSO-$d_6$, 500 MHz) δ 12.92 (s, 2H), 7.72 (d, J=8.6 Hz, 1H), 7.06 (dd, J=8.6, 2.6 Hz, 1H), 7.03 (d, J=2.6 Hz, 1H), 4.01 (t, J=6.5 Hz, 2H), 1.74 (m, 2H), 0.97 (t, J=7.4 Hz, 3H). $^{13}$C NMR (DMSO-$d_6$, 125 MHz) δ 169.2, 167.3, 160.8, 137.1, 131.3, 122.5, 115.4, 113.4, 69.5, 21.9, 10.3.

Step 4: Preparation of 5-propoxyisobenzofuran-1,3-dione

The compound prepared in step 3 above (0.25 g, 1.1 mmol) was dissolved in 4 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.22 g, 94%).

$^1$H NMR (DMSO-$d_6$, 500 MHz) δ 7.97 (d, J=8.4 Hz, 1H), 7.55 (d, J=2.2 Hz, 1H), 7.47 (dd, J=8.4, 2.3 Hz, 1H), 4.16 (t, J=6.5 Hz, 2H), 1.81-1.72 (m, 2H), 0.99 (t, J=7.4 Hz, 3H). $^{13}$C NMR (DMSO-$d_6$, 125 MHz) δ 165.1, 163.1, 162.7, 134.0, 127.2, 123.1, 122.5, 109.6, 70.5, 21.7, 10.2.

Step 5: Preparation of 3-(dibromomethylene)-5-propoxyisobenzofuran-1(3H)-one

Triphenylphosphine (0.94 g, 3.6 mmol) was dissolved in 4 ml of THF, which was cooled down to 0° C. under nitrogen gas. THF (5.0 ml) solution containing CBr$_4$ (0.60 g, 1.8 mmol) dissolved therein was added thereto, followed by stirring until the color of the solution turned yellow. After the color change, TEA (0.65 ml, 3.6 mmol) was added drop by drop for 5 minutes, to which THF (1 ml) solution containing the compound prepared in step 4 above (0.12 g, 0.6 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.045 g, 21%).

Figure 9:
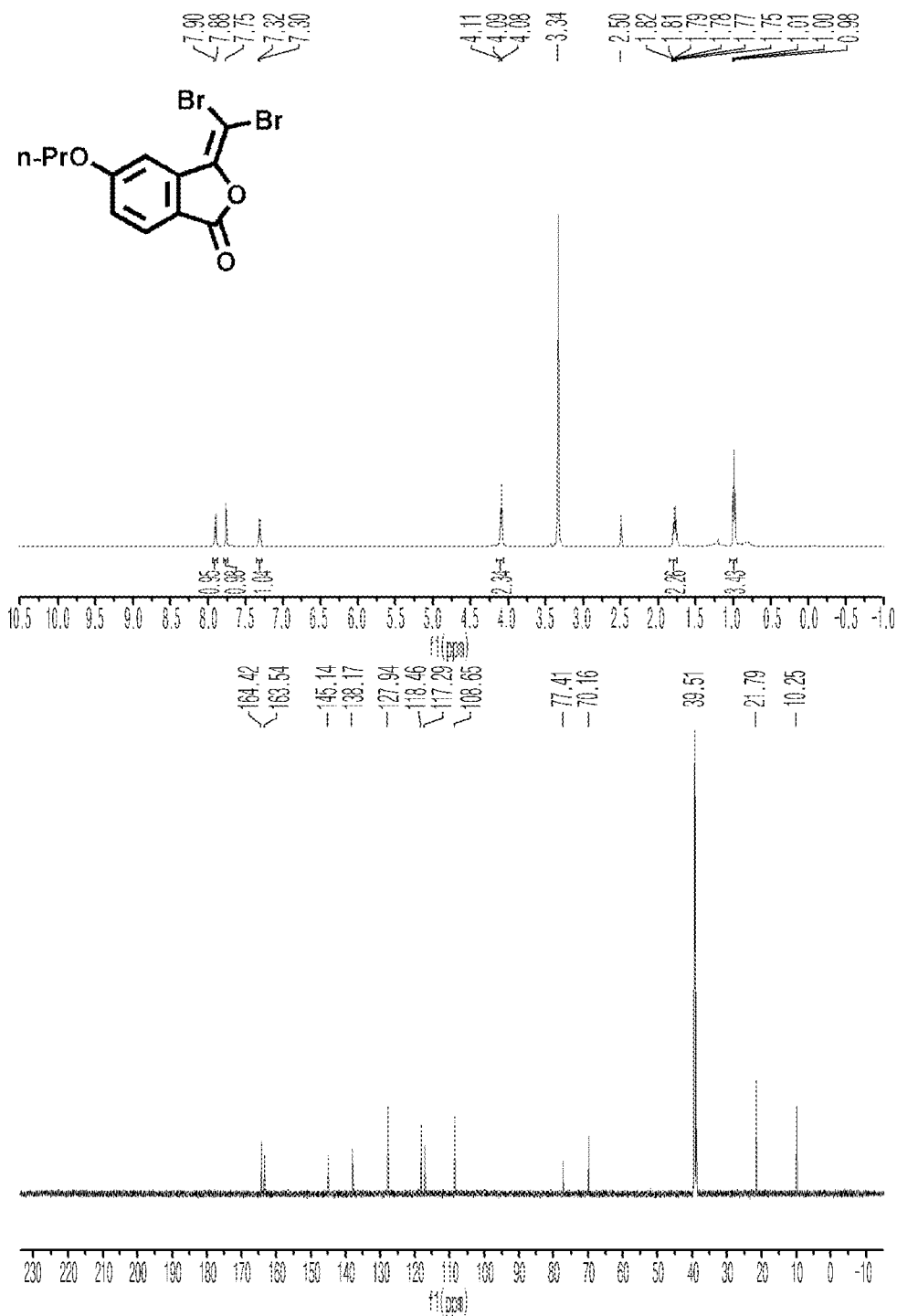
FIG. 9 is a set of graphs illustrating the results of NMR in which the upper graph is a graph showing the results of $^1$H NMR of Example 9, and the lower graph is a graph showing the results of $^{13}$C NMR of Example 9.

NMR graphs of the obtained target compound are shown in FIG. 9.

The upper graph of FIG. 9 is a graph showing the results of $^1$H NMR of Example 9, and the lower graph of FIG. 9 is a graph showing the results of $^{13}$C NMR of Example 9.

$^1$H NMR (DMSO-$d_6$, 500 MHz) δ 7.89 (d, J=8.5 Hz, 1H), 7.75 (s, 1H), 7.31 (d, J=8.5 Hz, 1H), 4.09 (t, J=6.4 Hz, 2H), 1.84-1.75 (m, 2H), 1.00 (t, J=7.4 Hz, 3H). $^{13}$C NMR (DMSO-$d_6$, 125 MHz) δ 164.4, 163.5, 145.1, 138.1, 127.9, 118.5, 117.3, 108.7, 77.4, 70.2, 21.8, 10.3.

EXAMPLE 10

Preparation of 5-butoxy-3-(dibromomethylene)isobenzofuran-1(3H)-one

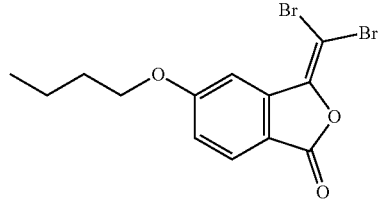 [SMILES: CCCCOc1ccc2c(c1)C(=C(Br)Br)OC2=O]

Step 1: Preparation of dimethyl 4-hydroxyphthalate

4-Hydroxyphthalic acid (1.09 g, 6.0 mmol) was dissolved in 12 ml of methanol. H$_2$SO$_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over MgSO$_4$, and the solvent was eliminated under reduced pressure. As a result, a crude target compound was obtained (1.20 g, 95%).

$^1$H NMR (DMSO-$d_6$, 500 MHz) δ 10.61 (s, 1H), 7.70 (d, J=8.4 Hz, 1H), 6.97 (dd, J=8.4, 2.5 Hz, 1H), 6.95 (d, J=2.3 Hz, 1H), 3.79 (s, 3H), 3.76 (s, 3H). $^{13}$C NMR (DMSO-$d_6$, 125 MHz) δ 168.3, 166.2, 160.8, 135.8, 131.7, 119.8, 117.1, 114.8, 52.5, 52.1.

Step 2: Preparation of dimethyl 4-butoxyphthalate

The compound prepared in step 1 above (0.28 g, 1.3 mmol) was dissolved in 3 ml of acetone, followed by stirring in the presence of K$_2$CO$_3$ (0.93 g, 6.7 mmol) at room temperature for 1 hour. Iodobutane (0.46 ml, 4.03 mmol)

was added thereto, followed by stirring under reflux for overnight. The reaction mixture was filtered to remove $K_2CO_3$ and the solvent was eliminated under reduced pressure. After evaporating the solvent, the obtained product was purified by flash column chromatography. As a result, a target compound was obtained (0.30 g, 84%).

$^1$H NMR (DMSO-$d_6$, 500 MHz) δ 7.77 (d, J=8.4 Hz, 1H), 7.15-7.12 (m, 2H), 4.06 (t, J=6.5 Hz, 2H), 3.80 (s, 3H), 3.78 (s, 3H), 1.75-1.65 (m, 2H), 1.46-1.37 (m, 2H), 0.92 (t, J=7.4 Hz, 3H). $^{13}$C NMR (DMSO-$d_6$, 125 MHz) δ 167.9, 166.0, 161.3, 135.5, 131.4, 121.2, 116.2, 113.8, 67.9, 52.5, 52.2, 30.4, 18.6, 13.5.

Step 3: Preparation of 4-butoxyphthalic acid

The 2 ml of acetone containing the compound prepared in step 2 (0.27 g, 1.0 mmol) dissolved therein was treated with 2 ml of water containing NaOH (0.24 g, 6.1 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over $MgSO_4$, and concentrated under reduced pressure. As a result, a crude target compound was obtained (0.23 g, 97%).

$^1$H NMR (DMSO-$d_6$, 500 MHz) δ 12.89 (s, 2H), 7.72 (d, J=8.6 Hz, 1H), 7.08-6.97 (m, 2H), 4.04 (t, J=6.5 Hz, 2H), 1.74-1.66 (m, 2H), 1.46-1.35 (m, 2H), 0.92 (t, J=7.4 Hz, 3H). $^{13}$C NMR (DMSO-$d_6$, 125 MHz) δ 169.2, 167.4, 160.9, 137.1, 131.3, 122.5, 115.4, 113.5, 67.8, 30.6, 18.7, 13.7.

Step 4: Preparation of 5-butoxyisobenzofuran-1,3-dione

The compound prepared in step 3 above (0.22 g, 0.92 mmol) was dissolved in 4 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.19 g, 95%).

$^1$H NMR (DMSO-$d_6$, 500 MHz) δ 7.97 (d, J=8.4 Hz, 1H), 7.56 (d, J=2.3 Hz, 1H), 7.47 (dd, J=8.5, 2.2 Hz, 1H), 4.20 (t, J=6.5 Hz, 2H), 1.79-1.68 (m, 2H), 1.51-1.38 (m, 2H), 0.94 (t, J=7.4 Hz, 3H). $^{13}$C NMR (DMSO-$d_6$, 125 MHz) δ 165.1, 163.1, 162.7, 134.0, 127.2, 123.2, 122.5, 109.6, 68.8, 30.3, 18.6, 13.6.

Step 5: Preparation of 5-butoxy-3-(dibromomethylene)isobenzofuran-1(3H)-one

Triphenylphosphine (1.15 g, 4.4 mmol) was dissolved in 5 ml of THF, which was cooled down to 0° C. under nitrogen gas. THF (5.0 ml) solution containing $CBr_4$ (0.73 g, 2.2 mmol) dissolved therein was added thereto, followed by stirring until the color of the solution turned yellow. After the color change, TEA (0.79 ml, 4.4 mmol) was added drop by drop for 5 minutes, to which THF (1 ml) solution containing the compound prepared in step 4 above (0.16 g, 0.73 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated $NH_4Cl$ aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.066 g, 24%).

Figure 10:
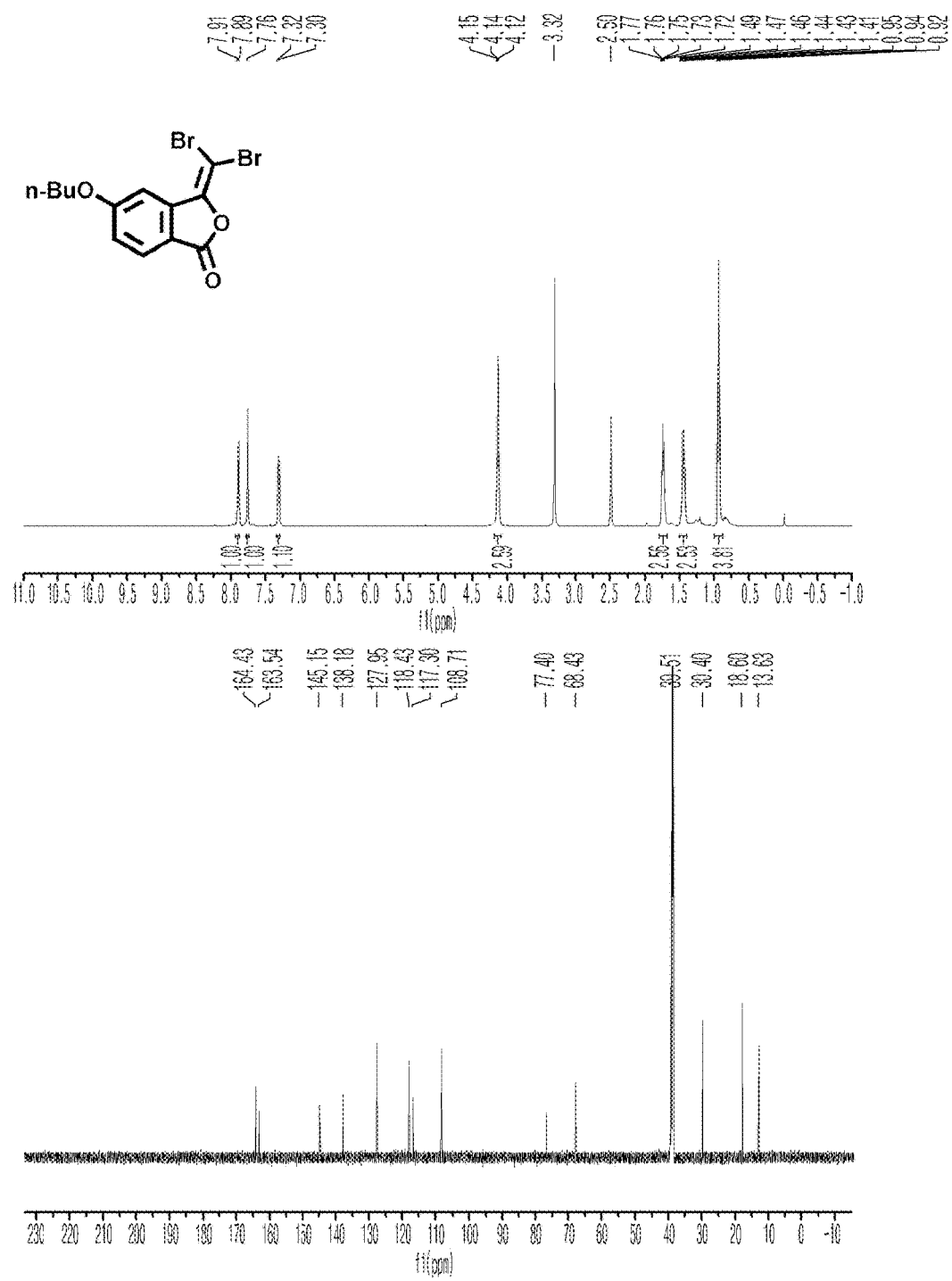
FIG. 10 is a set of graphs illustrating the results of NMR in which the upper graph is a graph showing the results of $^1$H NMR of Example 10, and the lower graph is a graph showing the results of $^{13}$C NMR of Example 10.

NMR graphs of the obtained target compound are shown in FIG. 10.

The upper graph of FIG. 10 is a graph showing the results of $^1$H NMR of Example 10, and the lower graph of FIG. 10 is a graph showing the results of $^{13}$C NMR of Example 10.

$^1$H NMR (DMSO-$d_6$, 500 MHz) δ 7.90 (d, J=8.5 Hz, 1H), 7.76 (s, 1H), 7.31 (d, J=8.5 Hz, 1H), 4.14 (t, J=6.4 Hz, 2H), 1.80-1.68 (m, 2H), 1.50-1.39 (m, 2H), 0.94 (t, J=7.4 Hz, 3H). $^{13}$C NMR (DMSO-$d_6$, 125 MHz) δ 164.4, 163.5, 145.2, 138.2, 128.0, 118.4, 117.3, 108.7, 77.4, 68.4, 39.5, 30.4, 18.6, 13.6.

EXAMPLE 11

Preparation of 3-(dibromomethylene)-5-(pentyloxy)isobenzofuran-1(3H)-one

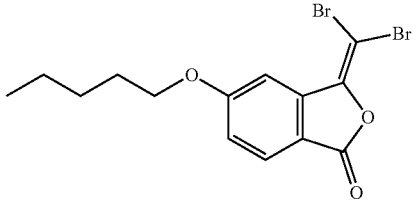 [SMILES: CCCCCOc1ccc2c(c1)C(=C(Br)Br)OC2=O]

Step 1: Preparation of dimethyl 4-hydroxyphthalate

4-Hydroxyphthalic acid (1.09 g, 6.0 mmol) was dissolved in 12 ml of methanol. $H_2SO_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over $MgSO_4$, and the solvent was eliminated under reduced pressure. As a result, a crude target compound was obtained (1.20 g, 95%).

$^1$H NMR (DMSO-$d_6$, 500 MHz) δ 10.61 (s, 1H), 7.70 (d, J=8.4 Hz, 1H), 6.97 (dd, J=8.4, 2.5 Hz, 1H), 6.95 (d, J=2.3 Hz, 1H), 3.79 (s, 3H), 3.76 (s, 3H). $^{13}$C NMR (DMSO-$d_6$, 125 MHz) δ 168.3, 166.2, 160.8, 135.8, 131.7, 119.8, 117.1, 114.8, 52.5, 52.1.

Step 2: Preparation of dimethyl 4-pentyloxyphthalate

The compound prepared in step 1 above (0.16 g, 0.76 mmol) was dissolved in 3 ml of acetone, followed by stirring in the presence of $K_2CO_3$ (0.53 g, 3.8 mmol) at room temperature for 1 hour. Iodopentane (0.30 ml, 2.3 mmol) was added thereto, followed by stirring under reflux for overnight. The reaction mixture was filtered to remove $K_2CO_3$ and the solvent was eliminated under reduced pressure. After evaporating the solvent, the obtained product was purified by flash column chromatography. As a result, a target compound was obtained (0.17 g, 82%).

$^1$H NMR (DMSO-$d_6$, 500 MHz) δ 7.77 (d, J=9.4 Hz, 1H), 7.14-7.10 (m, 2H), 4.03 (t, J=6.5 Hz, 2H), 3.81 (s, 3H), 3.78

(s, 3H), 1.74-1.66 (m, 2H), 1.40-1.27 (m, 4H), 0.87 (t, J=7.1 Hz, 3H). $^{13}$C NMR (DMSO-d$_6$, 125 MHz) δ 167.9, 166.0, 161.3, 135.5, 131.4, 121.2, 116.1, 113.8, 68.2, 52.5, 52.2, 28.1, 27.5, 21.8, 13.7.

Step 3: Preparation of 4-pentyloxyphthalic acid

The 2 ml of acetone containing the compound prepared in step 2 (0.16 g, 0.57 mmol) dissolved therein was treated with 1 ml of water containing NaOH (0.14 g, 3.4 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over MgSO$_4$, and concentrated under reduced pressure. As a result, a crude target compound was obtained (0.14 g, 96%).

$^1$H NMR (DMSO-d$_6$, 500 MHz) δ 12.91 (s, 2H), 7.72 (d, J=8.6 Hz, 1H), 7.05 (dd, J=8.6, 2.6 Hz, 1H), 7.02 (d, J=2.5 Hz, 1H), 4.03 (t, J=6.5 Hz, 2H), 1.76-1.67 (m, 2H), 1.44-1.29 (m, 4H), 0.88 (t, J=7.1 Hz, 3H). $^{13}$C NMR (DMSO-d$_6$, 125 MHz) δ 169.2, 167.4, 160.9, 137.1, 131.3, 122.4, 115.4, 113.4, 68.1, 28.2, 27.6, 21.9, 13.9.

Step 4: Preparation of 5-pentyloxyisobenzofuran-1,3-dione

The compound prepared in step 3 above (0.14 g, 0.56 mmol) was dissolved in 3 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.12 g, 93%).

$^1$H NMR (DMSO-d$_6$, 500 MHz) δ 7.96 (d, J=8.4 Hz, 1H), 7.55 (d, J=2.2 Hz, 1H), 7.46 (dd, J=8.4, 1.8 Hz, 1H), 4.19 (t, J=6.5 Hz, 2H), 1.82-1.69 (m, 2H), 1.47-1.28 (m, 4H), 0.90 (t, J=7.1 Hz, 3H).

Step 5: Preparation of 3-(dibromomethylene)-5-(pentyloxy)isobenzofuran-1(3H)-one Triphenylphosphine (1.15 g, 4.4 mmol) was dissolved in 6 ml of THF, which was cooled down to 0° C. under nitrogen gas. THF (5.0 ml) solution containing CBr$_4$ (0.87 g, 2.6 mmol) dissolved therein was added thereto, followed by stirring until the color of the solution turned yellow. After the color change, TEA (0.94 ml, 5.2 mmol) was added drop by drop for 5 minutes, to which THF (1 ml) solution containing the compound prepared in step 4 above (0.20 g, 0.87 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.074 g, 22%).

Figure 11:
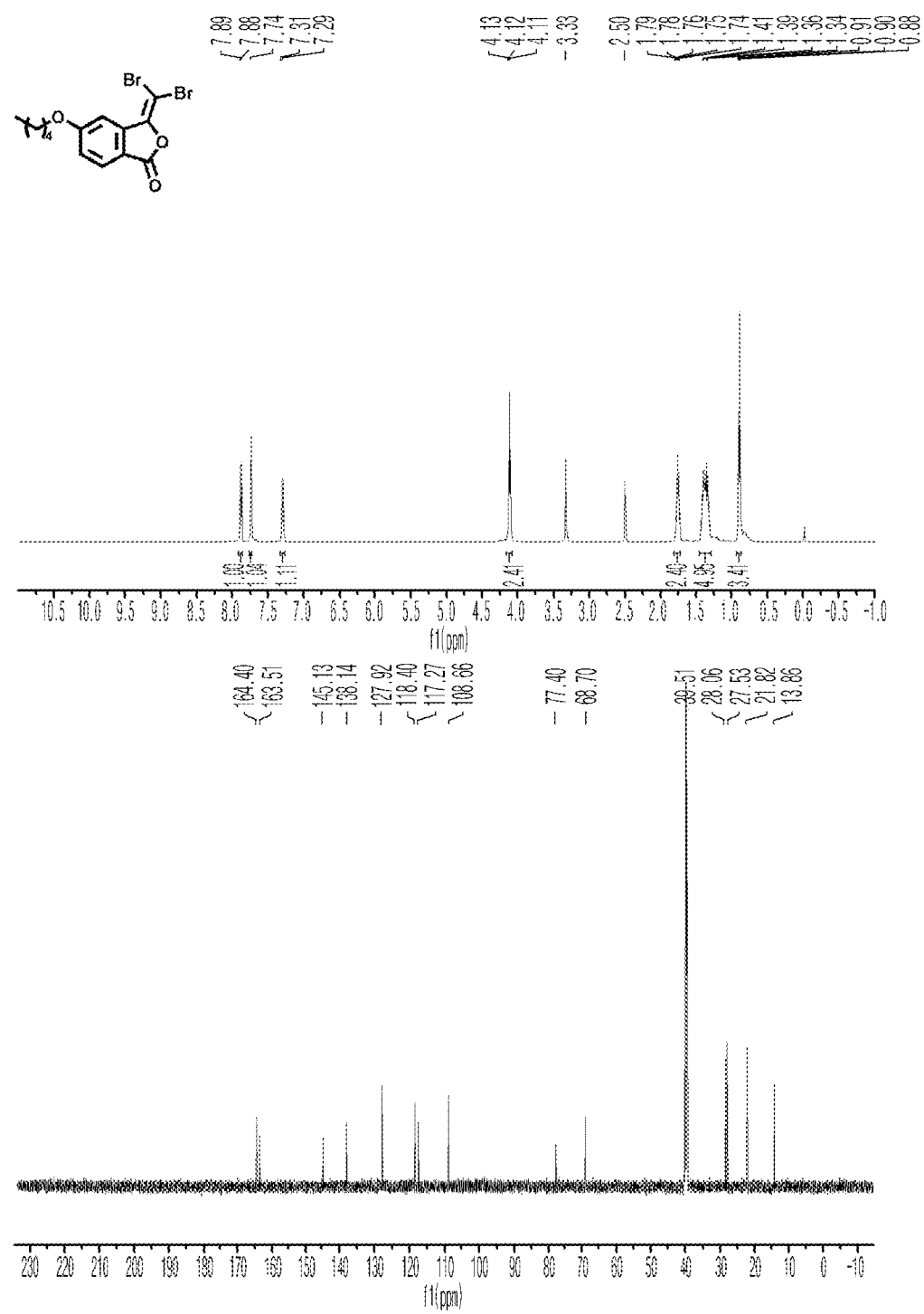
FIG. 11 is a set of graphs illustrating the results of NMR in which the upper graph is a graph showing the results of $^1$H NMR of Example 11, and the lower graph is a graph showing the results of $^{13}$C NMR of Example 11.

NMR graphs of the obtained target compound are shown in FIG. 11.

The upper graph of FIG. 11 is a graph showing the results of $^1$H NMR of Example 11, and the lower graph of FIG. 11 is a graph showing the results of $^{13}$C NMR of Example 11.

$^1$H NMR (DMSO-d$_6$, 500 MHz) δ 7.88 (d, J=8.5 Hz, 1H), 7.74 (s, 1H), 7.30 (d, J=8.6 Hz, 1H), 4.12 (t, J=6.4 Hz, 2H), 1.81-1.72 (m, 2H), 1.46-1.29 (m, 4H), 0.90 (t, J=7.1 Hz, 3H). $^{13}$C NMR (DMSO-d$_6$, 125 MHz) δ 164.4, 163.5, 145.1, 138.1, 127.9, 118.4, 117.3, 108.7, 77.4, 68.7, 28.1, 27.5, 21.8, 13.9.

EXAMPLE 12

Preparation of 5-tert-butyl-3-(dibromomethylene)-5-methylisobenzofuran-1(3H)-one

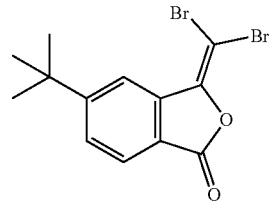 [SMILES: CC(C)(C)c1ccc2c(c1)C(=C(Br)Br)OC2=O]

Triphenylphosphine (1.6 g, 6.0 mmol) was dissolved in 6 ml of THF, which was cooled down to 0° C. under nitrogen gas. THF (6.0 ml) solution containing CBr$_4$ (1.0 g, 3.0 mmol) dissolved therein was added thereto, followed by stirring until the color of the solution turned yellow. After the color change, TEA (1.08 ml, 6.0 mmol) was added drop by drop for 5 minutes, to which THF (1 ml) solution containing 4-tert-butylphthalic acid anhydride (0.20 g, 1.0 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.097 g, 27%).

Figure 12:
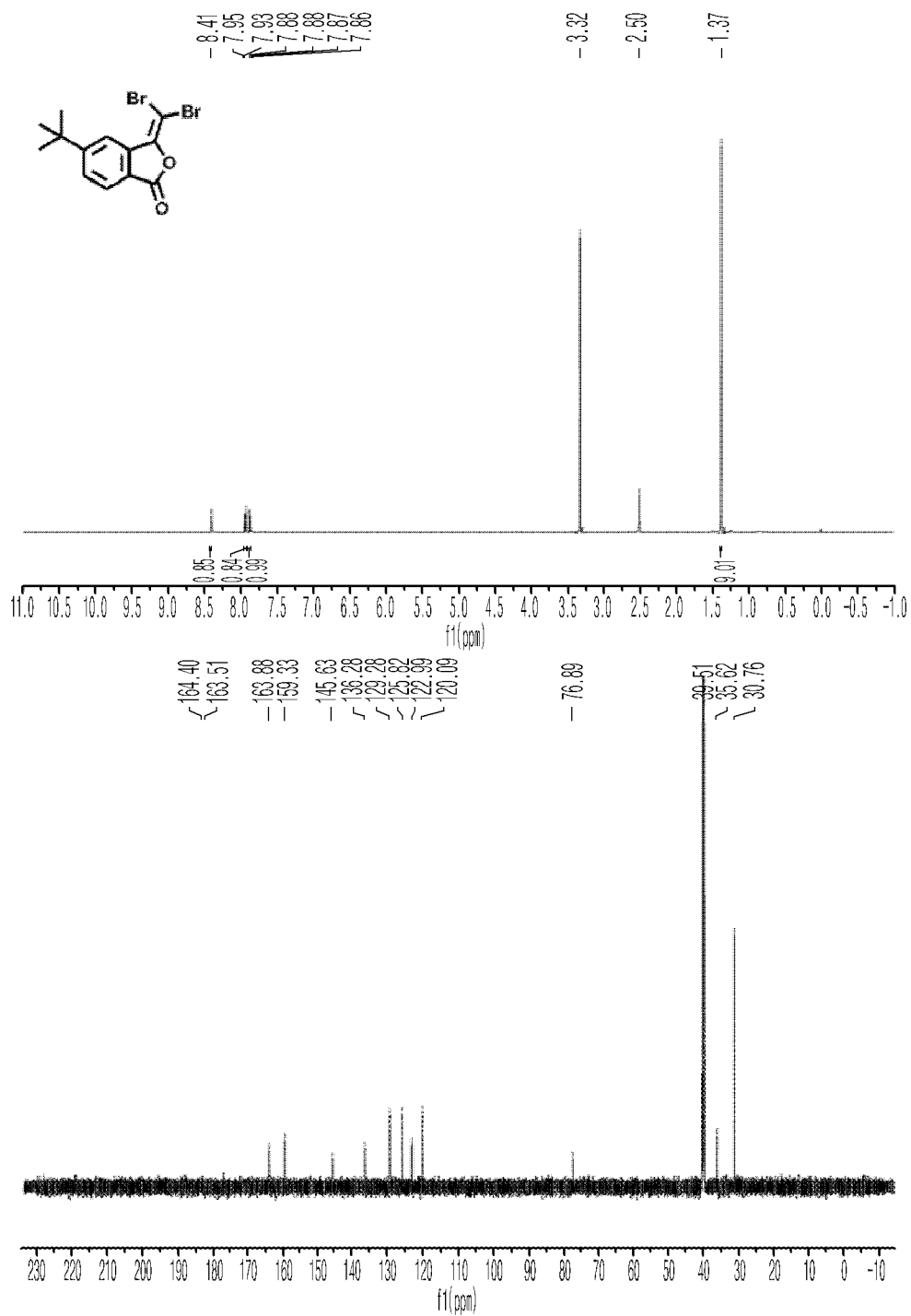
FIG. 12 is a set of graphs illustrating the results of NMR in which the upper graph is a graph showing the results of $^1$H NMR of Example 12, and the lower graph is a graph showing the results of $^{13}$C NMR of Example 12.

NMR graphs of the obtained target compound are shown in FIG. 12.

The upper graph of FIG. 12 is a graph showing the results of $^1$H NMR of Example 12, and the lower graph of FIG. 12 is a graph showing the results of $^{13}$C NMR of Example 12.

$^1$H NMR (DMSO-d$_6$, 500 MHz) δ 8.41 (s, 1H), 7.94 (d, J=8.1 Hz, 1H), 7.87 (dd, J=8.2, 1.6 Hz, 1H), 1.37 (s, 9H). $^{13}$C NMR (DMSO-d$_6$, 125 MHz) δ 159.3, 145.6, 136.3, 129.3, 125.8, 120.1, 76.9, 35.6, 30.8.

EXAMPLE 13

Preparation of 3-(dibromomethylene)-7-methyl-isobenzofuran-1(3H)-one

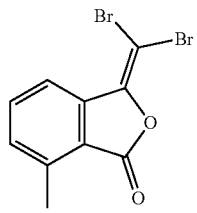

Triphenylphosphine (1.6 g, 6.0 mmol) was dissolved in 6 ml of THF, which was cooled down to 0° C. under nitrogen gas. THF (5.0 ml) solution containing CBr$_4$ (1.0 g, 3.0 mmol) dissolved therein was added thereto, followed by stirring until the color of the solution turned yellow. After the color change, TEA (1.08 ml, 6.0 mmol) was added drop by drop for 5 minutes, to which THF (1 ml) solution containing 3-methylphthalic acid anhydride (0.16 g, 1.0 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.097 g, 31%).

Figure 13:
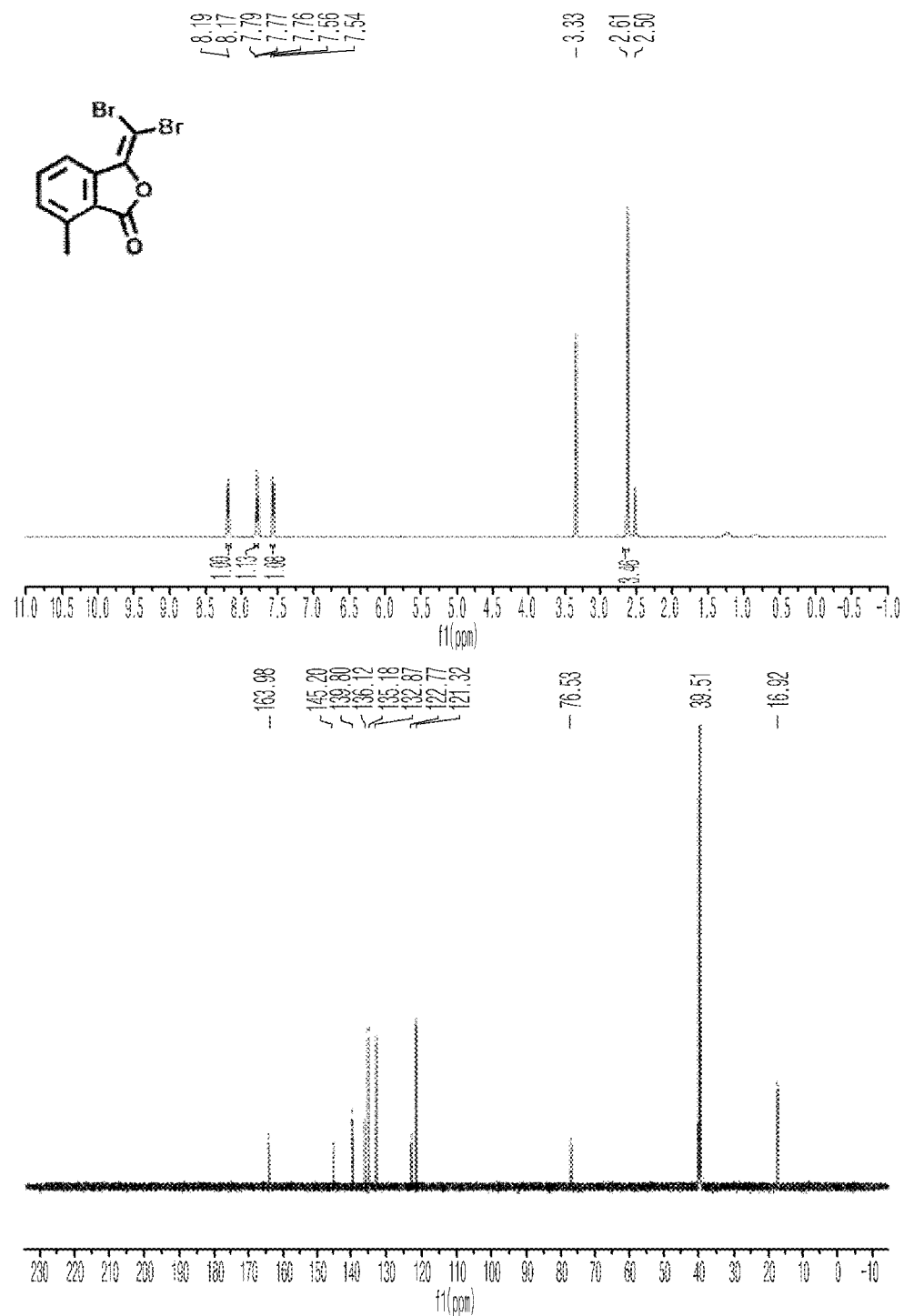
FIG. 13 is a set of graphs illustrating the results of NMR in which the upper graph is a graph showing the results of $^1$H NMR of Example 13, and the lower graph is a graph showing the results of $^{13}$C NMR of Example 13.

NMR graphs of the obtained target compound are shown in FIG. 13.

The upper graph of FIG. 13 is a graph showing the results of $^1$H NMR of Example 13, and the lower graph of FIG. 13 is a graph showing the results of $^{13}$C NMR of Example 13.

$^1$H NMR (DMSO-d$_6$, 500 MHz) δ 8.18 (d, J=7.9 Hz, 1H), 7.77 (t, J=7.7 Hz, 1H), 7.55 (d, J=7.5 Hz, 1H), 2.61 (s, 3H). $^{13}$C NMR (DMSO-d$_6$, 125 MHz) δ 164.0, 145.2, 139.8, 136.1, 135.2, 132.9, 122.8, 121.3, 76.5, 16.9.

EXAMPLE 14

Preparation of 3-(dibromomethylene)-7-ethoxy-isobenzofuran-1(3H)-one

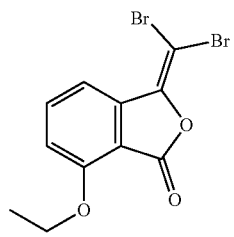 [SMILES: CCOc1cccc2c1C(=O)OC2=C(Br)Br]

Step 1: Preparation of dimethyl 3-hydroxyphthalate

3-Hydroxyphthalic acid (1.09 g, 6.0 mmol) was dissolved in 12 ml of methanol. H$_2$SO$_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over MgSO$_4$, and the solvent was eliminated under reduced pressure. As a result, a crude target compound was obtained (1.05 g, 83%).

$^1$H NMR (DMSO-d$_6$, 500 MHz) δ 10.31 (s, 1H), 7.41-7.35 (m, 2H), 7.17 (dd, J=7.0, 2.2 Hz, 1H), 3.79 (s, 3H), 3.77 (s, 3H). $^{13}$C NMR (DMSO-d$_6$, 125 MHz) δ 167.2, 165.7, 154.6, 130.5, 128.6, 122.6, 120.5, 120.0, 52.4, 52.1.

Step 2: Preparation of dimethyl 3-ethoxyphthalate

The compound prepared in step 1 above (0.5 g, 2.38 mmol) was dissolved in 5 ml of acetone, followed by stirring in the presence of K$_2$CO$_3$ (1.64 g, 11.9 mmol) at room temperature for 1 hour. Iodoethane (0.57 ml, 7.13 mmol) was added thereto, followed by stirring under reflux for overnight. The reaction mixture was filtered to remove K$_2$CO$_3$ and the solvent was eliminated under reduced pressure. After evaporating the solvent, the obtained product was purified by flash column chromatography. As a result, a target compound was obtained (0.49 g, 87%).

$^1$H NMR (DMSO-d$_6$, 500 MHz) δ 7.56-7.49 (m, 2H), 7.39 (dd, J=7.6, 1.8 Hz, 1H), 4.10 (q, J=7.0 Hz, 2H), 3.81 (s, 3H), 3.79 (s, 3H), 1.27 (t, J=7.0 Hz, 3H). $^{13}$C NMR (DMSO-d$_6$, 125 MHz) δ 166.7, 165.2, 155.3, 130.8, 128.0, 124.9, 121.3, 117.5, 64.5, 52.6, 52.1, 14.4.

Step 3: Preparation of 3-ethoxyphthalic acid

The 4 ml of acetone containing the compound prepared in step 2 (0.49 g, 2.07 mmol) dissolved therein was treated with 4 ml of water containing NaOH (0.50 g, 12.4 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over MgSO$_4$, and concentrated under reduced pressure. As a result, a crude target compound was obtained (0.35 g, 81%).

$^1$H NMR (DMSO-d$_6$, 500 MHz) δ 12.94 (s, 2H), 7.48-7.41 (m, 2H), 7.30 (dd, J=7.8, 1.4 Hz, 1H), 4.08 (q, J=7.0 Hz, 2H), 1.28 (t, J=7.0 Hz, 3H). $^{13}$C NMR (DMSO-d$_6$, 125 MHz) δ 167.8, 166.6, 154.9, 129.7, 128.9, 126.8, 121.4, 116.7, 64.3, 14.5.

Step 4: Preparation of 4-ethoxyisobenzofuran-1,3-dione

The compound prepared in step 3 above (0.29 g, 1.4 mmol) was dissolved in 4 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.24 g, 91%).

$^1$H NMR (DMSO-d$_6$, 500 MHz) δ 7.92 (dd, J=8.5, 7.4 Hz, 1H), 7.58 (dd, J=16.4, 7.9 Hz, 2H), 4.31 (q, J=7.0 Hz, 2H), 1.40 (t, J=7.0 Hz, 3H). $^{13}$C NMR (DMSO-d$_6$, 125 MHz) δ 163.2, 160.6, 156.9, 138.7, 133.0, 120.2, 116.8, 116.4, 65.0, 14.3.

Step 5: Preparation of 3-(dibromomethylene)-7-ethoxyisobenzofuran-1(3H)-one

Triphenylphosphine (1.2 g, 4.6 mmol) was dissolved in 6 ml of THF, which was cooled down to 0° C. under nitrogen gas. THF (5.0 ml) solution containing CBr$_4$ (0.76 g, 2.3 mmol) dissolved therein was added thereto, followed by stirring until the color of the solution turned yellow. After the color change, TEA (0.82 ml, 4.6 mmol) was added drop by drop for 5 minutes, to which THF (1 ml) solution containing the compound prepared in step 4 above (0.15 g, 0.76 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.060 g, 23%).

Figure 14:
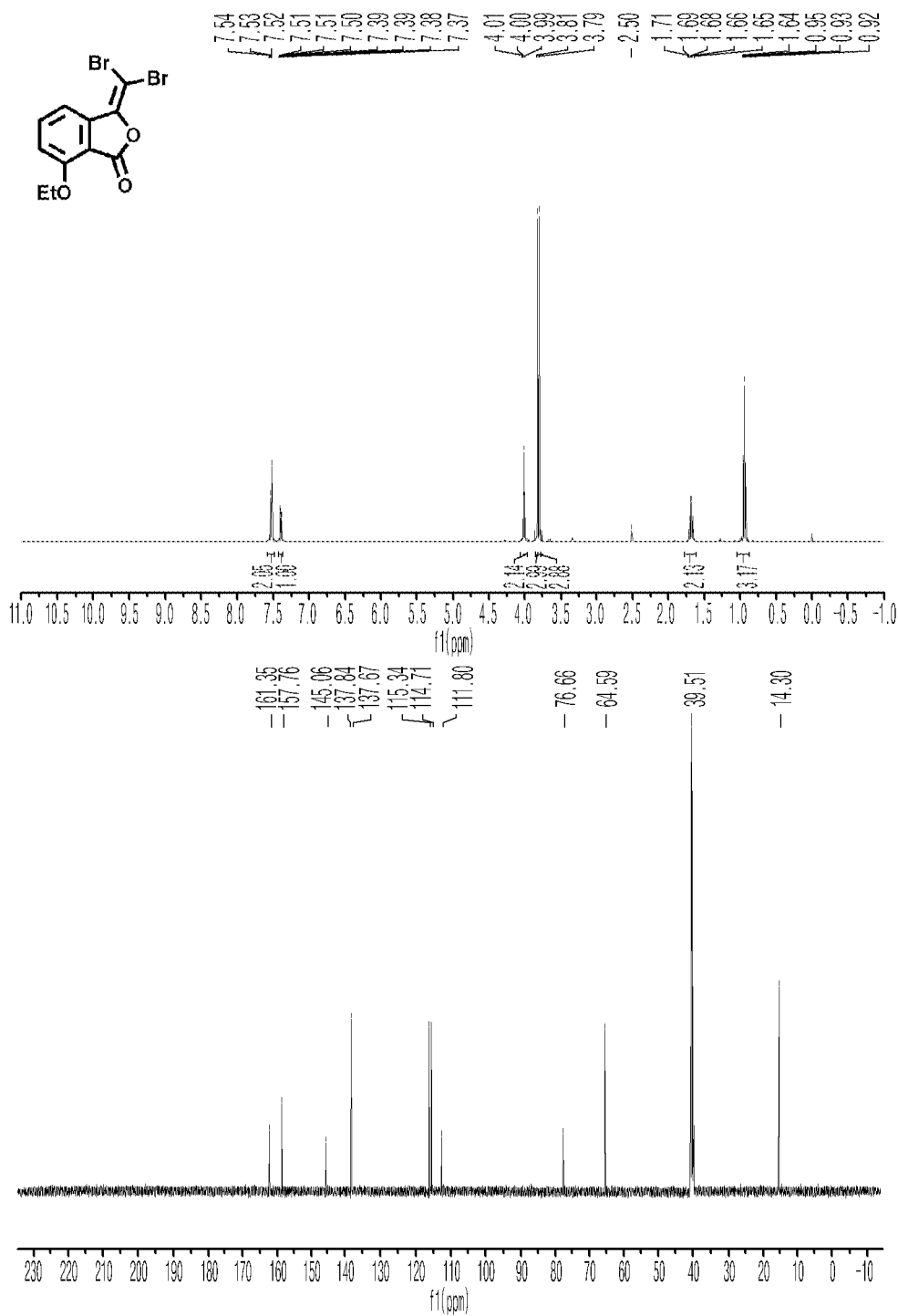
FIG. 14 is a set of graphs illustrating the results of NMR in which the upper graph is a graph showing the results of $^1$H NMR of Example 14, and the lower graph is a graph showing the results of $^{13}$C NMR of Example 14.

NMR graphs of the obtained target compound are shown in FIG. 14.

The upper graph of FIG. 14 is a graph showing the results of $^1$H NMR of Example 14, and the lower graph of FIG. 14 is a graph showing the results of $^{13}$C NMR of Example 14.

$^1$H NMR (DMSO-d$_6$, 500 MHz) δ 7.87 (d, J=7.8 Hz, 1H), 7.82 (t, J=8.0 Hz, 1H), 7.32 (d, J=8.2 Hz, 1H), 4.24 (q, J=6.9 Hz, 2H), 1.38 (t, J=7.0 Hz, 3H). $^{13}$C NMR (DMSO-d$_6$, 125 MHz) δ 161.4, 157.8, 145.1, 137.8, 137.7, 115.3, 114.7, 111.8, 76.7, 64.6, 14.3.

EXAMPLE 15

Preparation of 3-(dibromomethylene)-7-propoxy-isobenzofuran-1(3H)-one

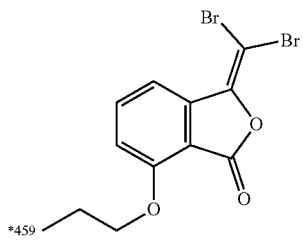 [SMILES: CCCOc1cccc2c1C(=O)OC2=C(Br)Br]

Step 1: Preparation of dimethyl 3-hydroxyphthalate

3-Hydroxyphthalic acid (1.09 g, 6.0 mmol) was dissolved in 12 ml of methanol. H$_2$SO$_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over MgSO$_4$, and the solvent was eliminated under reduced pressure. As a result, a crude target compound was obtained (1.05 g, 83%).

$^1$H NMR (DMSO-d$_6$, 500 MHz) δ 10.31 (s, 1H), 7.41-7.35 (m, 2H), 7.17 (dd, J=7.0, 2.2 Hz, 1H), 3.79 (s, 3H), 3.77 (s, 3H). $^{13}$C NMR (DMSO-d$_6$, 125 MHz) δ 167.2, 165.7, 154.6, 130.5, 128.6, 122.6, 120.5, 120.0, 52.4, 52.1.

Step 2: Preparation of dimethyl 3-propoxyphthalate

The compound prepared in step 1 above (0.5 g, 2.38 mmol) was dissolved in 5 ml of acetone, followed by stirring in the presence of K$_2$CO$_3$ (1.64 g, 11.9 mmol) at room temperature for 1 hour. Iodopropane (0.70 ml, 7.13 mmol) was added thereto, followed by stirring under reflux for overnight. The reaction mixture was filtered to remove K$_2$CO$_3$ and the solvent was eliminated under reduced pressure. After evaporating the solvent, the obtained product was purified by flash column chromatography. As a result, a target compound was obtained (0.52 g, 86%).

$^1$H NMR (DMSO-d$_6$, 500 MHz) δ 7.57-7.47 (m, 2H), 7.38 (dd, J=7.1, 2.3 Hz, 1H), 4.00 (t, J=6.3 Hz, 2H), 3.81 (s, 3H), 3.79 (s, 3H), 1.76-1.59 (m, 2H), 0.93 (t, J=7.4 Hz, 3H). $^{13}$C NMR (DMSO-d$_6$, 125 MHz) δ 166.7, 165.2, 155.4, 130.7, 127.9, 124.9, 121.2, 117.4, 70.0, 52.5, 52.1, 21.9, 10.1.

Step 3: Preparation of 3-propoxyphthalic acid

The 4 ml of acetone containing the compound prepared in step 2 (0.52 g, 2.07 mmol) dissolved therein was treated with 4 ml of water containing NaOH (0.50 g, 12.4 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over MgSO$_4$, and concentrated under reduced pressure. As a result, a crude target compound was obtained (0.34 g, 75%).

$^1$H NMR (DMSO-d$_6$, 500 MHz) δ 12.94 (s, 2H), 7.46 (dd, J=7.8, 1.5 Hz, 1H), 7.43 (t, J=7.8 Hz, 1H), 7.30 (dd, J=7.8, 1.5 Hz, 1H), 3.98 (t, J=6.3 Hz, 2H), 1.68 (dd, J=13.7, 6.4 Hz, 2H), 0.95 (t, J=7.4 Hz, 3H). $^{13}$C NMR (DMSO-d$_6$, 125 MHz) δ 167.7, 166.6, 155.0, 129.6, 128.9, 126.8, 121.3, 116.7, 69.9, 22.0, 10.3.

Step 4: Preparation of 4-propoxyisobenzofuran-1,3-dione

The compound prepared in step 3 above (0.21 g, 0.95 mmol) was dissolved in 3 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.17 g, 87%).

$^1$H NMR (DMSO-d$_6$, 500 MHz) δ 7.92 (dd, J=8.4, 7.4 Hz, 1H), 7.60 (d, J=8.5 Hz, 1H), 7.56 (d, J=7.4 Hz, 1H), 4.20 (t, J=6.4 Hz, 2H), 1.85-1.75 (m, 2H), 1.02 (t, J=7.4 Hz, 3H). $^{13}$C NMR (DMSO-d$_6$, 125 MHz) δ 163.2, 160.6, 157.1, 138.7, 133.0, 120.3, 116.8, 116.4, 70.5, 21.7, 10.1.

Step 5: Preparation of 3-(dibromomethylene)-7-propoxy-isobenzofuran-1(3H)-one

Triphenylphosphine (0.94 g, 3.6 mmol) was dissolved in 6 ml of THF, which was cooled down to 0° C. under nitrogen gas. THF (5.0 ml) solution containing CBr$_4$ (0.60 g, 1.8 mmol) dissolved therein was added thereto, followed by stirring until the color of the solution turned yellow. After the color change, TEA (0.65 ml, 3.6 mmol) was added drop by drop for 5 minutes, to which THF (1 ml) solution containing the compound prepared in step 4 above (0.12 g, 0.6 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.043 g, 20%).

Figure 15:
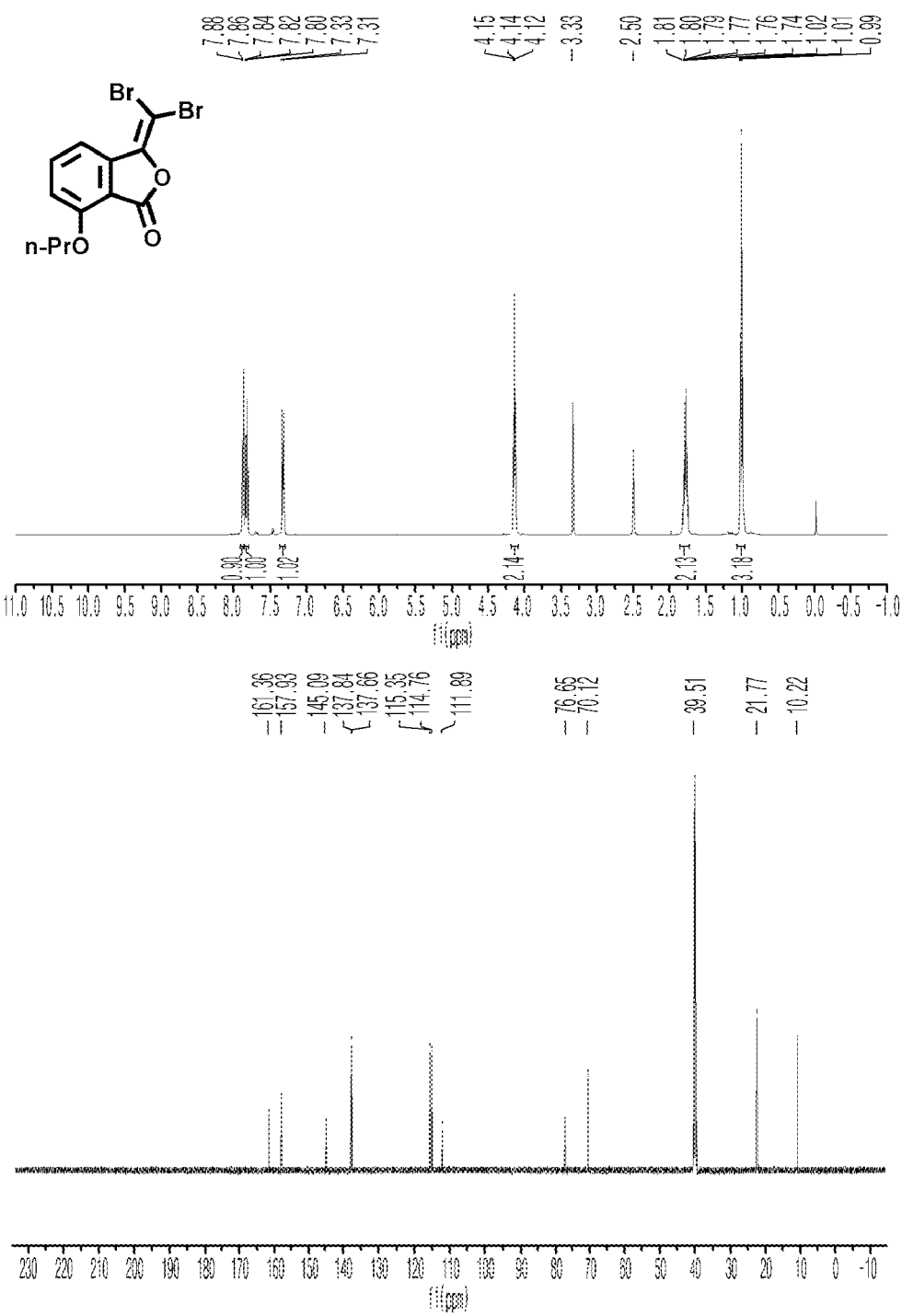
FIG. 15 is a set of graphs illustrating the results of NMR in which the upper graph is a graph showing the results of $^1$H NMR of Example 15, and the lower graph is a graph showing the results of $^{13}$C NMR of Example 15.

NMR graphs of the obtained target compound are shown in FIG. 15.

The upper graph of FIG. 15 is a graph showing the results of $^1$H NMR of Example 15, and the lower graph of FIG. 15 is a graph showing the results of $^{13}$C NMR of Example 15.

$^1$H NMR (DMSO-$d_6$, 500 MHz) δ 7.87 (d, J=7.8 Hz, 1H), 7.82 (t, J=8.0 Hz, 1H), 7.32 (d, J=8.3 Hz, 1H), 4.13 (t, J=6.4 Hz, 2H), 1.85-1.73 (m, 2H), 1.01 (t, J=7.4 Hz, 3H). $^{13}$C NMR (DMSO-$d_6$, 125 MHz) δ 161.4, 157.9, 145.1, 137.8, 137.7, 115.4, 114.8, 111.9, 76.7, 70.1, 21.8, 10.2.

EXAMPLE 16

Preparation of 7-butoxy-3-(dibromomethylene)isobenzofuran-1(3H)-one

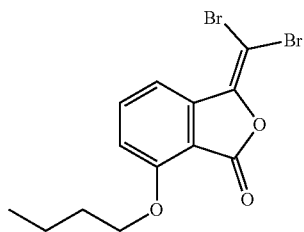 [SMILES: CCCCOc1cccc2c1C(=O)OC2=C(Br)Br]

Step 1: Preparation of dimethyl 3-hydroxyphthalate

3-Hydroxyphthalic acid (1.09 g, 6.0 mmol) was dissolved in 12 ml of methanol. $H_2SO_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over $MgSO_4$, and the solvent was eliminated under reduced pressure. As a result, a crude target compound was obtained (1.05 g, 83%).

$^1$H NMR (DMSO-$d_6$, 500 MHz) δ 10.31 (s, 1H), 7.41-7.35 (m, 2H), 7.17 (dd, J=7.0, 2.2 Hz, 1H), 3.79 (s, 3H), 3.77 (s, 3H). $^{13}$C NMR (DMSO-$d_6$, 125 MHz) δ 167.2, 165.7, 154.6, 130.5, 128.6, 122.6, 120.5, 120.0, 52.4, 52.1.

Step 2: Preparation of dimethyl 3-butoxyphthalate

The compound prepared in step 1 above (0.5 g, 2.38 mmol) was dissolved in 5 ml of acetone, followed by stirring in the presence of $K_2CO_3$ (1.64 g, 11.9 mmol) at room temperature for 1 hour. Iodobutane (0.81 ml, 7.13 mmol) was added thereto, followed by stirring under reflux for overnight. The reaction mixture was filtered to remove $K_2CO_3$ and the solvent was eliminated under reduced pressure. After evaporating the solvent, the obtained product was purified by flash column chromatography. As a result, a target compound was obtained (0.51 g, 80%).

$^1$H NMR (DMSO-$d_6$, 500 MHz) δ 7.55-7.50 (m, 2H), 7.39 (dd, J=7.4, 1.9 Hz, 1H), 4.04 (t, J=6.3 Hz, 2H), 3.81 (s, 3H), 3.78 (s, 3H), 1.69-1.59 (m, 2H), 1.46-1.33 (m, 2H), 0.90 (t, J=7.4 Hz, 3H). $^{13}$C NMR (DMSO-$d_6$, 125 MHz) δ 166.7, 165.2, 155.4, 130.7, 127.9, 124.9, 121.2, 117.4, 68.3, 52.5, 52.1, 30.5, 18.5, 13.5.

Step 3: Preparation of 3-butoxyphthalic acid

The 4 ml of acetone containing the compound prepared in step 2 (0.52 g, 1.92 mmol) dissolved therein was treated with 4 ml of water containing NaOH (0.46 g, 11.5 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over $MgSO_4$, and concentrated under reduced pressure. As a result, a crude target compound was obtained (0.36 g, 79%).

$^1$H NMR (DMSO-$d_6$, 500 MHz) δ 12.94 (s, 2H), 7.46 (dd, J=7.8, 1.1 Hz, 1H), 7.42 (t, J=7.9 Hz, 1H), 7.29 (dd, J=8.1, 1.1 Hz, 1H), 4.01 (t, J=6.3 Hz, 2H), 1.70-1.59 (m, 2H), 1.46-1.34 (m, 2H), 0.90 (t, J=7.4 Hz, 3H). $^{13}$C NMR (DMSO-$d_6$, 125 MHz) δ 167.8, 166.6, 155.1, 129.7, 128.9, 126.8, 121.3, 116.7, 68.3, 30.7, 18.7, 13.7.

Step 4: Preparation of 4-butoxyisobenzofuran-1,3-dione

The compound prepared in step 3 above (0.29 g, 1.21 mmol) was dissolved in 3 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.23 g, 85%).

$^1$H NMR (DMSO-$d_6$, 500 MHz) δ 7.91 (dd, J=8.4, 7.4 Hz, 1H), 7.60 (d, J=8.5 Hz, 1H), 7.56 (d, J=7.3 Hz, 1H), 4.24 (t, J=6.4 Hz, 2H), 1.82-1.71 (m, 2H), 1.54-1.42 (m, 2H), 0.95 (t, J=7.4 Hz, 3H). $^{13}$C NMR (DMSO-$d_6$, 125 MHz) δ 163.2, 160.5, 157.1, 138.7, 133.0, 120.2, 116.8, 116.4, 68.8, 30.3, 18.5, 13.6.

Step 5: Preparation of 7-butoxy-3-(dibromomethylene)isobenzofuran-1(3H)-one

Triphenylphosphine (1.1 g, 4.1 mmol) was dissolved in 4 ml of THF, which was cooled down to 0° C. under nitrogen gas. THF (5.0 ml) solution containing $CBr_4$ (0.68 g, 2.0 mmol) dissolved therein was added thereto, followed by stirring until the color of the solution turned yellow. After the color change, TEA (0.73 ml, 4.1 mmol) was added drop by drop for 5 minutes, to which THF (1 ml) solution containing the compound prepared in step 4 above (0.15 g, 0.68 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated $NH_4Cl$ aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.054 g, 21%).

Figure 16:
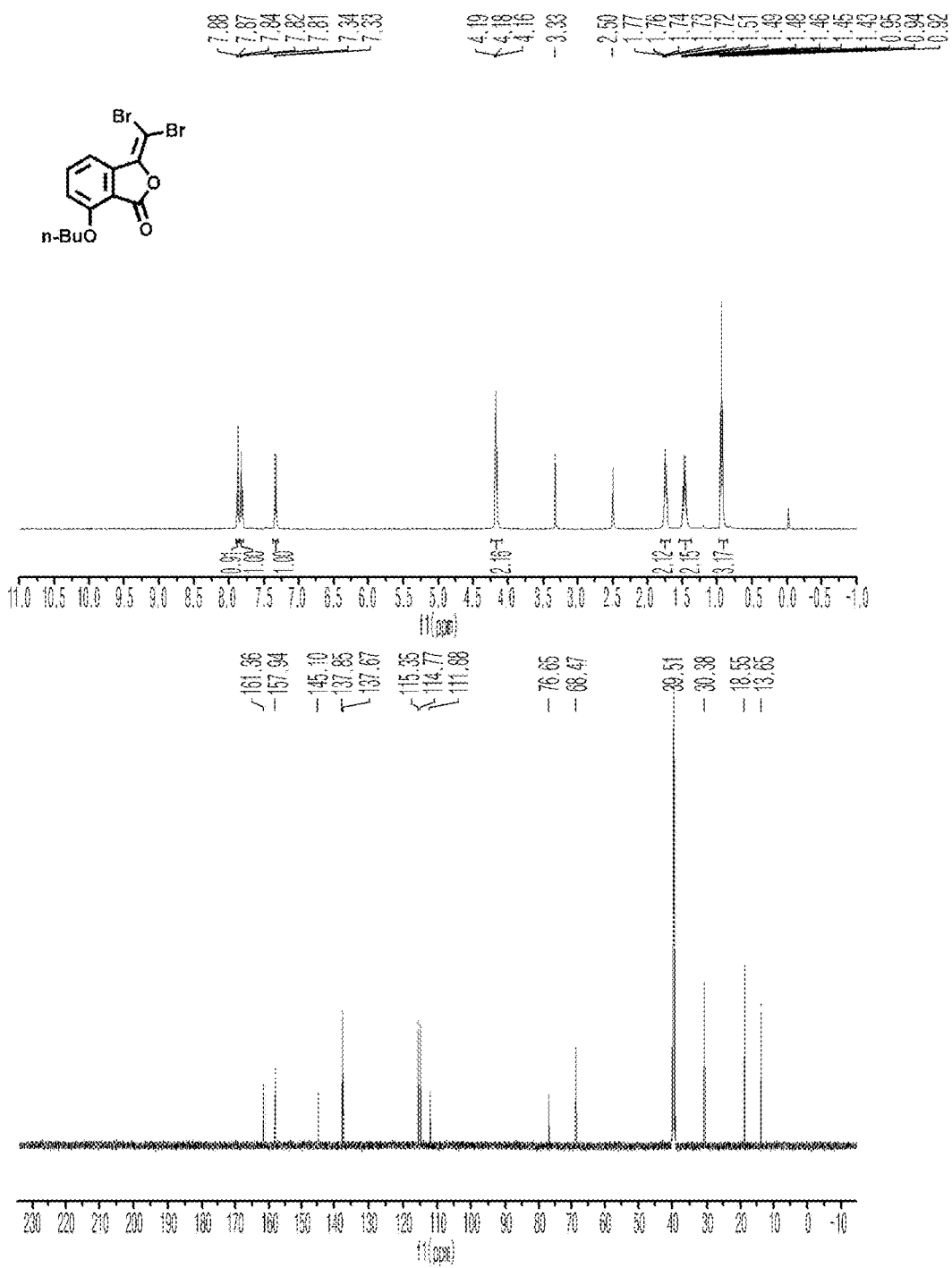
FIG. 16 is a set of graphs illustrating the results of NMR in which the upper graph is a graph showing the results of $^1$H NMR of Example 16, and the lower graph is a graph showing the results of $^{13}$C NMR of Example 16.

NMR graphs of the obtained target compound are shown in FIG. 16.

The upper graph of FIG. 16 is a graph showing the results of $^1$H NMR of Example 16, and the lower graph of FIG. 16 is a graph showing the results of $^{13}$C NMR of Example 16.

$^1$H NMR (DMSO-$d_6$, 500 MHz) δ 7.88 (d, J=7.8 Hz, 1H), 7.82 (t, J=8.0 Hz, 1H), 7.33 (d, J=8.3 Hz, 1H), 4.18 (t, J=6.4 Hz, 2H), 1.80-1.66 (m, 2H), 1.53-1.37 (m, 2H), 0.94 (t, J=7.4 Hz, 3H). $^{13}$C NMR (DMSO-$d_6$, 125 MHz) δ 161.4, 157.9, 145.1, 137.9, 137.7, 115.4, 114.8, 111.9, 76.7, 68.5, 30.4, 18.6, 13.7.

EXAMPLE 17

Preparation of 3-(dibromomethylene)-7-(pentyloxy) isobenzofuran-1(3H)-one

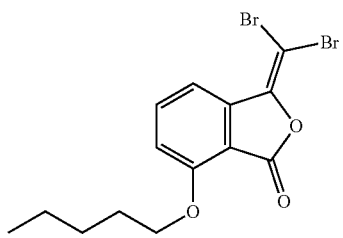 [SMILES: CCCCCOc1cccc2c1C(=O)OC2=C(Br)Br]

Step 1: Preparation of dimethyl 3-hydroxyphthalate

3-Hydroxyphthalic acid (1.09 g, 6.0 mmol) was dissolved in 12 ml of methanol. H$_2$SO$_4$ (0.054 ml, 1.02 mmol) was added thereto as a catalyst. The reaction mixture was stirred under reflux for overnight. The solvent was eliminated under reduced pressure, and the obtained solid was dissolved in dichloromethane, which was washed with water. The combined organic layer was dried over MgSO$_4$, and the solvent was eliminated under reduced pressure. As a result, a crude target compound was obtained (1.05 g, 83%).

$^1$H NMR (DMSO-$d_6$, 500 MHz) δ 10.31 (s, 1H), 7.41-7.35 (m, 2H), 7.17 (dd, J=7.0, 2.2 Hz, 1H), 3.79 (s, 3H), 3.77 (s, 3H). $^{13}$C NMR (DMSO-$d_6$, 125 MHz) δ 167.2, 165.7, 154.6, 130.5, 128.6, 122.6, 120.5, 120.0, 52.4, 52.1.

Step 2: Preparation of dimethyl 3-pentyloxyphthalate

The compound prepared in step 1 above (0.50 g, 2.38 mmol) was dissolved in 5 ml of acetone, followed by stirring in the presence of K$_2$CO$_3$ (1.64 g, 11.9 mmol) at room temperature for 1 hour. Iodopentane (0.93 ml, 7.13 mmol) was added thereto, followed by stirring under reflux for overnight. The reaction mixture was filtered to remove K$_2$CO$_3$ and the solvent was eliminated under reduced pressure. After evaporating the solvent, the obtained product was purified by flash column chromatography. As a result, a target compound was obtained (0.55 g, 82%).

$^1$H NMR (DMSO-$d_6$, 500 MHz) δ 7.55-7.49 (m, 2H), 7.39 (d, J=7.4 Hz, 1H), 4.03 (t, J=6.2 Hz, 2H), 3.81 (s, 3H), 3.78 (s, 3H), 1.69-1.63 (m, 2H), 1.39-1.27 (m, 4H), 0.88 (t, J=6.9 Hz, 3H). $^{13}$C NMR (DMSO-$d_6$, 125 MHz) δ 166.7, 165.2, 155.4, 130.7, 127.9, 124.9, 121.2, 117.4, 68.6, 52.5, 52.0, 28.1, 27.5, 21.7, 13.9.

Step 3: Preparation of 3-pentyloxyphthalic acid

The 4 ml of acetone containing the compound prepared in step 2 (0.40 g, 1.43 mmol) dissolved therein was treated with 3 ml of water containing NaOH (0.34 g, 8.6 mmol) dissolved therein, followed by stirring at room temperature for overnight. After evaporating acetone, the reaction mixture was acidized with 6 M HCl to adjust to pH 2, followed by extraction with ethyl acetate. The combined organic layer was dried over MgSO$_4$, and concentrated under reduced pressure. As a result, a crude target compound was obtained (0.29 g, 80%).

$^1$H NMR (DMSO-$d_6$, 500 MHz) δ 12.93 (s, 2H), 7.46 (dd, J=7.8, 1.5 Hz, 1H), 7.43 (t, J=7.8 Hz, 1H), 7.30 (dd, J=7.8, 1.5 Hz, 1H), 4.01 (t, J=6.4 Hz, 2H), 1.71-1.61 (m, 2H), 1.43-1.27 (m, 4H), 0.88 (t, J=7.2 Hz, 3H). $^{13}$C NMR (DMSO-$d_6$, 125 MHz) δ 167.7, 166.6, 155.0, 129.6, 128.9, 126.8, 121.3, 116.6, 68.5, 28.3, 27.5, 21.8, 13.9.

Step 4: Preparation of 4-pentyloxyisobenzofuran-1,3-dione

The compound prepared in step 3 above (0.25 g, 1.0 mmol) was dissolved in 3 ml of acetic anhydride. The prepared solution was heated under reflux for 18 hours. The temperature of the solution was cooled down to room temperature, followed by concentration by rotary evaporation. The obtained residue was purified by flash column chromatography. As a result, a target compound was obtained (0.20 g, 84%).

$^1$H NMR (DMSO-$d_6$, 500 MHz) δ 7.91 (dd, J=8.4, 7.4 Hz, 1H), 7.60 (d, J=8.5 Hz, 1H), 7.55 (d, J=7.4 Hz, 1H), 4.23 (t, J=6.5 Hz, 2H), 1.79 (dd, J=14.1, 7.3 Hz, 2H), 1.52-1.30 (m, 4H), 0.90 (t, J=7.2 Hz, 3H). $^{13}$C NMR (DMSO-$d_6$, 125 MHz) δ 163.2, 160.5, 157.1, 138.7, 133.0, 120.2, 116.8, 116.4, 69.1, 28.0, 27.4, 21.8, 13.9.

Step 5: Preparation of 7-pentyloxy-3-(dibromomethylene)isobenzofuran-1(3H)-one

Triphenylphosphine (1.3 g, 4.9 mmol) was dissolved in 5 ml of THF, which was cooled down to 0° C. under nitrogen gas. THF (5.0 ml) solution containing CBr$_4$ (0.81 g, 2.4 mmol) dissolved therein was added thereto, followed by stirring until the color of the solution turned yellow. After the color change, TEA (0.87 ml, 4.9 mmol) was added drop by drop for 5 minutes, to which THF (1 ml) solution containing the compound prepared in step 4 above (0.19 g, 0.81 mmol) dissolved therein was added gradually. The reaction solution was stirred at 0° C. for 30 minutes. Then, the temperature of the reaction solution was adjusted to room temperature, followed by stirring for overnight. The reaction was quenched with a saturated NH$_4$Cl aqueous solution. When the phases were separated, the water layer was extracted by using hexane. The combined organic layer was concentrated under reduced pressure. The obtained residue was dissolved in ethoxyethane and filtered through a celite pad. The obtained solution was concentrated by rotary evaporation and purified by flash column chromatography. As a result, a target compound was obtained (0.060 g, 19%).

Figure 17:
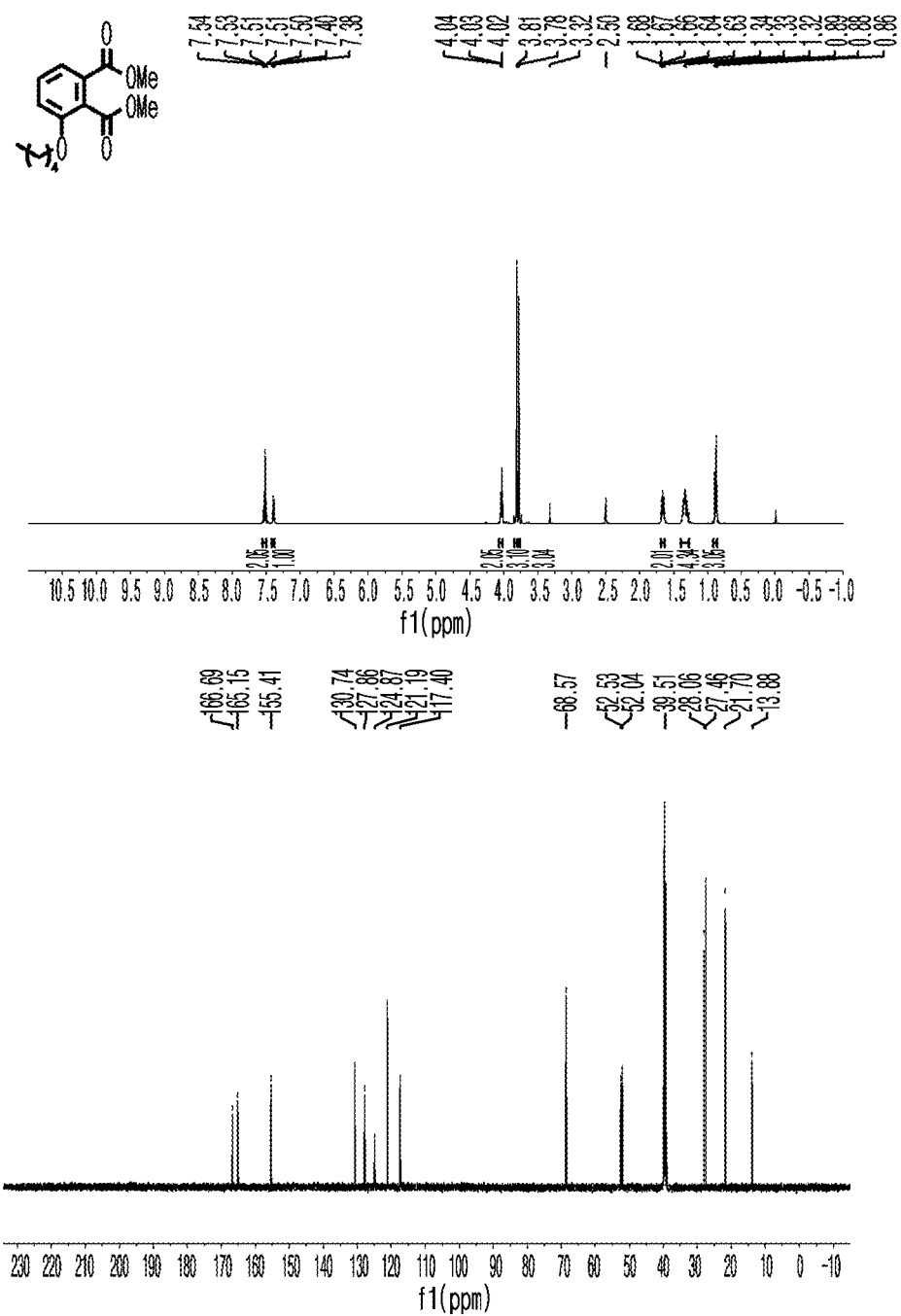
FIG. 17 is a set of graphs illustrating the results of NMR in which the upper graph is a graph showing the results of $^1$H NMR of Example 17, and the lower graph is a graph showing the results of $^{13}$C NMR of Example 17.

NMR graphs of the obtained target compound are shown in FIG. 17.

The upper graph of FIG. 17 is a graph showing the results of $^1$H NMR of Example 17, and the lower graph of FIG. 17 is a graph showing the results of $^{13}$C NMR of Example 17.

$^1$H NMR (DMSO-$d_6$, 500 MHz) δ 7.89 (d, J=7.8 Hz, 1H), 7.83 (t, J=8.0 Hz, 1H), 7.34 (d, J=8.3 Hz, 1H), 4.18 (t, J=6.5 Hz, 2H), 1.84-1.70 (m, 2H), 1.50-1.28 (m, 4H), 0.89 (t,

J=7.2 Hz, 3H). $^{13}$C NMR (DMSO-d$_6$, 125 MHz) δ 161.4, 157.9, 145.1, 137.9, 137.7, 115.4, 114.8, 111.9, 76.6, 68.8, 28.0, 27.5, 21.8, 13.9.

EXAMPLE 18

Preparation of 2-butyl-3-(dibromomethylene)isoindolin-1-one

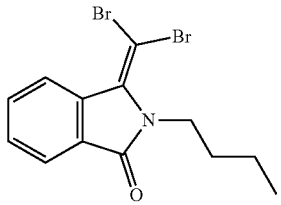 [SMILES: CCCCN1C(=O)c2ccccc2C1=C(Br)Br]

3-(Dibromomethylene)isobenzofuran-1(3H)-one (0.49 g, 1.6 mmol) was dissolved in DCM, followed by stirring in a 0° C. ice bath. DCM (1 ml) containing n-butylamine (0.48 ml, 48 mmol) dissolved therein was added thereto drop by drop. The obtained mixture was stirred at 0° C. for 30 minutes, and heated to room temperature for 12 hours. Upon completion of the reaction, the resulting solution was acidized with 1 M HCl, followed by extraction using ethyl acetate. The combined organic layer was dried over MgSO$_4$, followed by concentration under reduced pressure. As a result, a target compound was obtained (0.27 g, 44%).

$^1$H NMR (DMSO-d$_6$, 500 MHz) δ 7.97 (d, J=7.4 Hz, 1H), 7.68 (t, J=7.6 Hz, 2H), 7.59 (t, J=7.4 Hz, 1H), 6.73 (s, 1H), 3.52-3.29 (m, 2H), 1.74-1.67 (m, 2H), 1.39-1.30 (m, 2H), 0.92 (t, J=7.4 Hz, 3H). $^{13}$C NMR (DMSO-d$_6$, 125 MHz) δ 166.6, 143.9, 132.5, 131.7, 130.1, 123.5, 122.0, 90.5, 50.4, 38.4, 30.5, 20.0, 13.7.

Figure 18:
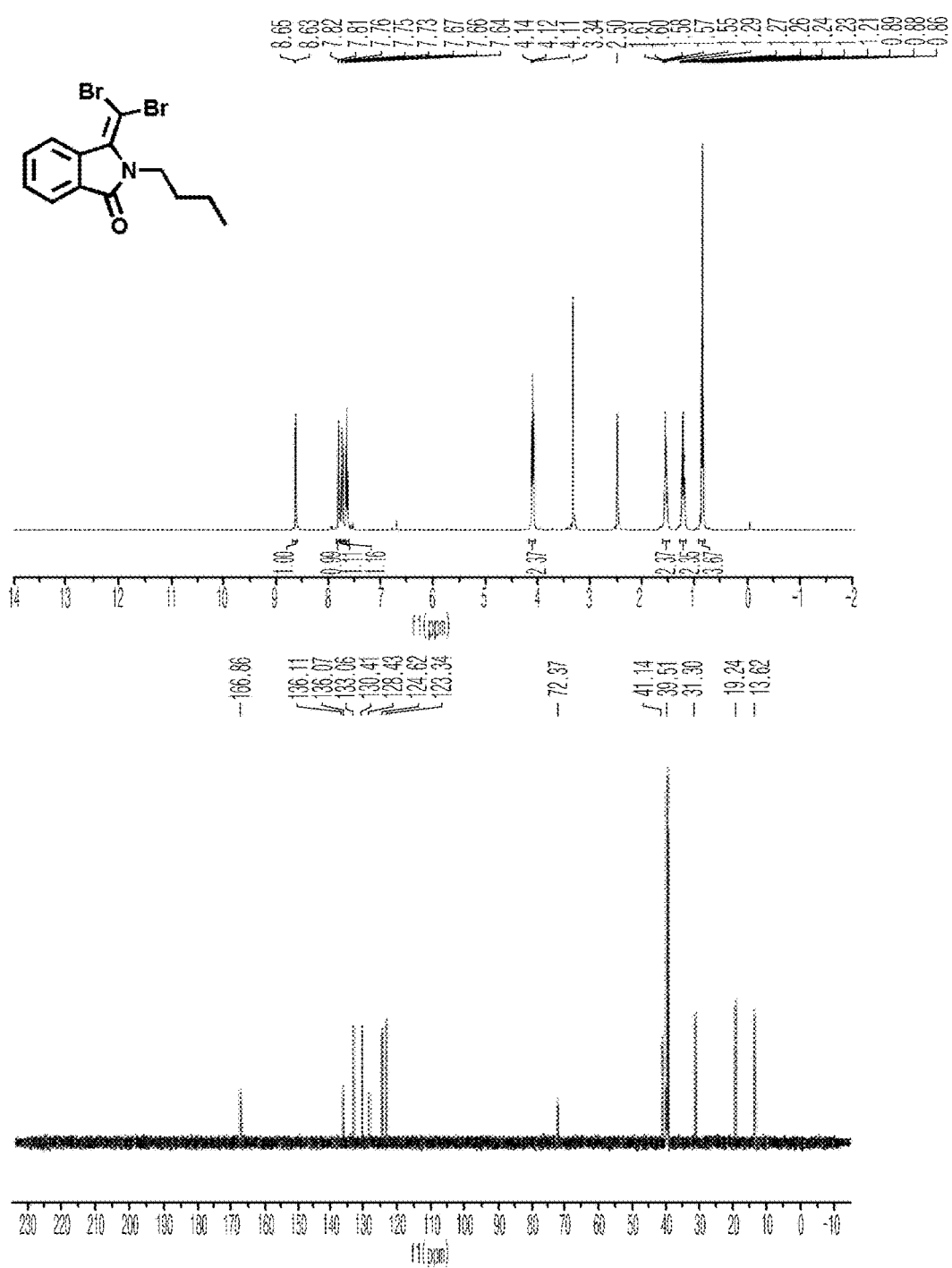
FIG. 18 is a set of graphs illustrating the results of NMR in which the upper graph is a graph showing the results of $^1$H NMR of Example 18, and the lower graph is a graph showing the results of $^{13}$C NMR of Example 18.

The upper graph of FIG. 18 is a graph showing the results of $^1$H NMR of Example 18, and the lower graph of FIG. 18 is a graph showing the results of $^{13}$C NMR of Example 18.

The compounds prepared in Examples 1 to 18 are shown in Table 1 below.

TABLE 1-continued

| Example | Formula |
|---------|---------|
| 10 | (5-butoxy isobenzofuran-1(3H)-ylidene)dibromomethane structure |
| 11 | (5-pentyloxy isobenzofuran-1(3H)-ylidene)dibromomethane structure |
| 12 | (5-tert-butyl isobenzofuran-1(3H)-ylidene)dibromomethane structure |
| 13 | (7-methyl isobenzofuran-1(3H)-ylidene)dibromomethane structure |
| 14 | (7-ethoxy isobenzofuran-1(3H)-ylidene)dibromomethane structure |
| 15 | (7-propoxy isobenzofuran-1(3H)-ylidene)dibromomethane structure |
| 16 | (7-butoxy isobenzofuran-1(3H)-ylidene)dibromomethane structure |
| 17 | (7-pentyloxy isobenzofuran-1(3H)-ylidene)dibromomethane structure |
| 18 | (2-butyl-3-(dibromomethylene)isoindolin-1-one) structure |

EXPERIMENTAL EXAMPLE 1

Evaluation of AI-2 (autoinducer-2) Inhibitory Activity Using Bioluminescence

To evaluate the AI-2 (autoinducer-2) inhibitory activity of the compound of the present invention, the following experiment was performed.

Particularly, the autoinducer-2 reporter strain V. harveyi BB170 was cultured in AB medium (autoinducer bioassay medium) at 30° C. for 24 hours under aerobic condition. Upon completion of the culture, the cells were diluted to the density of $1\times10^6$ cells/ml, which was distributed to each well of a 96 well microplate equally by 160 μl (When V. harveyi BB170 cells recognized the intercellular signaling molecule AI-2, the growth was accelerated and accordingly the luciferase expression was increased, resulting in the increase of bioluminescence. The number of the cultured cells was calculated by measuring $OD_{600}$. When the cells were diluted to the target density, fresh AB medium was used for the dilution).

40 μl of AB medium was added to each well of the negative control BB170 group (V. harveyi BB170 alone). 20 μl of AB medium and 20 μl of F.n AI-2 were added to each well of the positive control F.nucleatum AI-2 group (F.n AI-2).

To each well of the experimental group, 20 μl of F.n AI-2 was added first. The concentration of the compounds of examples of the present invention was adjusted to 200 μM, and then 20 μl of the compound solution was added to each well of the experimental group. The total volume of each well was 200 μl. AI-2 and the compound of each example were treated thereto by 10% (If the well is treated with the example compound solution at the concentration of 10% by the total volume, the actual effective concentration would be 20 μM which is 1/10 diluted concentration). All the experimental groups, including the control group, were distributed identically in 3 wells (triplicate) per group and the final data were calculated as the mean value.

V. harveyi cells were re-cultured while maintaining the treated well plate at 30° C. for 6 hours under aerobic condition. Luminescence values of V. harveyi were measured by a photometer (GloMax-Multi detection system, Promega, Madison, Wis., USA) every 3 hours (0 h, 3 h, 6 h). The results are shown in FIG. 19.

Figure 19:
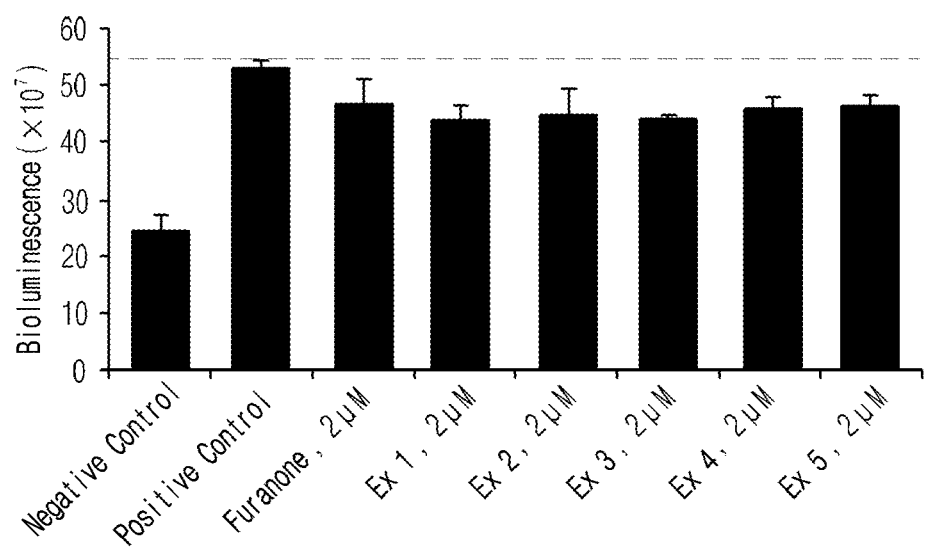
FIG. 19 is a graph illustrating the inhibitory activity of the compound according to an example of the present invention, the negative control and the positive control against AI-2 (autoinducer-2), which is a quorum sensing signal molecule.

FIG. 19 is a graph illustrating the inhibitory activity of the compound according to an example of the present invention, the negative control and the positive control against AI-2 (autoinducer-2), which is a quorum sensing signal molecule.

As shown in FIG. 19, the compounds of examples of the present invention inhibited the quorum sensing signal molecule AI-2 (autoinducer-2) and thus showed a low bioluminescence value.

Therefore, as confirmed in Experimental Example 1, the compound of the present invention inhibits the quorum sensing of bacteria efficiently, so that a pharmaceutical composition comprising the compound as an active ingredient can be effective in treating periodontal diseases such as gingivitis and periodontitis.

EXPERIMENTAL EXAMPLE 2

Evaluation of Inhibition of Biofilm Formation

The following experiment was performed to evaluate the inhibitory activity of the compound of the present invention to biofilm formation of bacteria.

Particularly, a sterilized cover glass slip (round shape with a radius of 12 mm) was placed on each well of a cell culture plate (24 well plate) by using a pincette. *F. nucleatum* A1-2 was added to cell culture medium (BHI medium+supplements) at the volume of 10% by the total volume.

The compounds of examples of the present invention were diluted to make the final concentration of each compound of 2 μM, 0.2 μM and 0.02 μM (BH1 medium: Brain Heart Infusion Medium, supplements: hemin (10 μg/ml) and vitamin K (0.2 μg/ml)).

The prepared culture solution was added to each well of the plate where the glass slip was placed, and the desired number of bacteria was inoculated into each well (*F. nucleatum*: $2 \times 10^7$ cells/ml, *P. gingivalis*: $4 \times 10^8$ cells/ml, *T. forsythia*: $2 \times 10^8$ cells/ml).

For the positive control not treated with the compounds of examples of the present invention (F.n AI-2), F. nucleatum AI-2 was added to the cell culture medium (BHI+supplements) and then the same number of cells was inoculated.

In the meantime, for the negative control treated neither the compound of the present invention nor *F. nucleatum* A1-2 (Fn), PBS was added to the cell culture medium (BHI+supplements) instead of *F. nucleatum* A1-2 at the same volume as the above.

The prepared well plate was incubated at 37° C. under anaerobic condition (10% $H_2$, 10% $CO_2$ and 80% $N_2$) for 48 hours for the culture of bacteria. The biofilm formed on the glass slip by the bacteria cultured in each group was quantitatively and comparatively analyzed using the following techniques.

<2-1> Crystal Violet Staining

The glass slip whereon biofilm had been formed was stained with 1% crystal violet solution for 10 minutes, followed by washing with PBS (phosphate buffered saline) three times, and decolorized with acetone-alcohol.

200 μl of the decolorizing solution containing crystal violet was added to each well of the microplate, and $OD_{595}$ was measured using a microplate reader (Microplate reader, Model 550, Bio-Rad, USA). The measured values were compared among the groups (As the biofilm formation increased by the molecules secreted by *F. nucleatum* was suppressed by the compound of the present invention, the measured value was decreased.).

Figure 20:
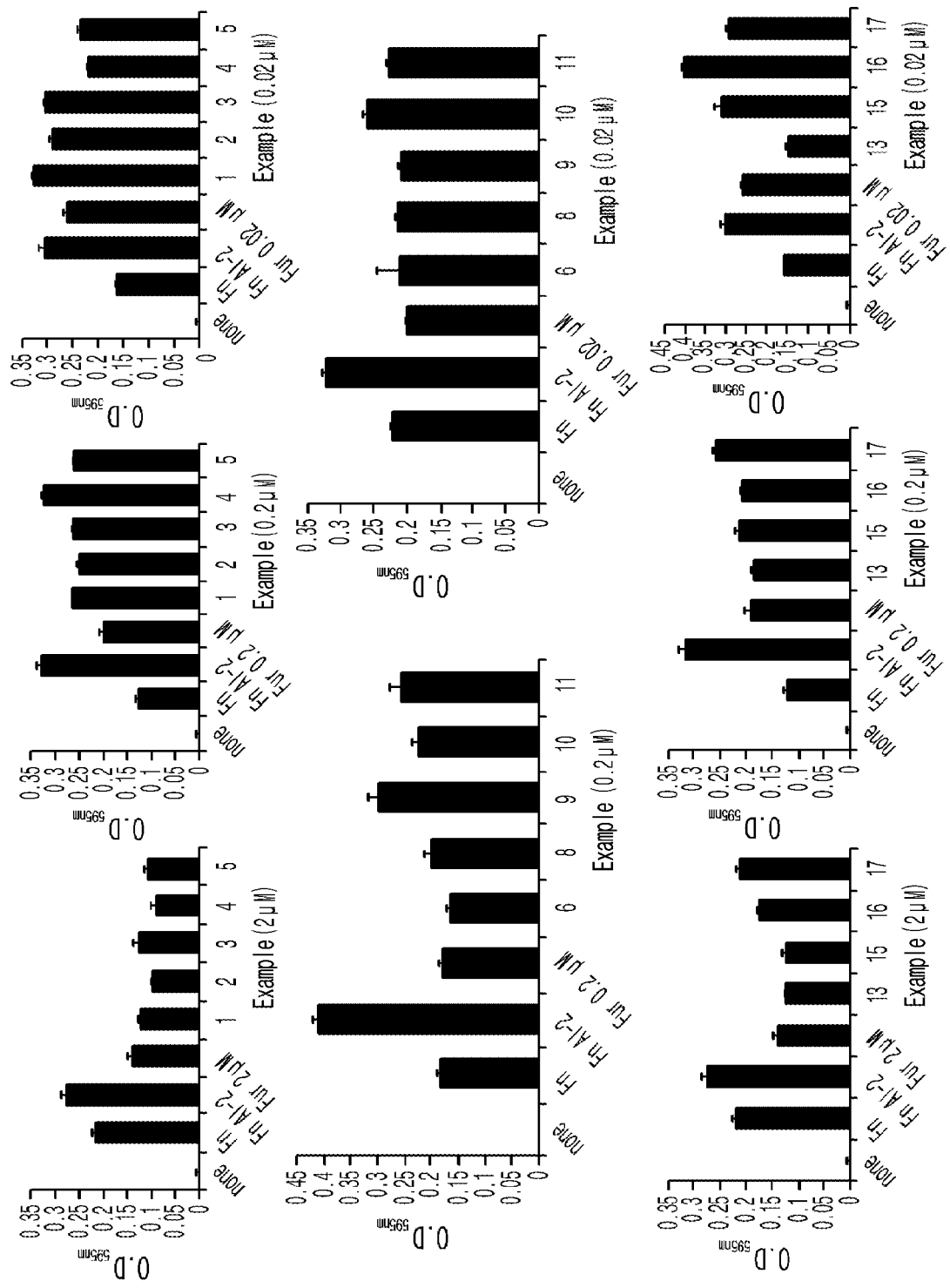
FIG. 20 is a set of graphs illustrating the values of $OD_{595}$ corresponding to *F. nucleatum* biofilm (A) of the experimental group, the positive control group and the negative control group. The graphs presented in the upper part, in the middle and in the lower part of FIG. 20 illustrate the values of $OD_{595}$ at the concentration of the test sample of 2000 nM, 200 nM and 20 nM respectively.

The results of the experiment above are shown in FIG. 20.

FIG. 20 is a set of graphs illustrating the values of $OD_{595}$ corresponding to *F. nucleatum* biofilm (A) of the experimental group, the positive control group and the negative control group. The graphs presented in the upper part, in the middle and in the lower part of FIG. 20 illustrate the values of $OD_{595}$ at the concentration of the test sample of 2000 nM, 200 nM and 20 nM respectively.

Figure 21:
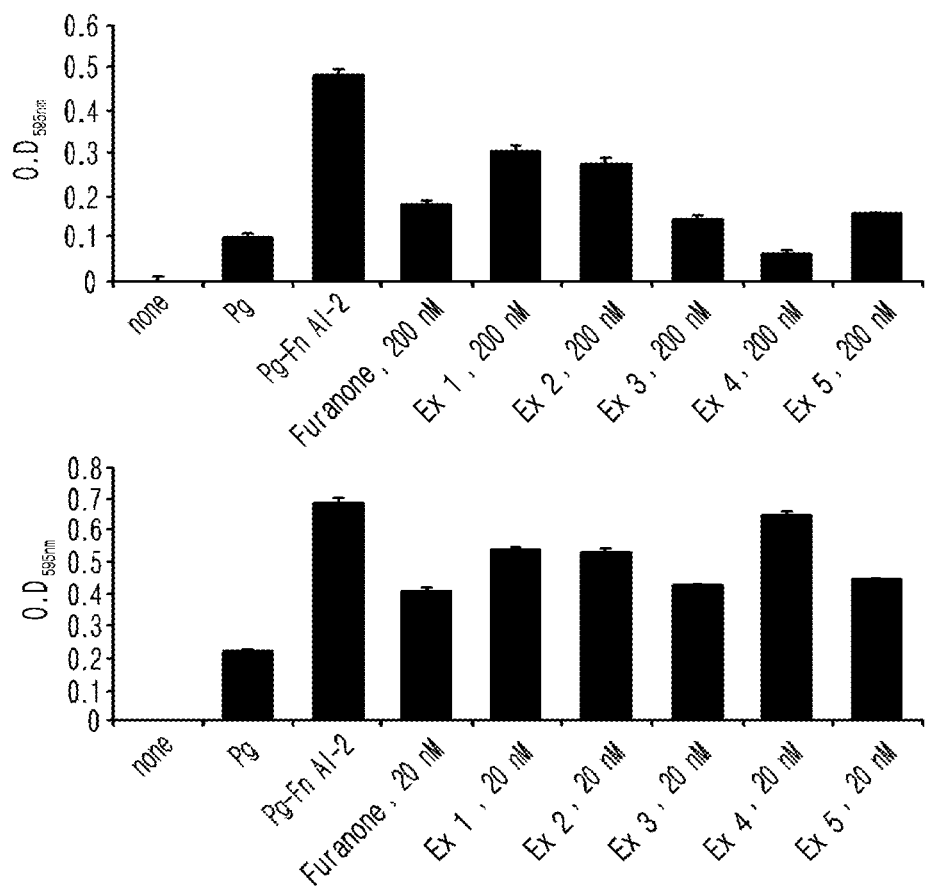
FIG. 21 is a set of graphs illustrating the values of $OD_{595}$ corresponding to *P. gingivalis* biofilm (B) of the experimental group, the positive control group and the negative control group. The graphs presented in the upper part, in the middle and in the lower part of FIG. 21 illustrate the values of $OD_{595}$ at the concentration of the test sample of 2000 nM, 200 nM and 20 nM respectively.

FIG. 21 is a set of graphs illustrating the values of $OD_{595}$ corresponding to *P. gingivalis* biofilm (B) of the experimental group, the positive control group and the negative control group. The graphs presented in the upper part, in the middle and in the lower part of FIG. 21 illustrate the values of OD595 at the concentration of the test sample of 2000 nM, 200 nM and 20 nM respectively.

As shown in FIG. 20~FIG. 21, the compound according to an example of the present invention demonstrated the biofilm inhibitory activity in units of nM concentration. In particular, the compounds of Example 4 and Example 5 exhibited superior *F. nucleatum* biofilm inhibitory activity at the concentration of 20 nM to the furanone treated control group. In the meantime, the compound of Example 3 had excellent *P. gingivalis* biofilm inhibitory activity.

<2-2> Confocal Scanning Laser Microscope Technique

The glass slip whereon biofilm had been formed was stained by using a live/dead-BacLight bacterial viability kit (Invitrogen, Grand Island, N.Y., USA), and the morphology of the biofilm was observed under a confocal scanning laser microscope and compared. The results are shown in FIG. 21.

Figure 22:
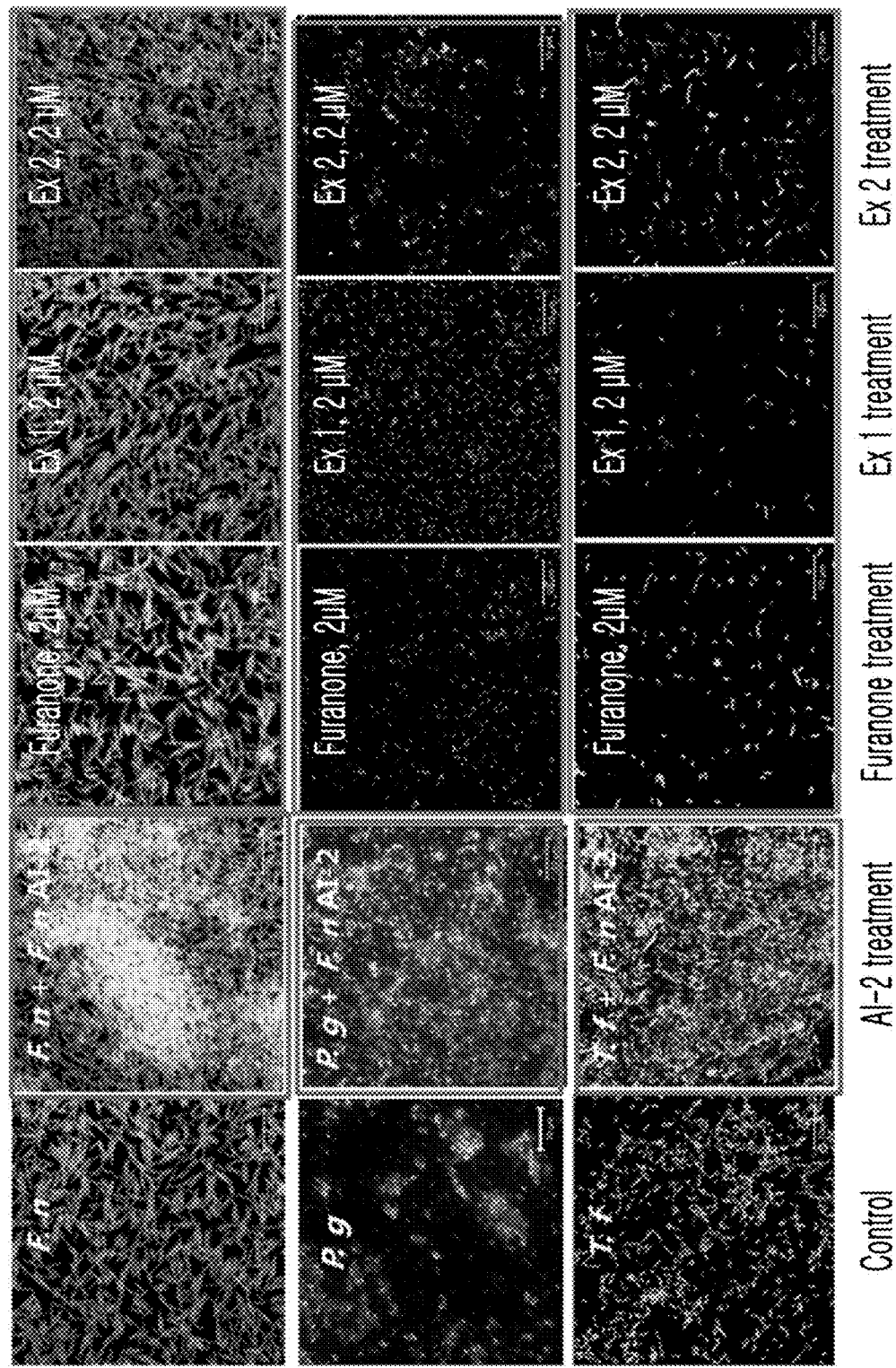
FIG. 22 is a set of photographs illustrating the biofilms of *F. nucleatum, givalis* and *T. forsythia* observed with a confocal scanning laser microscope after treating them with nothing or AI-2, furanone, the compound of Example 4 or Example 2, respectively.

FIG. 22 is a set of photographs illustrating the biofilms of *F. nucleatum, givalis* and *T. forsythia* observed with a confocal scanning laser microscope after treating them with nothing or A1-2, furanone, the compound of Example 4 or Example 2, respectively.

As shown in FIG. 22, it was confirmed by photographs that the compounds of Example 2 and Example 4 of the present invention inhibited the biofilm formation of bacteria.

As confirmed in Experimental Example 2 above, the compound of the present invention was excellent in inhibiting the biofilm formation of bacteria in the unit concentration of nM, so that a pharmaceutical composition containing the compound of the invention as an active ingredient can be effectively used for the treatment of periodontal diseases such as gingivitis and periodontitis.

EXPERIMENTAL EXAMPLE 3

Evaluation of Cytotoxicity

To evaluate the toxicity of the compound according to the present invention to normal cells, the following experiment was performed.

<3-1> Evaluation of Cytotoxicity in Human Mononuclear Cell Line (THP-1) and Gingival Fibroblast Cell Line (HGF)

To investigate whether or not the compound according to an example of the present invention which had been confirmed to have the excellent periodontal pathogen biofilm inhibitory activity had cytotoxicity in host cells (normal cells), 50 μl of human mononuclear cells (THP-1,$1 \times 10^5$ cells/well) or gingival fibroblasts (HGF, $1 \times 10^5$ cells/well) and 50 μl of the compound of each example prepared at the concentration of 2 μM or 20 μM were distributed in each well of a 96 well plate, followed by culture at 37° C. for 24 hours. Upon completion of the 24 hour culture, 10 μl of CCK-8 (cell counting kit-8, Dojindo Molecular Technologies, Inc) solution was added to each well, followed by culture in a 37° C. incubator. $OD_{450}$ was measured for 1~4 hours at one hour intervals to evaluate the cell viability. The results are shown in FIG. 23.

The control group was treated with ethanol (0.1%, 0.01% or 0.2%) under the same conditions as described above.

Figure 23:
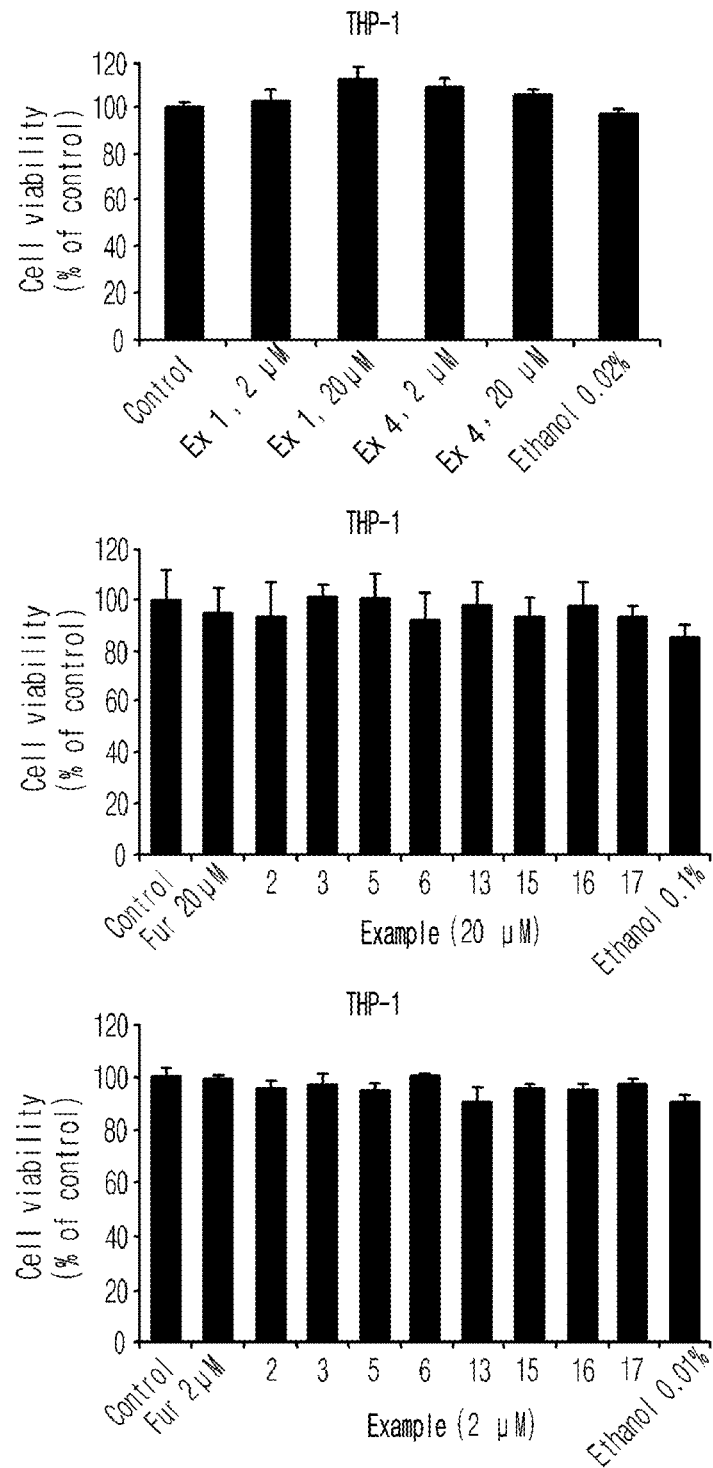
FIG. 23 is a graph illustrating the cell viability of mononuclear cells (THP-1) in the experimental group treated with the compounds of examples of the present invention and in the control group treated with ethanol.

FIG. 23 is a graph illustrating the cell viability of mononuclear cells (THP-1) in the experimental group treated with the compounds of examples of the present invention and in the control group treated with ethanol.

Figure 24:
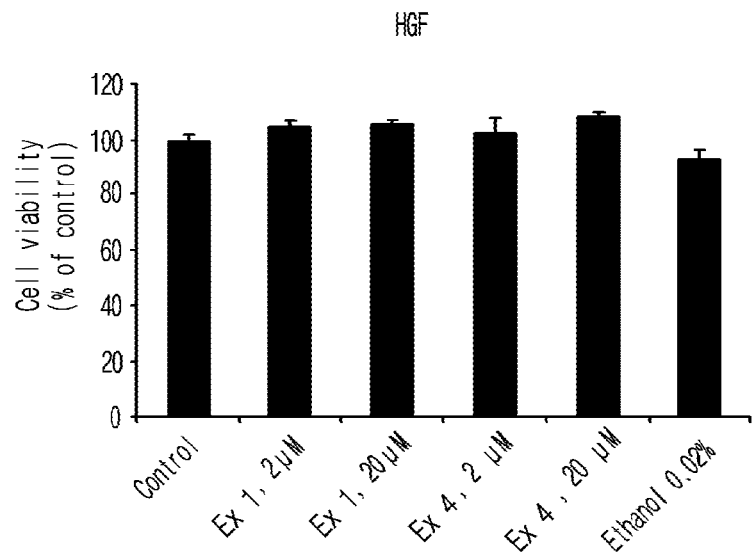
FIG. 24 is a graph illustrating the cell viability of human gingival fibroblasts (HGF) in the experimental group treated with the compounds of examples of the present invention and in the control group treated with ethanol.

FIG. 24 is a graph illustrating the cell viability of human gingival fibroblasts (HGF) in the experimental group treated with the compounds of examples of the present invention and in the control group treated with ethanol.

As shown in FIG. 23 and FIG. 24, the compounds of examples of the present invention hardly showed cytotoxicity to mononuclear cells. If there was cytotoxicity observed, the cytotoxicity of the compounds of examples of the present invention was less than the control group treated with ethanol.

The compounds of the present invention can inhibit the quorum sensing of bacteria and the biofilm formation of bacteria but showed little toxicity to normal cells, so that the compounds of the present invention can be used as an active ingredient of a pharmaceutical composition for the prevention or treatment of periodontal diseases such as gingivitis and periodontitis.

<3-2> Evaluation of Cytotoxicity in Human Oral Keratinocyte Cell Line (HOK-16B)

Cytotoxicity of those compounds of Examples 5, 6 and 13, which were confirmed to be particularly excellent in inhibiting biofilm formation, among all the compounds of examples of the present invention, was investigated in human oral keratinocyte cell line (HOK-16B).

Particularly, HOK-16B cells were cultured in a keratinocyte basic medium (Lonza, Walkersville, Md., USA) supplemented with insulin, epidermal growth factor, bovine pituitary extract, hydrocortisone, and gentamicin sulfate amphotericin. The cultured HOK-16B cells ($5 \times 10^4$ cells/well) were inoculated in a 96 well plate, where the cells were grown until the fusion level reached 85%. Then the cells were treated with the compounds of the present invention, followed by culture for 24 hours. Cell viability was evaluated by using CCK-8 (cell counting kit-8, Dojindo Molecular Technologies, Inc) according to the manufacturer's protocol.

Figure 25:
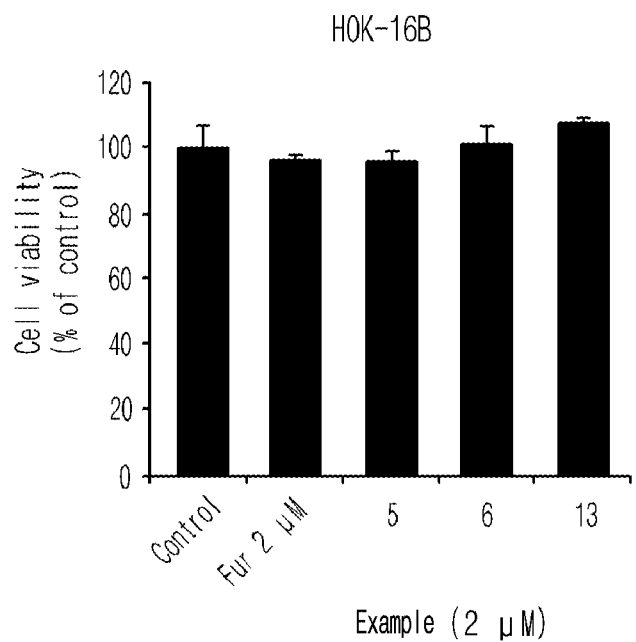
FIG. 25 is a graph illustrating the cell viability of human oral keratinocytes (HOK-16B) in the group treated with the compounds of examples of the present invention.

FIG. 25 is a graph illustrating the cell viability of human oral keratinocytes (HOK-16B) in the group treated with the compounds of examples of the present invention.

As shown in FIG. 25, the compounds of examples of the present invention hardly had toxicity to human oral keratinocytes.

The compounds of the present invention can inhibit the quorum sensing of bacteria and the biofilm formation of bacteria but showed little toxicity to normal cells, so that the compounds of the present invention can be used as an active ingredient of a pharmaceutical composition for the prevention or treatment of periodontal diseases such as gingivitis and periodontitis.

EXPERIMENTAL EXAMPLE 4

Evaluation of Effect of the Compounds on Host Cell Immunity

To evaluate the effect of the compounds of the present invention on host cell (normal cell) immunity, the host cells were treated with the compounds of the present invention, followed by investigation of the activity of proinflammatory cytokines in host cells.

Particularly, in order to investigate whether or not the compounds of the present invention were able to induce inflammatory responses in host cells, the expression levels of proinflammatory cytokines including interleukin (IL)-6 and IL-8 were measured by real-time RT-PCR. THP-1 cells ($1 \times 10^6$ cells/well) and HGF cells ($2 \times 10^5$ cells/well) were distributed in a 6 well plate, followed by culture in the presence or absence of the compounds of examples (5, 6 and 13) or lipopolysaccharide (LPS, 1 mg) known as an endotoxin of Gram negative bacteria that causes a strong immune response in host cells at 37° C. for 24 hours. Upon completion of the 24 hour culture, RNA was extracted from the THP-1 and HGF cells by using Easy-Blue total RNA extraction kit (iNtRON Biotechnology, Seongnam, Korea) according to the manufacturer's protocol. A cDNA sample (2 mL) synthesized from the extracted RNA (1 mg) using MMLV reverse transcription kit (Promega, Madison, Wis.) was added to each primer pair (10 pM) and Power SYBR Green Master Mix (Applied Biosystems, Warrington, UK) at the reaction volume of 20 mL. The mixture was applied to ABI PRISM 7500 Fast Real-Time PCR system (Applied Biosystems, Foster City, Calif., USA) by using thermocycling (thermocycling: denaturation at 95° C. for 15 seconds, annealing and extension at 60° C. for 1 minute). Glyceraldehyde 3-phosphate dehydrogenase (GAPDH) gene was used as a reference gene to normalize the gene expression levels of inflammatory cytokines including interleukin 6 (IL-6) and interleukin 8 (IL-8).

Sequences of the primers used in this experiment are as follows.

GAPDH: 5'-GTG GCC AGC CGA GCC-3' (SEQ ID NO: 1) and 5'-TGA AGG GGT TGA TGG CA-3' (SEQ ID NO: 2)

IL-6: 5'-GAT TCA ATG AGG AGA CTT GCC TGG-3' (SEQ ID NO: 3) and 5'-GCA GAA CTG GAT CAG GAC TTT-3' (SEQ ID NO: 4)

IL-8: 5'-CTG TGT GAA GGT GCA GTT TTG C-3' (SEQ ID NO: 5) and 5'-AAC TTC TCC ACA ACC CTC TGC-3' (SEQ ID NO: 6).

Figure 26:
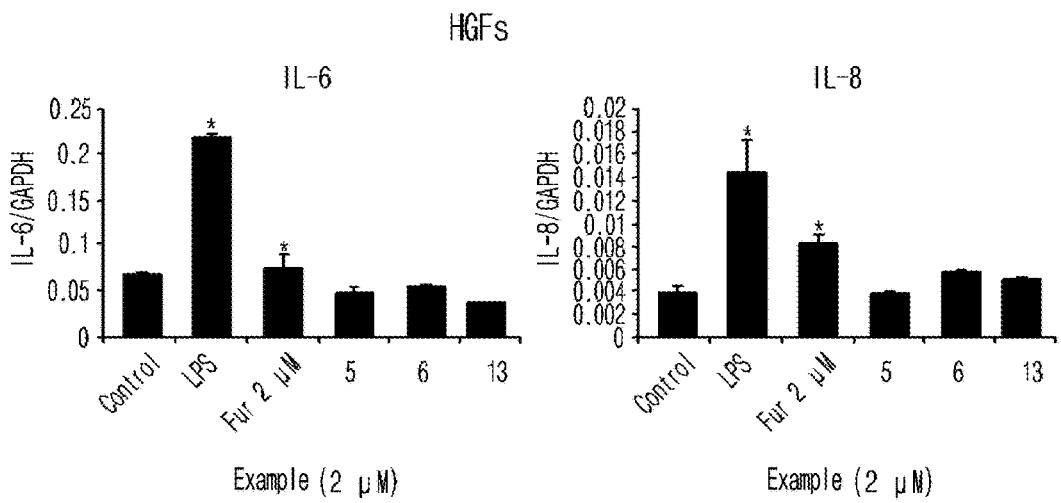
FIG. 26 is a graph illustrating the expressions of IL-6 and IL-8 genes as an activity index of proinflammatory cytokines in THP-1 cells treated with the compounds of examples of the present invention, furanone or LPS respectively.
Figure 27:
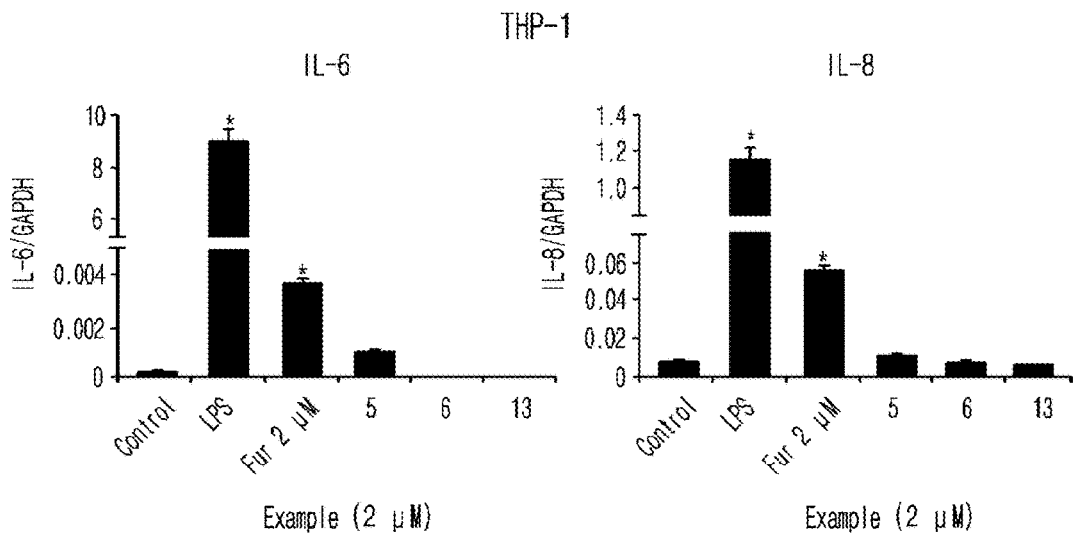
FIG. 27 is a graph illustrating the expressions of IL-6 and IL-8 genes as an activity index of proinflammatory cytokines in HGF cells treated with the compounds of examples of the present invention, furanone or LPS respectively.

The results of this experiment are shown in those graphs in FIG. 26 and FIG. 27.

FIG. 26 is a graph illustrating the expressions of IL-6 and IL-8 genes as an activity index of proinflammatory cytokines in THP-1 cells treated with the compounds of examples of the present invention, furanone or LPS respectively.

FIG. 27 is a graph illustrating the expressions of IL-6 and IL-8 genes as an activity index of proinflammatory cytokines in HGF cells treated with the compounds of examples of the present invention, furanone or LPS respectively.

As shown in FIG. 26, the compounds of examples 5, 6 and 13 were confirmed not to induce inflammatory responses, while the control furanone compound or lipopolysaccharide (LPS; 1 mg/mL) induced the expressions of IL-6 and IL-8 genes, indicating that the control compound did induce inflammatory responses in THP-1 cells.

As shown in FIG. 27, the compounds of examples 5, 6 and 13 did not induce the expressions of IL-6 and IL-8 genes, while the control furanone compound induced the expression of IL-8 gene and LPS (1 mg/mL) induced the expressions of both cytokines, indicating that the control compound induced inflammatory responses in HGF cells.

The compounds of the present invention can inhibit the biofilm formation of bacteria significantly but shows little toxicity to host cells and do not induce inflammatory responses in host cells, unlike the control furanone compound. Thus, the compounds of the present invention were confirmed to be effective as an active ingredient of a pharmaceutical composition for the prevention and treatment of periodontal diseases such as gingivitis and periodontitis.

INDUSTRIAL APPLICABILITY

The novel brominated furanone derivative or a pharmaceutically acceptable salt thereof according to the present invention exhibits an inhibitory activity to quorum sensing of bacteria and also can effectively inhibit the formation of biofilm of bacteria, so that it can be used as an active ingredient of a pharmaceutical composition for the treatment of periodontal diseases such as gingivitis and periodontitis and other oral diseases.

What is claimed is:

1. A compound represented by formula 1 or a pharmaceutically acceptable salt thereof:

[Formula 1]

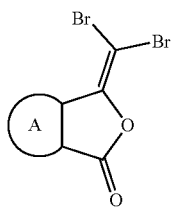

wherein,

X is O or NR$^1$,

R$^1$ is nonsubstituted C$_{1-10}$ straight or branched alkyl; and (A) is nonsubstituted or substituted C$_{5-6}$ cycloalkyl, nonsubstituted or substituted C$_{5-6}$ cycloalkenyl containing one or two double bonds, or substituted phenyl, wherein, the substituted cycloalkyl, the substituted cycloalkenyl, or the substituted phenyl is substituted with one or more substituents selected from the group consisting of hydroxyl, halogen, C$_{1-10}$ straight or branched alkyl, and C$_{1-10}$ straight or branched alkoxy.

2. The compound represented by formula 1 or the pharmaceutically acceptable thereof according to claim 1, wherein (A) is nonsubstituted or substituted C$_{5-6}$ cycloalkyl, nonsubstituted or substituted C$_{5-6}$ cycloalkenyl containing one or two double bonds, or substituted phenyl, wherein, the substituted cycloalkyl, the substituted cycloalkenyl, or the substituted phenyl is independently substituted with one or more substituents selected from the group consisting of C$_{1-5}$ straight or branched alkyl and C$_{1-5}$ straight or branched alkoxy.

3. The compound represented by formula 1 or the pharmaceutically acceptable thereof according to claim 1, wherein R$^1$ is phenyl or n-butyl; and (A) is

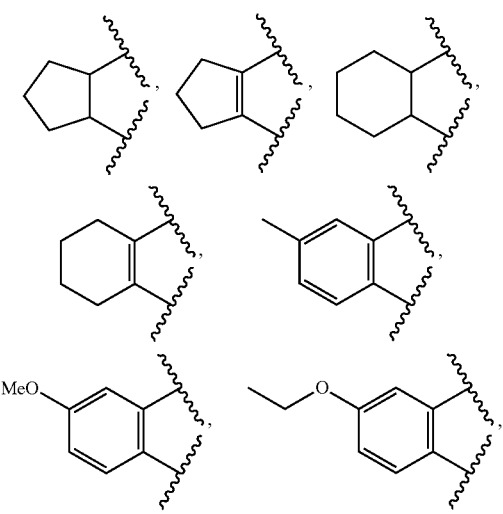

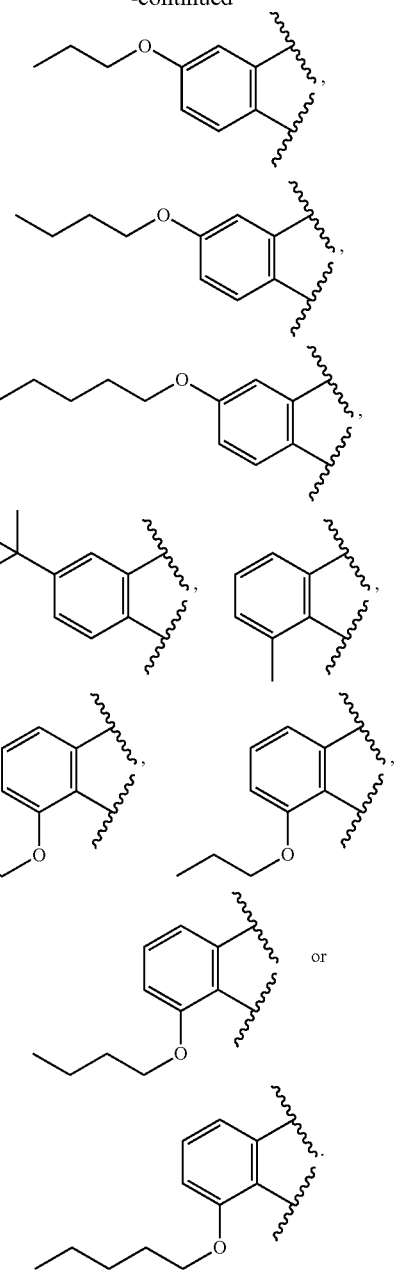

4. A compound or the pharmaceutically acceptable thereof, wherein the compound is selected from the following compounds:

3-(dibromomethylene)-hexahydroisobenzofuran-1(3H)-one;

3-(dibromomethylene)-4,5,6,7-tetrahydroisobenzofuran-1(3H)-one;

3-(dibromomethylene)-5,6-dihydro-3H-cyclopenta[c]furan-1(4H)-one;

3-(dibromomethylene)-hexahydrocyclopenta[c]furan-1(3H)-one;

3-(dibromomethylene)-5-methylisobenzofuran-1(3H)-one;

3-(dibromomethylene)-5-methoxyisobenzofuran-1(3H)-one;

3-(dibromomethylene)-5-ethoxyisobenzofuran-1(3H)-one;

3-(dibromomethylene)-5-propoxyisobenzofuran-1(3H)-one;
5-butoxy-3-(dibromomethylene)isobenzofuran-1(3H)-one;
3-(dibromomethylene)-5-(pentyloxy)isobenzofuran-1(3H)-one;
5-tert-butyl-3-(dibromomethylene)-5-methylisobenzofuran-1(3H)-one;
3-(dibromomethylene)-7-methylisobenzofuran-1(3H)-one;
3-(dibromomethylene)-7-ethoxyisobenzofuran-1(3H)-one;
3-(dibromomethylene)-7-propoxyisobenzofuran-1(3H)-one;
7-butoxy-3-(dibromomethylene)isobenzofuran-1(3H)-one;
3-(dibromomethylene)-7-(pentyloxy)isobenzofuran-1(3H)-one; and
2-butyl-3-(dibromomethylene)isoindolin-1-one.

5. A preparation method of the compound represented by formula 1 comprising the following steps, as shown in reaction formula 1 below:
   preparing a compound represented by formula 3 from a compound represented by formula 2 (step 1); and
   preparing the compound represented by formula 1 from the compound represented by formula 3 prepared in step 1 (step 2).

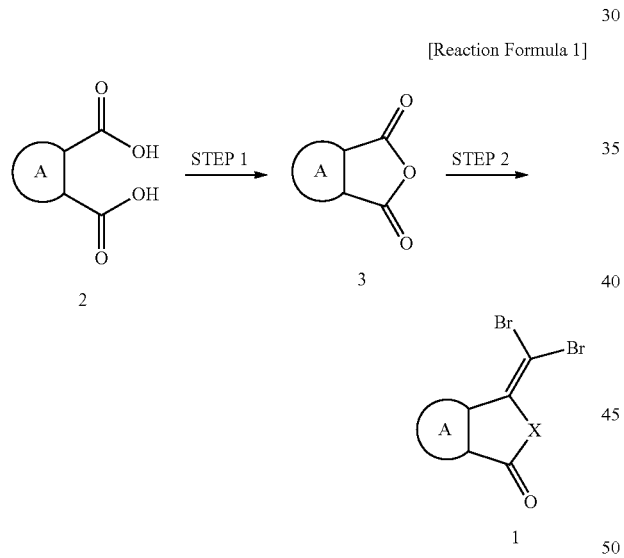

[Reaction Formula 1]

wherein,
Ⓐ is as defined in formula 1 of claim 1; and
X is O.

6. A preparation method of the compound represented by formula 1 comprising the following steps, as shown in reaction formula 2 below:
   preparing a compound represented by formula 3 from a compound represented by formula 2 (step 1);
   preparing a compound represented by formula 4 from the compound represented by formula 3 prepared in step 1 (step 2);
   preparing a compound represented by formula 6 by reacting a compound represented by formula 5 with the compound represented by formula 4 prepared in step 2 (step 3); and
   preparing a compound represented by formula 1 from the compound represented by formula 6 prepared in step 3 (step 4).

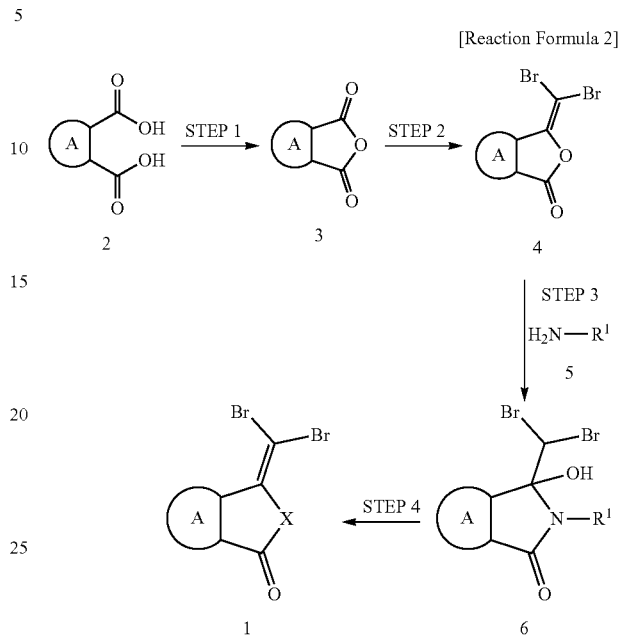

[Reaction Formula 2]

wherein,
Ⓐ and $R^1$ are as defined in formula 1 of claim 1; and
X is $NR^1$.

7. A pharmaceutical composition comprising the compound represented by formula 1″ or a pharmaceutically acceptable salt thereof as an active ingredient for the treatment of periodontal diseases:

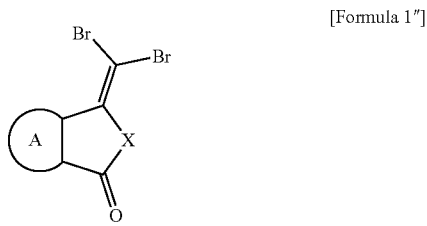

[Formula 1″]

wherein, X is O,
Ⓐ is nonsubstituted or substituted $C_{5-6}$ cycloalkyl, nonsubstituted or substituted $C_{5-6}$ cycloalkenyl containing one or more double bonds, or nonsubstituted or substituted phenyl,
wherein, the substituted cycloalkyl, the substituted cycloalkenyl, or the substituted phenyl is independently substituted with one or more substituents selected from the group consisting of hydroxyl, halogen, $C_{1-10}$ straight or branched alkyl, and $C_{1-10}$ straight or branched alkoxy.

8. The pharmaceutical composition according to claim 7, wherein the compound characteristically inhibits quorum sensing of bacteria.

9. A dentifrice composition comprising the compound represented by formula 1″ of claim 7 or the pharmaceutically acceptable salt thereof as an active ingredient for ameliorating periodontal diseases.

10. A gargle composition comprising the compound represented by formula 1" of claim 7 or the pharmaceutically acceptable salt thereof as an active ingredient for preventing or ameliorating periodontal diseases.

* * * * *